United States Patent
Wu et al.

(10) Patent No.: US 7,612,355 B2
(45) Date of Patent: Nov. 3, 2009

(54) OPTOELECTRONIC TWEEZERS FOR MICROPARTICLE AND CELL MANIPULATION

(75) Inventors: Ming Chiang Wu, Orinda, CA (US); Pei Yu Chiou, Los Angeles, CA (US); Aaron T. Ohta, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 162 days.

(21) Appl. No.: 11/105,304

(22) Filed: Apr. 12, 2005

(65) Prior Publication Data

US 2009/0170186 A1    Jul. 2, 2009

Related U.S. Application Data

(60) Provisional application No. 60/561,587, filed on Apr. 12, 2004.

(51) Int. Cl.
*G01N 21/86* (2006.01)
*G01V 8/00* (2006.01)

(52) U.S. Cl. .................. 250/559.04; 204/547; 204/603

(58) Field of Classification Search ................ 204/643, 204/603, 451, 601, 547; 250/208.1, 559.04, 250/551; 430/58.05, 60, 58.7, 70, 159, 57.5; 372/50.124
See application file for complete search history.

(56) References Cited

U.S. PATENT DOCUMENTS

| | | | |
|---|---|---|---|
| 6,387,707 B1 | 5/2002 | Seul et al. | |
| 6,391,562 B2 * | 5/2002 | Kambara et al. | 435/6 |
| 2002/0031813 A1 | 3/2002 | Ozkan et al. | |
| 2002/0121443 A1 * | 9/2002 | O'Connell | 204/547 |
| 2002/0166766 A1 * | 11/2002 | Seul et al. | 204/450 |
| 2003/0039036 A1 * | 2/2003 | Kruschwitz et al. | 359/707 |
| 2003/0224528 A1 * | 12/2003 | Chiou et al. | 436/164 |

OTHER PUBLICATIONS

W.J. Hossack et al., "High Speed Holographic Optical Tweezers Using a Ferroelectric Liquid Crystal Microdisplay," Optics Express, vol. 11, No. 17, pp. 2053-2059 (2003).

(Continued)

*Primary Examiner*—Thanh X Luu
*Assistant Examiner*—Francis M Legasse, Jr.
(74) *Attorney, Agent, or Firm*—John P. O'Banion

(57) ABSTRACT

An optical image-driven light induced dielectrophoresis (DEP) apparatus and method are described which provide for the manipulation of particles or cells with a diameter on the order of 100 μm or less. The apparatus is referred to as optoelectric tweezers (OET) and provides a number of advantages over conventional optical tweezers, in particular the ability to perform operations in parallel and over a large area without damage to living cells. The OET device generally comprises a planar liquid-filled structure having one or more portions which are photoconductive to convert incoming light to a change in the electric field pattern. The light patterns are dynamically generated to provide a number of manipulation structures that can manipulate single particles and cells or groups of particles/cells. The OET preferably includes a microscopic imaging means to provide feedback for the optical manipulation, such as detecting position and characteristics wherein the light patterns are modulated accordingly.

4 Claims, 41 Drawing Sheets

OTHER PUBLICATIONS

W.J. Hossack et al., "High Speed Holographic Optical Tweezers Using a Ferroelectric Liquid Crystal Microdisplay," Optics Express, vol. 11, No. 17, pp. 2053-2059 (2003).

R.D. Hayward et al., "Electrophoretic Assembly of Colloidal Crystals with Optically Tunable Micropatterns," Nature, vol. 404, Mar. 2, 2000, pp. 56-59.

M. Ozkan et al., "Optical Addressing of Polymer Beads in Microdevices," Sens. Mater., vol. 14, pp. 189-197 (2002).

Y.-S. Lui et al., "Virtual particle Channels Based on Optical Dielectrophoresis Forces," Proceedings IEEE/LEOS International on Optical MEMS, pp. 20-21, Aug. 2004.

Pei Yu Chiou et al., "Cell Addressing and Trapping Using Novel Optoelectronic Tweezers," Proc. IEEE MEMS 2004, pp. 21-24 (2004).

Pei Yu Chiou et al., "A Novel Optoelectronic Tweezer Using Light Induced Dielectrophoresis," Proceedings IEEE/LEOS International Conference on Optical MEMS and Their Applications (OMEMS'03), 2003, pp. 8-9.

Pei Yu Chiou et al., "Optical Actuation of Microfluidics Based on Opto-Electrowetting," Solid-State Sensor, Actuator and Microsystems Workshop, Hilton Head, South Carolina, Jun. 2-6. 2002, pp. 269-272.

Pei Yu Chiou et al., "Light Actuated Microfluidic Devices," Proc. IEEE MEMS, Kyoto, Japan, Jan. 2003, pp. 355-358.

Pei Yu Chiou et al., "Light Actuation of Liquid by Optoelectrowetting," Sensors and Actuators A, vol. 104 (2003), pp. 222-228.

Pei Yu Chiou et al., "Pico Liter Droplet Manipulation Based on a Novel Continuous Opto-Electrowetting Mechanism," Proc. IEEE Transducers 2003, pp. 468-471.

* cited by examiner

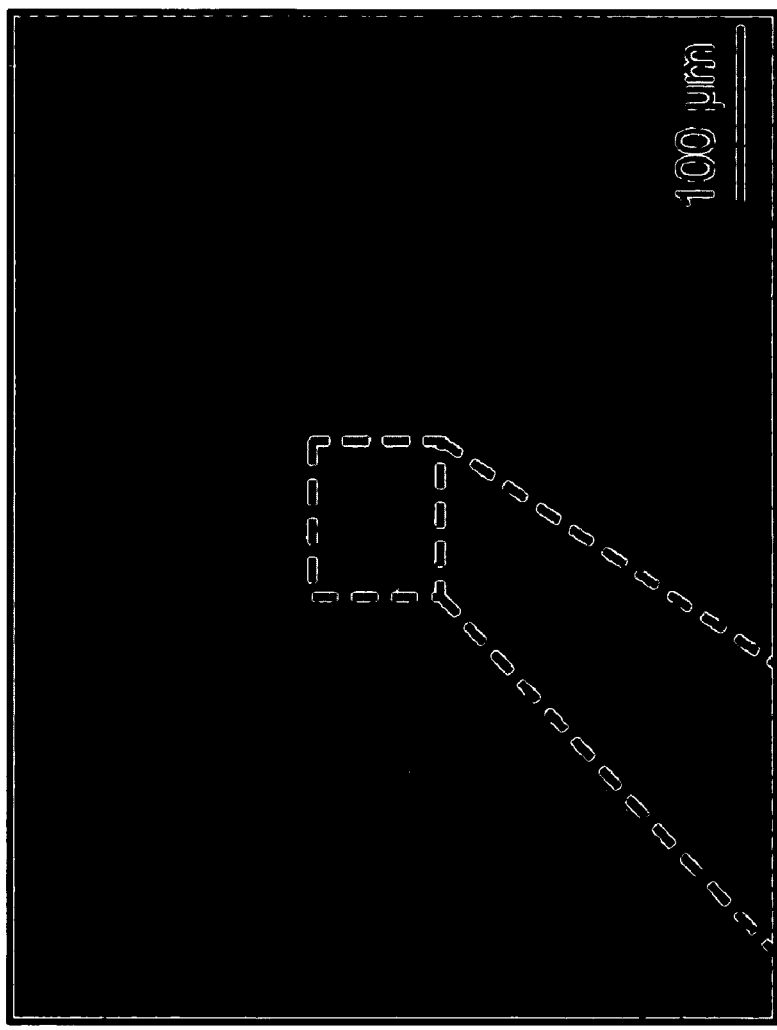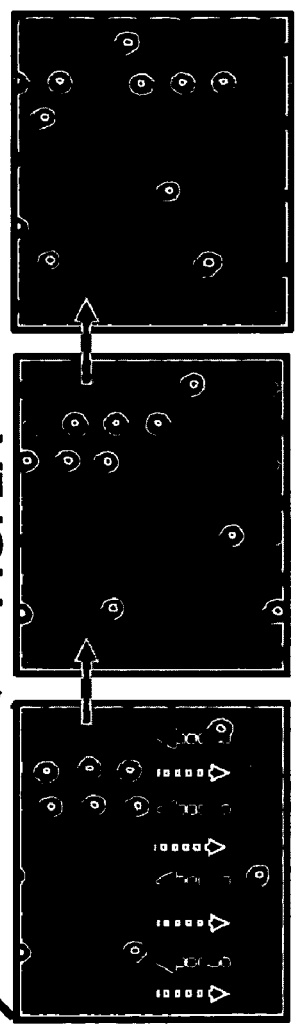

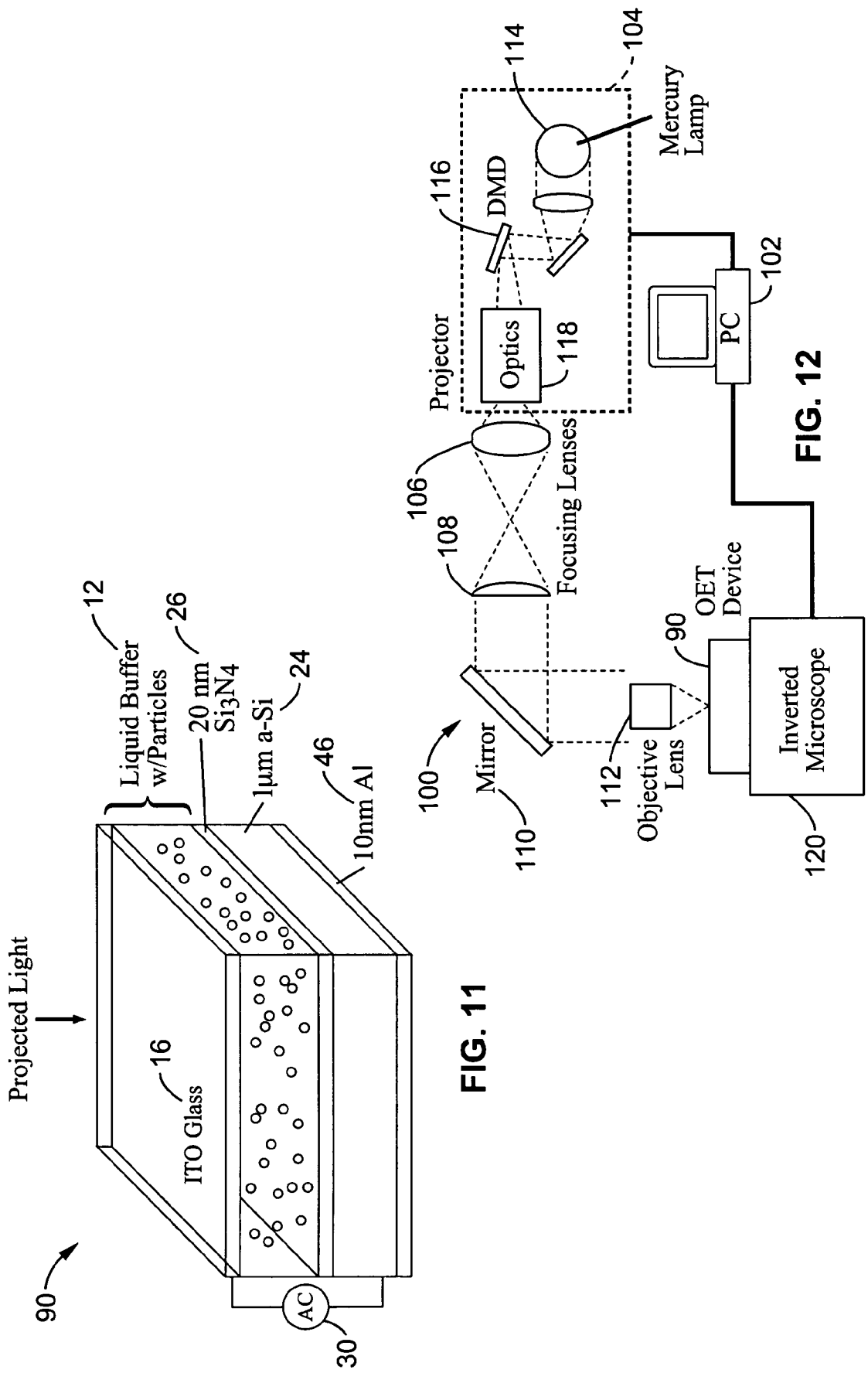

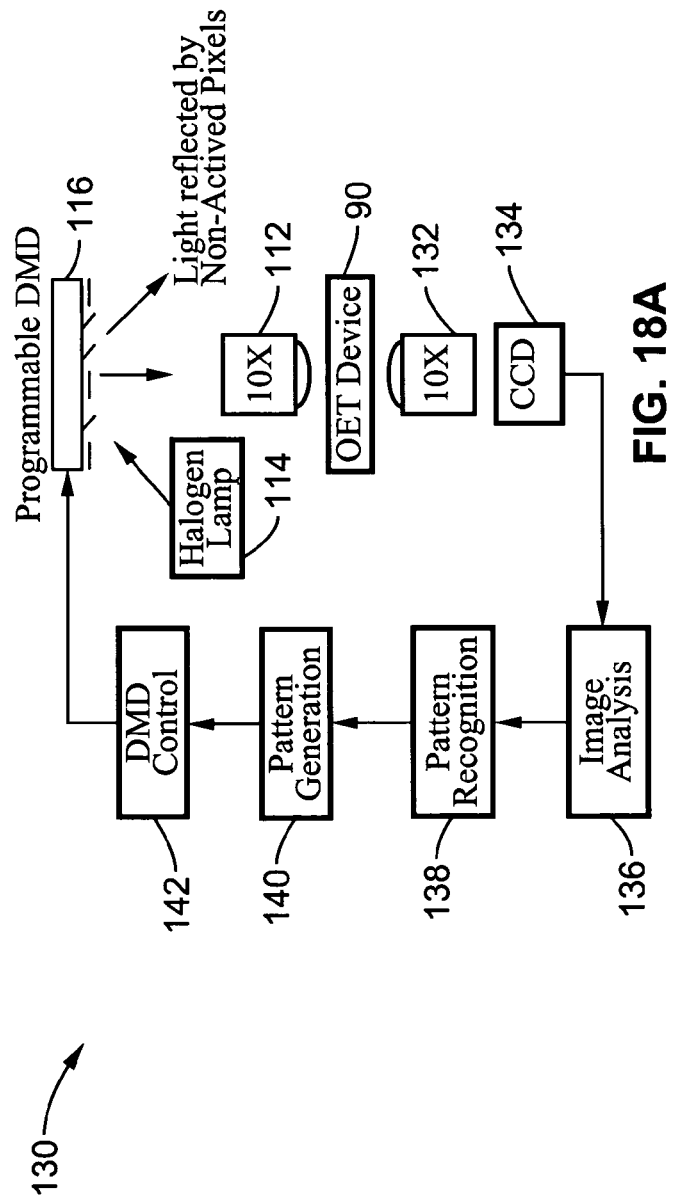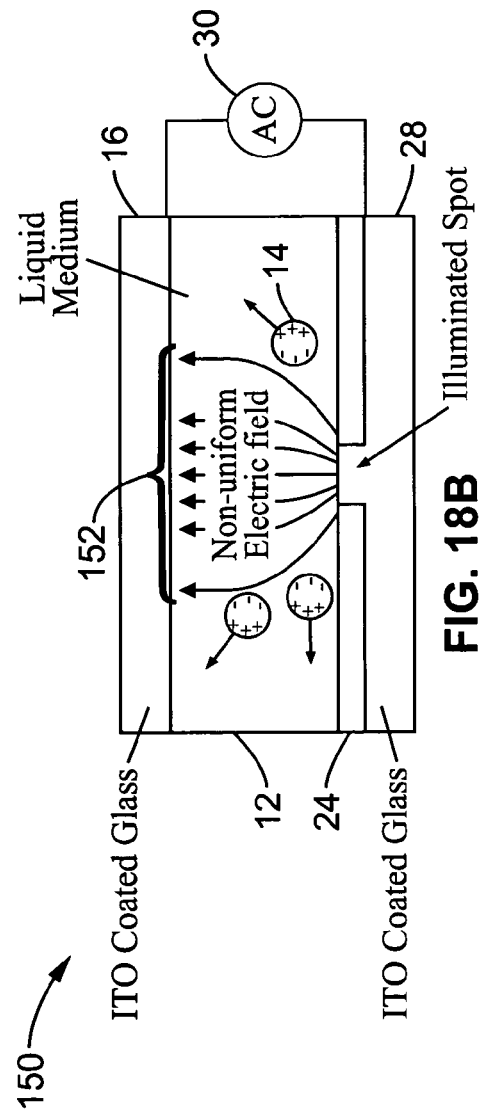
FIG. 18A
FIG. 18B

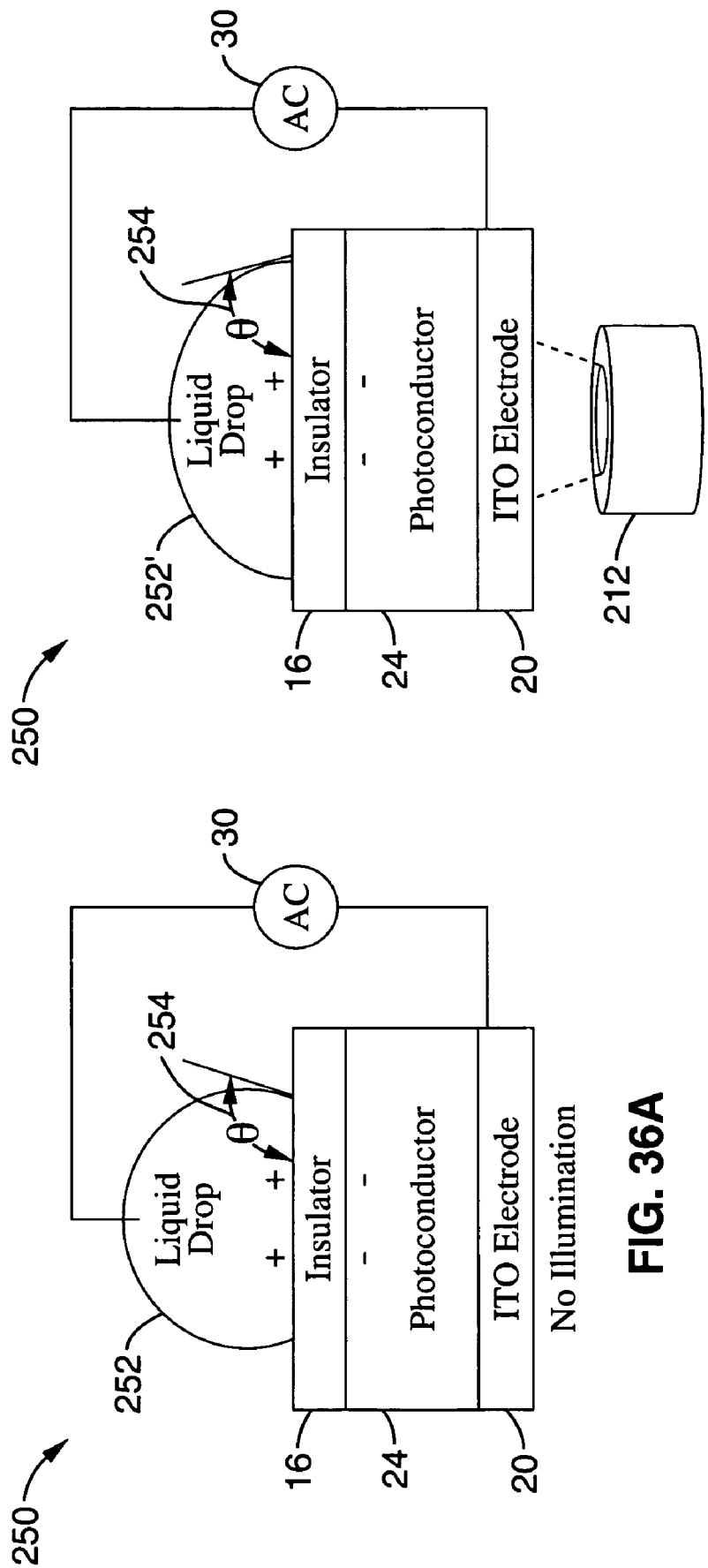

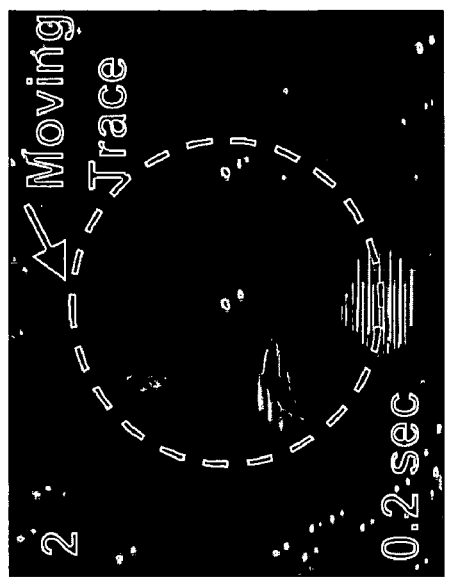
FIG. 38A
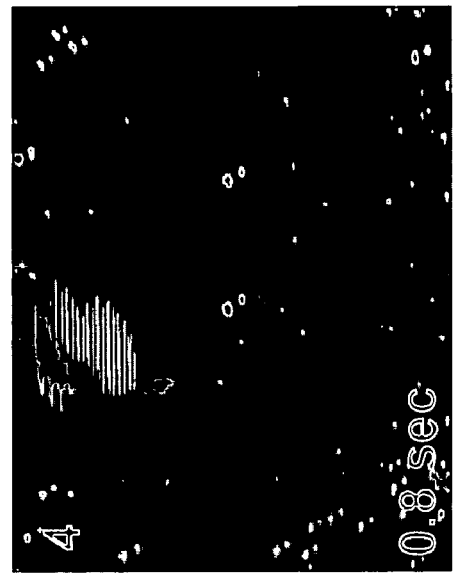
FIG. 38B
FIG. 38C
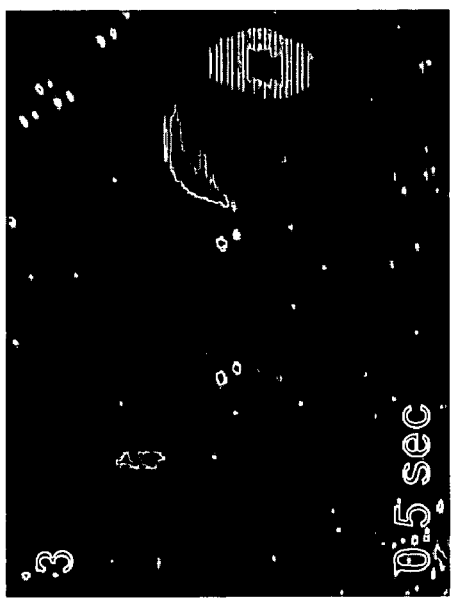
FIG. 38D

OPTOELECTRONIC TWEEZERS FOR MICROPARTICLE AND CELL MANIPULATION

CROSS-REFERENCE TO RELATED APPLICATIONS

This application claims priority from U.S. provisional application Ser. No. 60/561,587 filed on Apr. 12, 2004, incorporated herein by reference in its entirety.

STATEMENT REGARDING FEDERALLY SPONSORED RESEARCH OR DEVELOPMENT

This invention was made with Government support under Grant No. 442521-WM-22622/NCC2-1364, awarded by NASA. The Government has certain rights in this invention.

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This invention pertains generally to cell and microparticle manipulation, and more particularly to optoelectronic tweezers (OET).

2. Description of Related Art

The ability to manipulate biological cells and micrometer scale particles plays an important role in many biological and colloidal science applications. However, conventional manipulation techniques, including optical tweezers, electrokinetic forces (electrophoresis, dielectrophoresis (DEP), traveling-wave dielectrophoresis), magnetic tweezers, acoustic traps, and hydrodynamic flows, cannot simultaneously achieve high resolution and high throughput.

DEP is a well established technique that has been widely used to manipulate micrometer and sub-micrometer particles as well as biological cells. Traveling-wave dielectrophoresis (TWD) is particularly attractive for high throughput cell manipulation without external liquid pumping. The traveling electric field produced by multi-phase alternating current (AC) bias on a parallel array of electrodes levitates and transports many particles simultaneously. However, the TWD cannot resolve individual particles. Recently, a programmable DEP manipulator with individually addressable two-dimensional electrode array has been realized using complementary metal-oxide-semiconductor (CMOS) integrated circuit (IC) technology. Parallel manipulation of a large number (i.e., approximately 10,000) of individual cells was demonstrated. The CMOS DEP manipulator has two potential drawbacks. The need of on-chip IC increases the cost of the chip, making it less attractive for disposable applications. The trap density (i.e., approximately 400 sites/mm$^2$) is also limited by the size of the control circuits.

Consequently, the use of electrokinetic forces and similar mechanisms provide high throughput, but lack the flexibility or the spatial resolution for controlling individual cells, or groups of cells. In addition, these techniques require structures formed through numerous lithographic steps.

Optical tweezers, however, offer high resolution for trapping single particles, yet provide limited manipulation area due to tight focusing requirements. The optical tweezers use direct optical force for the manipulating purpose, and require highly focused coherent light sources used with an objective lens having a high numerical-aperture (N. A.) value and a small field of view. To generate multiple optical traps or special optical patterns, it also requires techniques such as holography. These techniques require intense calculation for creating even simple optical patterns.

Accordingly a need exists for a particle and cell manipulation apparatus and method which provides parallel processing capability while still providing selectivity down to the single particle level. The present invention fulfills those needs, as well as others, and provides for manipulation of particles and cells at low light levels without the need of complex lithography or 3D beam control.

BRIEF SUMMARY OF THE INVENTION

The present invention is directed to performing particle and cell manipulation using optical image-driven light induced dielectrophoresis (DEP). The term "particle" will be used herein to reference microparticles, nanoparticles, cells, and other organic and inorganic material having a diameter generally between a few nanometers up to the order of approximately 100 µm. The techniques allow for the use of moderate intensity incoherent light sources, which create dynamic patterns that can be controlled in response to image detection and processing of actual particle composition and position.

In accordance with one embodiment of the invention, an optical image-driven dielectrophoresis apparatus and method is described for patterning electric fields on a photoconductive surface for manipulating single particles, or collections of particles. A wide variety of light sources can be utilized, such as incoherent light, and single or multistage manipulation of particles can be readily achieved.

One embodiment comprises optoelectronic tweezers (OET) configured for cell and microparticle manipulation using optical control. The OET permits functions such as cell trapping, repelling, collecting, transporting, and sorting of cells and microparticles by using sequentially projected images controlled by a spatial light modulator (e.g., microdisplay or DMD mirrors, and so forth). With optical actuating power as low as 1 mW optical manipulation can be performed using incoherent lightly focused light and a direct image projection system.

In one embodiment, dynamic DMD-driven optoelectronic tweezers perform dynamic manipulation of microscopic particles using a DMD produced projection image. Single-particle trapping and movement (up to 40 µm/sec) via optically-induced dielectrophoresis were observed in this embodiment.

Another embodiment is described in which dynamic array manipulation of particles and microparticles is performed using optoelectronic tweezers. One demonstration details the individual trapping of polystyrene particles with 20 µm and 45 µm diameters trapped by light patterns generated by a digital light projector with digital micromirror device (DMD). Self-organization and individual addressing of the particles are demonstrated. Movement of 45 µm polystyrene particles is measured to be 35 µm/sec (a force of 15 pN).

Another embodiment provides for the manipulation of live red and white blood cells with optoelectronic tweezers. Optically-induced dielectrophoresis is enabled within the optoelectronic tweezers (OET) to manipulate live mammalian cells demonstrated by concentrating bovine red blood cells in solution. A spatial light modulator and an incoherent light source integrated in combination with the OET provide the ability to easily create reconfigurable, complex manipulation patterns. This capability is also demonstrated in the patterning of human white blood cells into complex patterns.

Another embodiment provides for using light induced dielectrophoresis to optically trap and transport micro particles with optical power in the microwatt range. This embodiment comprises two pattern-less (unpatterned) surfaces: a bottom glass substrate coated with photoconductive material and a top transparent indium-tin-oxide (ITO) glass. To achieve optical trapping, the liquid-immersed micro-particles are sandwiched between these two surfaces and an AC electric bias is supplied. A 633 nm He—Ne laser focused by a 40× objective lens is used to transport the particles. Negative dielectrophoretic trapping is demonstrated and the experimental results show that optical beams with power as low as 1 µW are sufficient to transport 25 µm diameter latex particles at a speed of 4.5 µm/sec. The transport speed increases with higher optical power. A maximum speed of 397 µm/sec is observed at 100 µW.

In this embodiment, an optical sorting mechanism is described based on a dynamic electric field patterned by the scanning optoelectronic tweezers (OET). The sorting mechanism is based on the force balance between the hydrodynamic viscous force and the dynamic light-induced dielectrophoretic force. Randomly distributed particles with different sizes are sorted out and positioned in size-dependent deterministic positions relative to a line-shaped scanning laser beam. A 240 µm laser beam moving at a speed of 10 µm/sec can sort polystyrene beads with diameters of 5 µm, 10 µm, and 20 µm to relative positions of 17 µm, 29 µm, and 60 µm from the beam center.

This embodiment also provides for moving toward an all optical lab-on-a-chip system requiring optical manipulation tools for both microparticles and microfluids. Although optical tweezers are important for manipulating cells or particles, they are not effective in handling microfluid. The typically high optical power requirements have also limited the applicability in high throughput bioanalysis system. In this embodiment two novel mechanisms are demonstrated: (1) optoelectrowetting (OEW) for handling microdroplets, and (2) optoelectronic tweezers (OET) for optical manipulation of microscopic particles with low optical power actuation. Instead of using direct optical force, both mechanisms rely on light induced electrical force for optical manipulation. Optoelectrowetting (OEW) enables control of microfluids in droplet form by optical beams and is based on light induced electrowetting, which changes surface tension at solid-liquid interface at illuminated area. It is realized by integrating a layer of photoconductive material with electrowetting electrodes. By programming the illumination pattern, we have successfully demonstrated various functions for droplets, such as moving, splitting, and merging. A 100 pL droplet was transported at a speed of 785 µm/sec by an optical beam with an optical power of 100 µW.

Optoelectronic tweezers (OET) manipulate cells or particles based on light induced dielectrophoresis (DEP). Trapping or repelling of microscopic particles is achieved with a light intensity of 2 W/cm$^2$, which is five orders of magnitudes lower than that required by optical tweezers (approximately 105 W/cm$^2$ to 107 W/cm$^2$). The liquid containing cells or particles is sandwiched between a photosensitive surface and a transparent ITO glass, with an AC bias between them. When the laser beam is focused on the photosensitive layer, it creates a virtual electrode on the illuminated area, resulting a nonuniform electric field at the aqueous layer. Cells or particles in the liquid layer are polarized by this non-uniform electric field and driven by the DEP force. The force could be attractive or repulsive, depending on the dielectric properties of the particles and the bias frequency. Using OET, we have demonstrated concentration of polystyrene particles and live *E. coli* cells using an optical power less than approximately 10 µW.

According to another embodiment of the invention, an apparatus for manipulating cells or particles by light induced dielectrophoresis (DEP) comprises: (a) a first surface and a second surface configured for retaining a liquid comprising particles or cells to be manipulated; (b) at least one photoconductive area on the first or the second surface configured for conversion of received light to a local electric field in the vicinity of the received light; and (c) means for directing light patterns for receipt on the photoconductive area to selectively repel or attract particles or cells in response to the induced local electric field. The light pattern directing means preferably comprises a light source configured for generating two-dimensional light patterns.

In accordance with another embodiment of the invention, an optoelectronic tweezers (OET) apparatus for manipulating cells and particles using optical image-driven light induced dielectrophoresis (DEP) over a two-dimensional area comprises: (a) a first surface and second surface having sufficient separation for retaining a liquid which contains particles, or cells, to be manipulated; (b) at least one photoconductive area on the first or second surface which is configured for conversion of optical energy to an electric field in the photoconductive area to create a local electric field, or virtual electrode, in the vicinity of the received light; and (c) means for dynamic optical image positioning on the at least one photoconductive area to generate moving virtual electrode patterns for manipulating the positioning of particles or cells using light-induced dielectrophoresis (DEP).

Another embodiment of the invention provides an apparatus for manipulating cells or particles by light induced dielectrophoresis (DEP), the apparatus comprising: (a) a first surface and a second surface configured for retaining a liquid comprising particles or cells to be manipulated; (b) at least one photoconductive area on the first or the second surface configured for conversion of received light to a local electric field in the vicinity of the received light; and (c) a light source to provide the light received by the photoconductive area, wherein the local electric field selectively repels or attracts particles or cells.

The light source preferably comprises an optical projection system configured for generating two dimensional light patterns, such as in the form of image sequences or streams upon the photoconductive area.

In a further embodiment of the invention, an optoelectronic tweezers (OET) apparatus for manipulating cells and particles using optical image-driven light induced dielectrophoresis (DEP) over a two-dimensional area, comprises: (a) a first surface and second surface having sufficient separation for retaining a liquid which contains particles, or cells, to be manipulated; (b) at least one photoconductive area on the first or second surface which is configured for inducing an electric field, thereby creating a virtual electrode, in the vicinity of the received light (or similarly converting optical energy to an electric field) and (c) an optical projector configured for generating dynamic sequential two-dimensional light patterns onto the photosensitive surface thereby inducing dynamic localized electric fields for DEP manipulation of particles or cells.

The optical projector, or similar means of dynamically projecting light images is preferably directed at the OET through a lens assembly, so that a sequence of images can be formed onto the photoconductive area. In one preferred embodiment of the invention electrodes are coupled to the first and second surfaces so that a bias signal can be applied to the liquid with the contained particles or cells.

According to one aspect of the invention, a means is provided to perform microscopic imaging of the particles and/or cells and to register the position, and optionally the characteristics, of particles and/or cells to provide feedback for controlling optical image positioning and dynamic image movement.

Another embodiment of the invention provides an optoelectronic tweezers (OET) apparatus for manipulating cells and particles (typically on the order of 100 μm diameter or less) using optical image-driven light induced dielectrophoresis (DEP) over a two-dimensional area, comprising: (a) a first surface and second surface having sufficient separation for retaining a liquid which contains particles and/or cells to be manipulated; (b) at least one photoconductive area on the first or second surface which is configured for conversion of optical energy to an electric field in the photoconductor to create a local electric field, or virtual electrode, in the vicinity of the received light; (c) an optical projector coupled to a lens assembly configured for generating dynamic sequential images (a sequence of light patterns) through the lens assembly onto the photosensitive surface for creating dynamic localized electric fields for the DEP manipulation of nearby particles and/or cells.

The first surface and second surface preferably form a continuous film upon which DEP manipulation is performed in response to images received from the optical projector. In this way lithographic patterning with conductive electrodes is not necessary for performing DEP manipulation.

In one mode of the invention at least one electrode is coupled to each of the first and second surface so that a bias signal can be applied to the liquid with its particles and/or cells. The liquid preferably comprises a conductive or semiconductive fluid. Typically a thin dielectric layer is joined to the interior surface of the electrodes and configured to have an impedance that is less than the impedance across the liquid.

In a preferred mode of the invention a microvision-based pattern recognition subsystem is configured for controlling the output of the optical projector in response to registering the position of, and optionally the characteristics of, particles and/or cells as determined from microscopic imaging. The characteristics can comprise anything which is directly detectable by the microscopic imaging system or which can be determined in response to detecting changes in the direct characteristics over time. By way of example the characteristics can include size, color, shape, texture, viability, motility, conductivity, permeability, capacitance and response to changes in the environment of the particle or cell.

Another embodiment of the invention is an apparatus for manipulating cells by light induced dielectrophoresis (DEP), the apparatus comprising: (a) a first surface and a second surface configured for retaining a liquid comprising cells to be manipulated; (b) at least one photoconductive area on the first or the second surface configured for inducing a local electric field in response to received light; (c) a light source to provide the light received by the photoconductive area, wherein the local electric field induced by the light selectively repels or attracts cells and wherein the light received is of sufficiently low optical intensity that it does not damage the cells being manipulated in the apparatus. In one preferred mode the embodiment further comprises a microscopic imaging subsystem configured for controlling the output of the light source in response to registering the position of, and optionally the characteristics of cells within the apparatus.

Another embodiment provides a method of manipulating particle or cellular objects retained within a liquid, the method comprising the steps consisting essentially of: (a) confining the liquid comprising the particle objects or cellular objects within a structure comprising at least a first and second surface; (b) applying a bias voltage to the liquid by applying a bias signal to electrodes coupled to the first and second surfaces; (c) directing light to a photoconductive portion of the structure, wherein the light induces a local electric field in the vicinity of the portion receiving light thereby dielectrophoretically repelling or attracting the particles or cells.

Another embodiment provides a method of manipulating biological objects retained within a liquid, the method comprising: (a) confining the liquid comprising the particle objects or cellular objects within a structure comprising at least a first and second surface; (b) applying a bias voltage to the liquid by applying a bias signal to electrodes coupled to the first and second surfaces; (c) generating control signals in response to registering the characteristics and positions of biological objects within the structure; (d) directing light in response to the control signals upon a photoconductive portion of the structure to induce a local electric field in the vicinity of the received light to dielectrophoretically repel or attract cellular objects, wherein the light is of sufficiently low intensity that live cells being manipulated by the method remain alive and viable.

Another embodiment of the invention generally provides a method of dynamically manipulating particle and cellular objects retained within a liquid, comprising: (a) confining a liquid containing particle objects, and/or cellular objects within a structure having at least a first and second surface; (b) applying a bias voltage to the liquid by applying a bias signal to electrodes coupled to the first and second surfaces; (c) focusing a light pattern on a photoconductive portion of the first surface and/or second surfaces, so that the optical energy of the light is converted to a local electric field to create a virtual electrode in the vicinity of the received light; and (d) dynamically positioning the light pattern in response to feedback received from registering the position, and optionally characteristics, of the particles and/or cells.

Another embodiment of the invention provides a method of dynamically sorting cells retained within a liquid, comprising: (a) confining a liquid contains cells within a structure having at least a first and second surface; (b) applying a bias voltage to the liquid by applying a bias signal to electrodes coupled to the first and second surfaces; (c) generating control signals in response to registering the characteristics and positions of cells within the structure and determining into which category cells are to be sorted; (d) directing light, of sufficient low intensity to prevent cellular damage, in response to the control signals upon a photoconductive portion of the structure to induce a local electric field in the vicinity of the received light to dielectrophoretically repel or attract the cells; and (e) sequentially directing light in response to the control signals to move categorized cells into different sort groups within the structure or for conveyance outside of the structure.

A still further embodiment of the invention provides a method of dynamically sorting particles or cells retained within a liquid, comprising: (a) confining a liquid containing particles or cells within a structure having at least a first and second surface; (b) applying a bias voltage to the liquid by applying a bias signal to electrodes coupled to the first and second surfaces; and (c) directing a moving pattern of light across a photoconductive portion of the structure to induce a local electric field in the vicinity of the pattern to dielectrophoretically repel particles or cells displacing them from the pattern according to their relative size.

Embodiments of the present invention can provide a number of beneficial aspects which can be implemented either separately or in any desired combination without departing from the present teachings.

An aspect of the invention is to provide an apparatus and method for manipulating cells and particles using optical image-driven light induced dielectrophoresis (DEP) within a generally planar liquid-filled structure.

Another aspect of the invention is performing optical image-driven light induced DEP over a large two-dimensional area adjacent to a fluid containing single particles and/or cells, collections of particles and/or cells, or a combination thereof.

Another aspect of the invention is performing optical image-driven light induced DEP in which single particles and/or cells, or particle groups and/or cell groups, can be manipulated in parallel (simultaneously).

Another aspect of the invention is performing optical image-driven light induced DEP wherein any of the particles or groups of particles can be manipulated in any desired direction within the apparatus as they are not constrained by a physical electrode structure.

Another aspect of the invention allows for performing optical image-driven light induced DEP using conventional materials and processing techniques.

Another aspect of the invention allows for performing optical image-driven light induced DEP on particles which may be electrostatically neutral.

Another aspect of the invention allows for performing optical image-driven light induced DEP in an optoelectric tweezers device (OET) which achieves high resolution and high throughput simultaneously.

Another aspect of the invention allows for performing optical image-driven light induced DEP in an optoelectric tweezers device (OET) which creates dynamic electric fields to manipulate particle positioning without the assistance of fluidic flow.

Another aspect of the invention allows for performing optical image-driven light induced DEP in an optoelectric tweezers device (OET) which is capable of manipulating the position of particles and cells at less than approximately 10 µW which is about $1/100,000^{th}$ of the optical energy level required by conventional optical tweezers.

Another aspect of the invention allows for an optoelectric tweezers device (OET) in which tight optical focusing is not required thereby allowing manipulation over a maximum area on the order of one square millimeter (1 mm$^2$), or larger up to, such as 1.3 mm×1.0 mm which is many orders of magnitude larger than that which is achievable using conventional optical tweezers.

Another aspect of the invention allows for performing optical image-driven light induced DEP in an optoelectric tweezers device (OET) in combination with continuous optical electrowetting techniques (COEW).

Another aspect of the invention is an OET device having a first surface and second surface separated by chamber walls and configured for retaining a liquid which contains particles, or cells, being manipulated.

Another aspect of the invention is an OET device having electrodes on the first and second surface upon which a biasing current and/or field can be applied through and/or across the retained liquid.

Another aspect of the invention is an OET device having at least one photosensitive/photoresponsive surface which creates a local electric field in response to received light, therein creating virtual electrodes for manipulating particles, cells, and the like at low optical power levels.

Another aspect of the invention is an OET device having first and second surfaces formed as a continuous film, wherein lithographic patterning of the surface is not necessary for practicing the invention.

Another aspect of the invention is an OET device having surfaces of amorphous and/or micro/nano-crystalline semiconductor materials, amorphous Si, or organic photoconductor materials, used with or without dielectric layers, such as silicon nitride, silicon dioxide, and so forth.

Another aspect of the invention is an OET device having thin dielectric layers with a lower impedance than the liquid retained in the OET device.

Another aspect of the invention is an OET device using a single or double-sided photosensitive surface in various combinations with a conductive surface, non-conductive surface, or no opposing surface (open structure).

Another aspect of the invention is an OET device configured for implementing traps, combs, sorters, concentrators, loops, conveyers, joints, particle channels, wedges, sweepers, which can be implemented separately, in arrays of manipulation elements, and combinations and sequences of manipulation elements and so forth.

Another aspect of the invention is an OET device wherein the surface integrates with microfluidic devices, such as channels, cavities, reservoirs, and pumps.

Another aspect of the invention is an OET device for implementing a comb device for separating particles, cells, and other micro/nano-particles in response to their size.

Another aspect of the invention is an OET device which can be biased with AC of a desired frequency, and/or DC biasing.

Another aspect of the invention is an OET device in which the frequency of the AC bias determines whether particles, cells, and the like are attracted or repelled by the patterned light.

Another aspect of the invention is an OET device in which a microscopic imaging means operates in combination with the dynamic light patterning device so that patterns are created in response to the actual positioning of particles, cells, and the like within the OET device.

Another aspect of the invention is an OET device in combination with a microscopic imaging device which is configured to provide feedback to the OET device during the characterization and positioning of particles.

Another aspect of the invention is an OET device in which the microscopic imaging means is configured for analyzing the actual positioning and composition of particles, cells, and so forth and controlling the generation of light output sequences for moving, collecting, and/or dispersing the particles, cells, and so forth in response to actual positions detected by the imaging means.

Another aspect of the invention is an OET device in which a conductive or semiconductive fluid is retained in the device.

Another aspect of the invention is an OET device which is configured for manipulating particles and cells in response to light patterns, and in particular dynamic lighting patterns.

Another aspect of the invention is an OET device in which dynamic lighting patterns are generated to sequentially move particles, cells and so forth, in response to the light pattern motion.

Another aspect of the invention is an OET device in which the lighting patterns are generated by a laser or more preferably a low-intensity incoherent light source (i.e., halogen, LEDs, and so forth).

Another aspect of the invention is an OET device in which the use of low-intensity lighting is made possible by the conversion of optical energy to an electric field in the photoconductor.

Another aspect of the invention is an OET device configured for sorting particles, or biological cells, in response to differences in viability (i.e., dead or alive), internal conductivity, size, color, shape, texture, response to changes in the aqueous environment, and similar distinguishing characteristics.

Another aspect of the invention is an OET device configured for sorting biological cells in response to differences in membrane properties (e.g., permeability, capacitance, and so forth), internal conductivity, and the like.

Another aspect of the invention is an OET device in which the use of low-intensity lighting allows for manipulating biological objects without loss of viability from photodamage ("opticution") which arises when using conventional optical tweezers.

Another aspect of the invention is an OET device in which the use of low-intensity lighting is made possible by the conversion of optical energy to an electric field in the photoconductor.

Another aspect of the invention is an OET device in which the light source is patterned by a spatial light modulator, or similar form of light modulator.

Another aspect of the invention is an OET device on which the light patterns are varied in response to magnification or demagnification.

A still further aspect of the invention is an OET device for use in biological analysis, cell manipulation, colloidal assembly, particle sorting, particle assembly, and so forth.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIGS. 2A-2D are images of particle manipulation using particle traps according to an aspect of the present invention, showing particles being trapped in a am array.

FIG. 11 is a perspective view of an OET device according to an aspect of the present invention, showing particles in the liquid buffer retained between the top and bottom layers of the OET.

FIG. 12 is a block diagram of an experimental OET setup according to an aspect of the present invention, showing light controlled from a PC directed using DMD onto the OET device.

FIG. 18A is a schematic diagram of a microvision-based automatic optical manipulation system according to an aspect of the present invention.

FIG. 18B is a schematic of the OET device shown in the system of FIG. 18A.

FIGS. 36A-36B are schematics of an OEW device according to an aspect of the present invention, showing the change in droplet characteristics when the device is illuminated.

FIGS. 38A-38D are images of microdroplet transport utilized COEW according to an aspect of the present invention.

DETAILED DESCRIPTION OF THE INVENTION

Referring more specifically to the drawings, for illustrative purposes the present invention is embodied in the apparatus generally shown in FIG. 1 through FIG. 44. It will be appreciated that the apparatus may vary as to configuration and as to details of the parts, and that the method may vary as to the specific steps and sequence, without departing from the basic concepts as disclosed herein.

The present invention includes numerous embodiments in which particles, cells, and other elements suspended in a fluid are manipulated. The application describes these embodiment within nine sections.

1. Massively Parallel Manipulation Using Optical Images.

An optical image-driven dielectrophoresis technique is described herein that permits high-resolution patterning of electric fields on a photoconductive surface for manipulating single particles. The technique can be performed at substantially lower light intensity levels than were required using previous techniques, for example one embodiment requires approximately 100,000 times less optical intensity than optical tweezers. In addition, the technique can make use of incoherent light sources. In one example an incoherent light source (a light emitting diode (LED) or a halogen lamp) is utilized with a digital micromirror spatial light modulator to demonstrate parallel manipulation of 15,000 particle traps within a 1.3 mm×1 mm area. With direct optical imaging control, multiple manipulation functions can be easily combined to achieve complex, multi-step manipulation protocols.

It has not been appreciated in the industry that optically-induced electrophoresis could be could be controlled with a dynamic optical addressing mechanism to provide the capability to perform manipulation down to the single particle level. The optoelectronic tweezers (OET) of the present invention utilizes direct optical images to create high-resolution DEP electrodes for the parallel manipulation of single particles. DEP force results from the interaction of the induced dipoles in particles subjected to a non-uniform electric field. The magnitude of the force depends on the electric field gradient and the polarizability of the particle, which is dependent on the dielectric properties of the particle and the surrounding medium.

Figure 1:
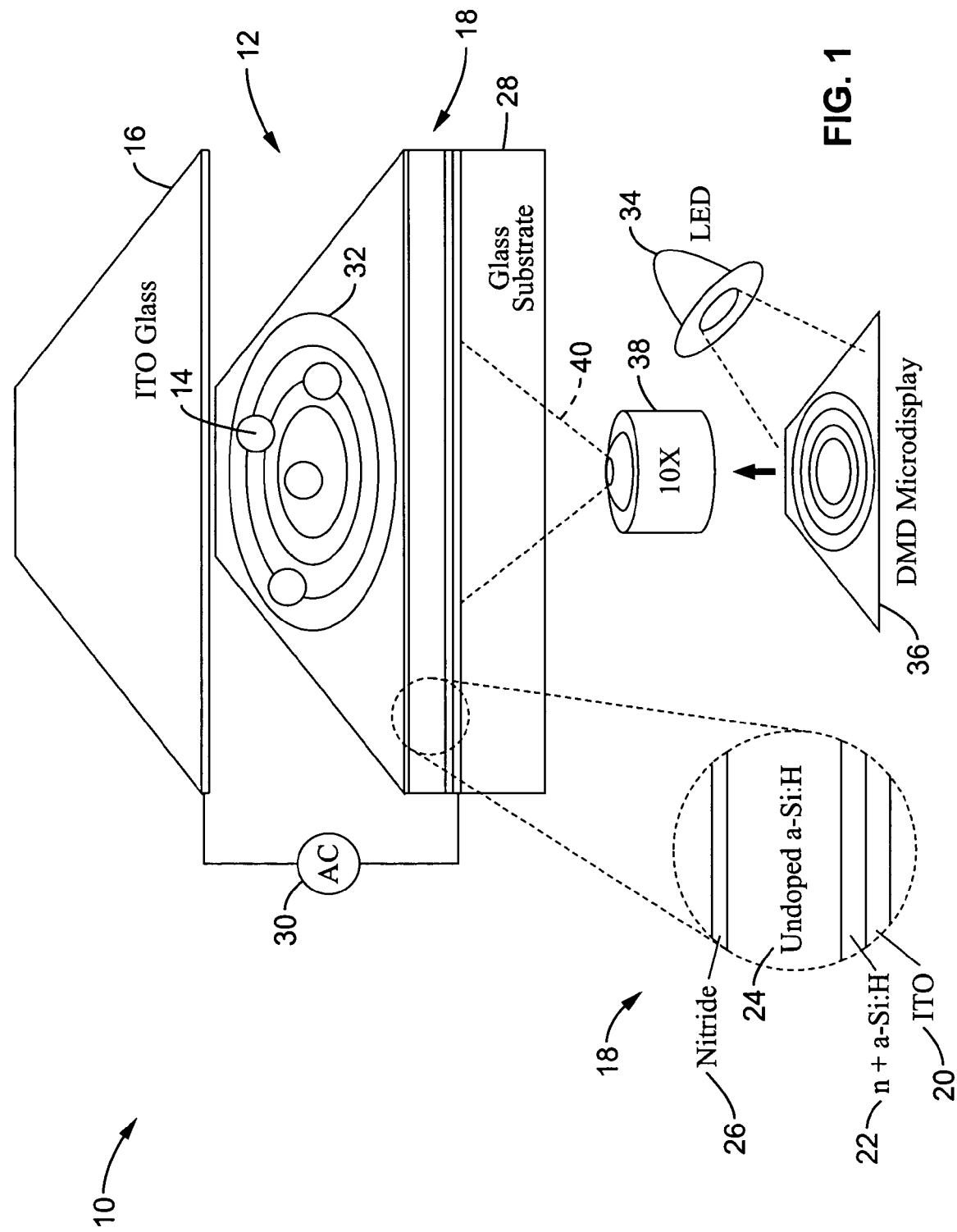
FIG. 1 is a perspective schematic view of optoelectronic tweezers (OET) according to an aspect of the present invention for manipulating microscopic particles sandwiched between structure layers biased with an AC signal.

FIG. 1 illustrates an example embodiment 10 of optoelectronic tweezers (OET) according to the present invention. Liquid 12 that contains microscopic particles (or cells) 14 is sandwiched between the upper layer 16, such as comprising a transparent conductive ITO glass, and the bottom layer 18, such as comprising a photosensitive surface fabricated from an ITO-coated glass 20 topped with multiple preferably featureless layers with 50 nm of heavily doped a-Si:H 22, 1 μm of undoped a-Si:H 24, and 20 nm of silicon nitride 26. By way of example the lower layer is shown upon a glass substrate 28.

The top 16 and bottom 18 surfaces are coupled to a bias source 30 such as an AC electric signal of 10 $V_{PP}$. Alternatively, the surfaces can be less preferably DC biased, or biased with a combination of AC and DC, depending on the specific device structure and manipulation application. It should be appreciated that the frequency of the AC bias determines whether particles, cells, and the like are attracted or repelled by the patterned light, wherein the use of AC provides a number of advantages over the use of a DC bias.

The photosensitive surface 24 of the lower layer converts the received optical energy into a corresponding electric field, shown by way of illustration by the set of concentric rings 32 of FIG. 1. The illumination source may be any convenient light source, such as an LED 34 operating at a wavelength of 625 nm (i.e., manufactured by Lumileds®, Luxeon® Star/O®) as depicted in this example. An optical projection means provides a mechanism for outputting light patterns onto the photosensitive lower layer 18, and preferably is configured for outputting dynamic light patterns having spatial intensity variation over the surface, and typically structures defined by light or dark regions, which are output in a pattern stream (i.e., similar to a movie), or a pattern sequence (i.e., similar to a slide show). One preferred technique for projecting the light patterns is using a spatial light modulation means 36, such as a digital micromirror display (DMD) which in combination with objective 38 focuses the light from LED 34 onto the photosensitive surface 24 creating the non-uniform electric field for DEP manipulation.

When projected light illuminates the photoconductive layer, it turns on the virtual electrodes, creating non-uniform electric fields and enabling particle manipulation via DEP forces. These featureless layers can be made without using any lithography or microfabrication, making the device inexpensive and attractive for disposable applications. The OET-based optical manipulation has two operational modes, positive OET and negative OET, as a result of DEP forces induced for actuation. Particles can be attracted by or repelled from the illuminated area, depending on the AC electric field frequency and the internal and surface dielectric properties of the particle.

As a consequence of the high photoconductive gain, the minimum optical intensity required to turn on a virtual electrode is 10 nW/μm$^2$, which is approximately 100,000 times lower than that of optical tweezers. This low threshold of optical intensity opens up the possibility of using incoherent optical images to control the DEP forces over a large area, such as over a maximum area on the order of one square millimeter (1 mm$^2$), or even larger depending on optical configuration. For example, the optical images are created in one embodiment by combining an LED and a digital micromirror spatial light modulator (i.e., a DMD device such as by Texas Instruments® having 1024×768 pixels with a 13.68 μm×13.68 μm pixel size). The pattern is imaged onto the photoconductive surface through a 10× objective. The resulting pixel size of the virtual electrode is 1.52 μm. The illumination source for the example was a red LED (625 nm wavelength) with 1 mW output power (measured after the objective lens), which is sufficient to actuate 40,000 pixels. Tight focusing is not required for OET, and the optical manipulation area can be magnified by choosing appropriate objective lens. Using a 10× objective, the manipulation area (1.3 mm×1.0 mm) is 500 times larger than that of optical tweezers.

The patterning of high-resolution virtual electrodes is critical for achieving single particle manipulation. OET has higher resolution than the optically-induced electrophoretic methods reported previously. The minimum size of the virtual electrode is limited by the lateral diffusion length of the photogenerated carriers in the photoconductor as well as the optical diffraction of the objective lens. The large number of electronic defect states in undoped a-Si:H results in a short ambipolar electron diffusion length of less than 115 nm. The ultimate virtual electrode resolution is thus determined by the optical diffraction limit. In addition, the induced OET force is proportional to the gradient of the square of the electric field, making it well confined to the local area of the virtual electrodes, which is also a key property for single particle manipulation.

It should be appreciated that the OET of FIG. 1 may be implemented with a number of variations according to the present invention, the following being provided by way of example. The OET device is provided with a first surface and second surface separated by chamber walls and configured for retaining a liquid which contains particles, or cells, being manipulated. It is preferred that electrodes are provided on the first and second surfaces of the OET upon which a biasing current and/or field can be applied through and/or across the retained liquid. FIG. 1 is shown with a single photoconductive surface. However, the present system may be implemented having at least one photosensitive/photoresponsive surface which induces a local electric field on the surface of the material in response to received light, therein creating virtual electrodes for manipulating particles, cells, and the like at low optical power levels. It should be understood that the OET according to the invention may be created with a single or double-sided photosensitive surface, in various combinations with a conductive surface, non-conductive surface, or no opposing surface (open structure).

The first and second surfaces of the OET are preferably formed as a continuous film, wherein lithographic patterning of the surface is not necessary for practicing the invention. However, it should be appreciated that the OET of the present invention can be implemented in combination with conventional DEP structures or continuous optical electrowetting techniques (COEW) toward specific application areas.

The OET of FIG. 1 can be configured having surfaces of amorphous and/or micro/nano-crystalline semiconductor materials, amorphous Si, or organic photoconductor materials, used with or without dielectric layers, such as silicon nitride, silicon dioxide, and so forth. When used, the thin dielectric layers of the OET, having an impedance that is much less than the impedance across the liquid retained in the OET device.

FIG. 2A through FIG. 2D illustrate results from an embodiment of the device which provides massively parallel manipulations of single particles across 15,000 particle traps created across a 1.3 mm×1.0 mm area. The 4.5 μm diameter polystyrene beads experiencing negative DEP forces are trapped in the dark area.

FIG. 2A depicts a portion of the array, with each trap in this particular embodiment having a diameter of 4.5 μm to fit a single particle.

FIG. 2B illustrates by way of example parallel transporting of single particles with three snapshots from the captured video showing the particle motion within this section of the manipulation area. The trapped particles in two adjacent columns move in opposite direction as seen in FIG. 2C and FIG.

2D. The induced negative DEP forces push the beads into the non-illuminated regions, where the electric field is weaker. The size of each trap is optimized to capture a single 4.5 µm diameter polystyrene bead.

By programming the projected images, these trapped particles can be individually moved in parallel as shown in FIG. 2B. Compared with the programmable CMOS DEP chip, the particle trap density of the OET (11,500 sites/mm$^2$) is 30 times higher in response to the high-resolution addressing ability. Using direct imaging, sophisticated virtual electrodes can be easily patterned and reconfigured to create dynamic electric field distributions for continuous particle manipulation without the assistance of fluidic flow.

Figure 3A:
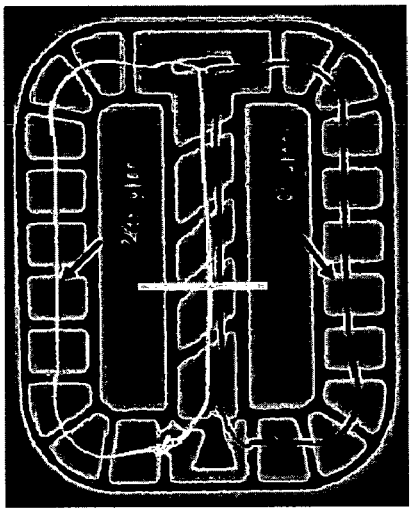
FIGS. 3A-3D are images of an integrated virtual optical machine according to an aspect of the present invention with a sorter, conveyor, joints, and a wedge for sorting microparticles.

FIG. 3A through FIG. 3D illustrate an embodiment by way of example of an integrated virtual optical machine in which the motion of different components is synchronized. In FIG. 3A, the image illustrates the structure which integrates a number of virtual components including an optical sorter path, conveyers, joints and a wedge. It should be appreciated that the OET device of the present invention can be configured for implementing a large variety of traps, combs, sorters, concentrators, loops, conveyers, joints, particle channels, wedges, sweepers, which can be implemented separately, in arrays of manipulation elements, and combinations and sequences of manipulation elements and so forth, without departing from the teachings of the present invention.

Figure 3B:
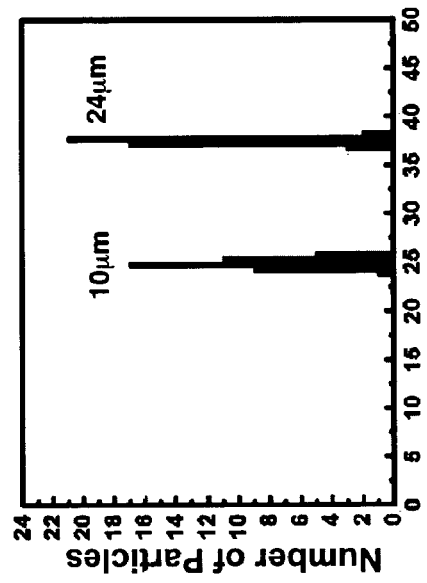
Figure 3C:
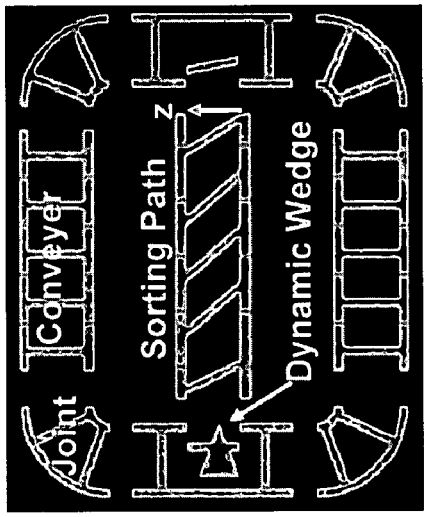

In FIGS. 3B-3C, two polystyrene particles with sizes of 10 µm and 24 µm pass through the sorter path and are fractionated in the z-direction due to the asymmetry optical patterns. The particle traces can be switched at the end of the sorter path by reconfiguring the tip position of the optical wedge. The trajectories of particle movement are highly repeatable and accurately defined, as can be seen in FIG. 3B and FIG. 3C in which the optical sorting repeatability is represented by the dark and light tracks. The light and dark loops in FIG. 3B represent the particle traces after 43 cycles. The trace broadening at the checking bar has a standard deviation of 0.5 µm for the 10 µm bead and 0.15 µm for the 24 µm bead.

It should be appreciated that particles are transported through different functional areas and recycled in this light-patterned circuit, traveling through different paths depending on the position of the wedge divider. Particles with different sizes are fractionated in the lateral z direction as they pass through the sorter path due to the asymmetric shape of the light-patterned electric fields. At the end of the sorter path, an optical wedge divides and guides the particles into the two conveyers. The looped optical conveyers recycle the particles back to the sorter input to repeat the process.

Figure 3D:
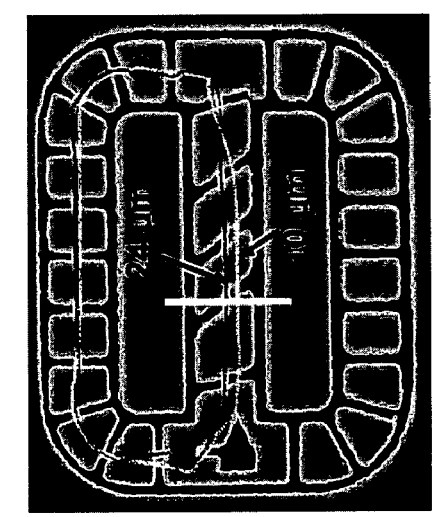
Figure 4A:
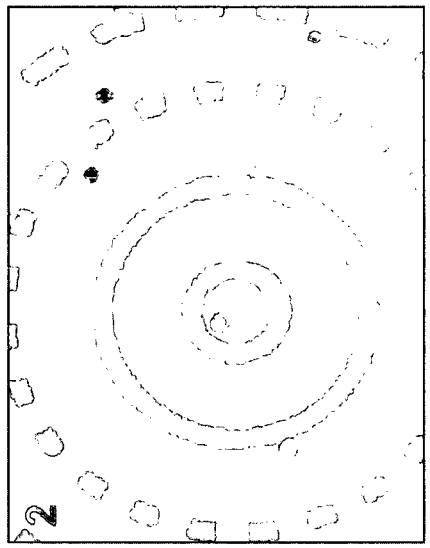
FIGS. 4A-4D are images of optical sorting of live and dead cells using the OET according to an aspect of the present invention.
Figure 4B:
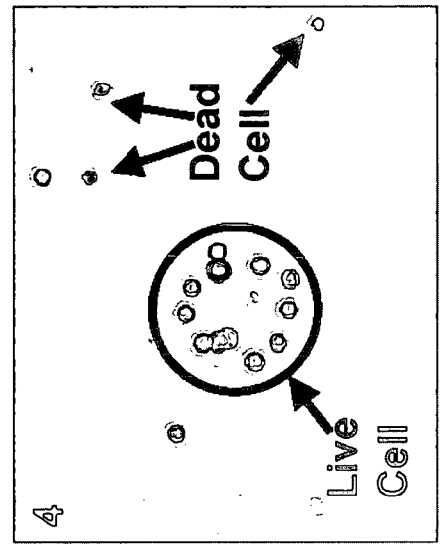
Figure 4C:
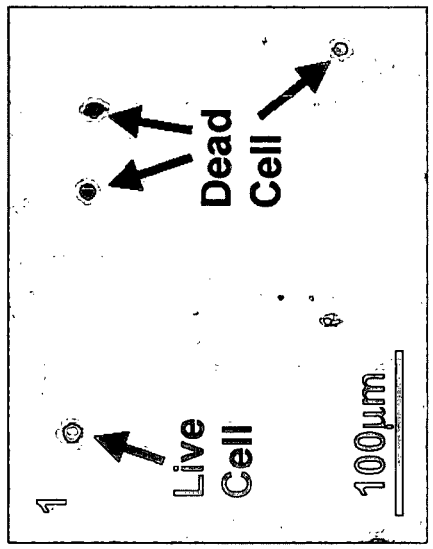
Figure 4D:
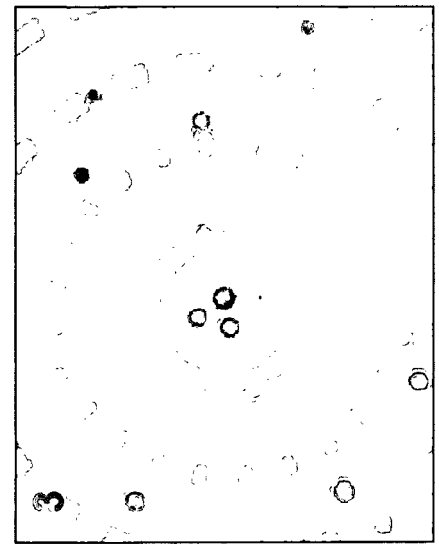

FIG. 3D shows a distribution of particle position in the middle of the sorter (marked by a white bar) after the particles have passed through the sorter 43 times. The standard variations of trace broadening are 0.5 µm for the 10 µm bead, and 0.15 µm for the 24 µm bead. The magnitude of the DEP force is proportional to the particle volume. The larger particles exhibit tighter confinement in the optically patterned DEP cages during transport.

FIG. 4A through FIG. 4D illustrate by way of example the sorting of biological cells according to their characteristics. According to this example embodiment, the living cells are subject to positive OET, trapping them in the bright areas, and pulling the live cells into the center of the pattern. The dead cells (i.e., stained with Trypan Blue dye) leak out through the dark gaps and are not collected. By exploiting the dielectric differences between different particles or cells, the DEP techniques described herein have been used to discriminate and sort biological cells with differences in membrane properties (e.g., permeability, capacitance, conductivity, and so forth), internal conductivity, and cell sizes. It should be appreciated that these techniques can be extended to other particle or cell characteristics. The OET technique not only inherits these DEP advantages but also provides the capability of addressing each individual cell.

The selective concentration of live human B cells is demonstrated from a mixture of live and dead cells in FIG. 4A through FIG. 4D. The cells are suspended in an isotonic buffer medium of 8.5% sucrose and 0.3% dextrose, mixed with a solution of 0.4% Trypan Blue dye to check the cell viability, resulting in a conductivity of 10 mS/m. The applied AC signal is 14$V_{PP}$ at a frequency of 120 kHz. The cell membranes of live cells are selectively permeable and can maintain an ion concentration differential between the intracellular and extracellular environments. By contrast the dead cells are unable to maintain this differential ionic concentration difference. So, then dead cells are suspended in a medium with a low ion concentration, the ions inside the cell membrane are diluted through ion diffusion, which results in a difference between the dielectric properties of live and dead cells. Live cells experience positive OET, and are collected in the center of the shrinking optical ring pattern by attraction to the illuminated region, while dead cells experience negative OET and are not collected.

Single cell analysis is an important technique to comprehend many biological mechanisms since it is capable of determining the response spectrum of each individual cell under stimulation. A new single cell and particle manipulation technique has been demonstrated according to the invention which has enabled manipulating a large number of single cells and particles in parallel using direct incoherent optical images. By programming the projected optical patterns, multi-step diagnostic protocols can be achieved by combining multiple functions such as transporting, sorting, recycling, and separating on a planar amorphous silicon-coated glass slide. In addition to biological applications, the high resolution electric field patterned on an OET surface can also serve as a dynamic template to guide the crystallization of colloidal structures.

2. Optoelectronic Tweezers.

The optoelectronic tweezers (OET) of the present invention are designed for cell and microparticle manipulation using optical control to permit functions such as cell trapping, collecting, transporting, and sorting of cells and microparticles by using sequentially projected images controlled by a spatial light modulator (microdisplay or DMD mirrors). Since the optical actuating power is as low as 1 mW, our invention permits the optical manipulation using a lightly focused incoherent light source and a direct image projection system. The system provides substantially increased optical manipulating area and allows the creation of complex optical patterns and thus more optical manipulation functions.

Figure 5:
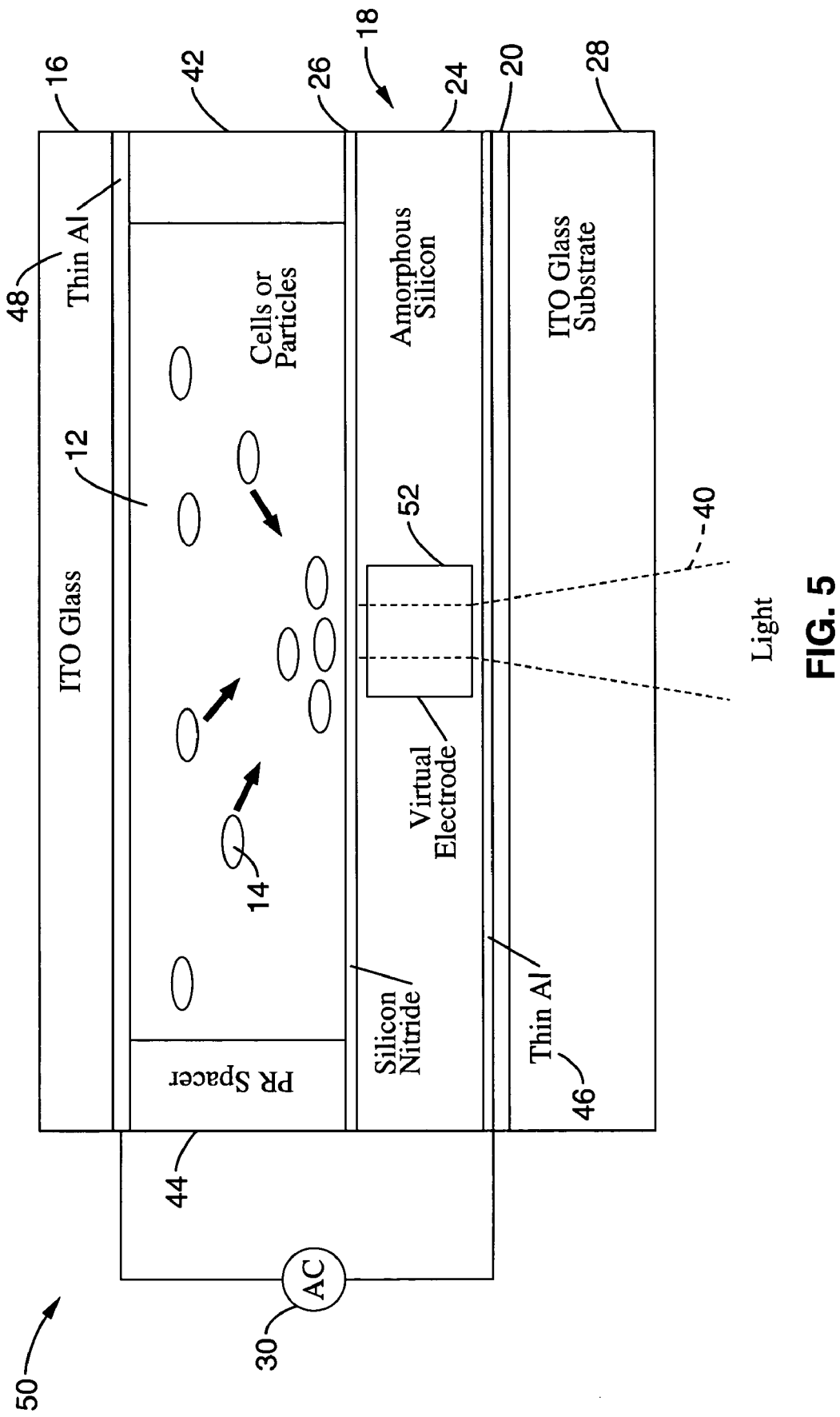
FIG. 5 is a schematic of an OET device according to an aspect of the present invention, showing the use of light-defined virtual electrodes which generate non-uniform electric fields in the liquid layer.

FIG. 5 is a schematic example of the structure of an OET device 50 according to another embodiment of the invention. The example OET shown includes spacers 44, 46 defining the horizontal extent of the liquid cell structure and separating opposing surfaces 16, 18. An AC bias may be applied across the top and bottom layers while optical patterns are imaged on a photosensitive surface within the lower layer 18. In a preferred embodiment the device comprises two opposing surfaces with a top surface having a transparent layer 16 with a thin conductive layer 44 (i.e., aluminum) on an interior surface and a bottom layer 18 with photosensitive surface 24. When the light is illuminated on the photosensitive surface, such as comprising a layer of amorphous silicon, it creates a light defined virtual electrode 52 which generates a nonuniform electric field in the liquid layer 12. The cells or particles nearby the virtual electrode are manipulated by the electrostatic force.

Figure 6:
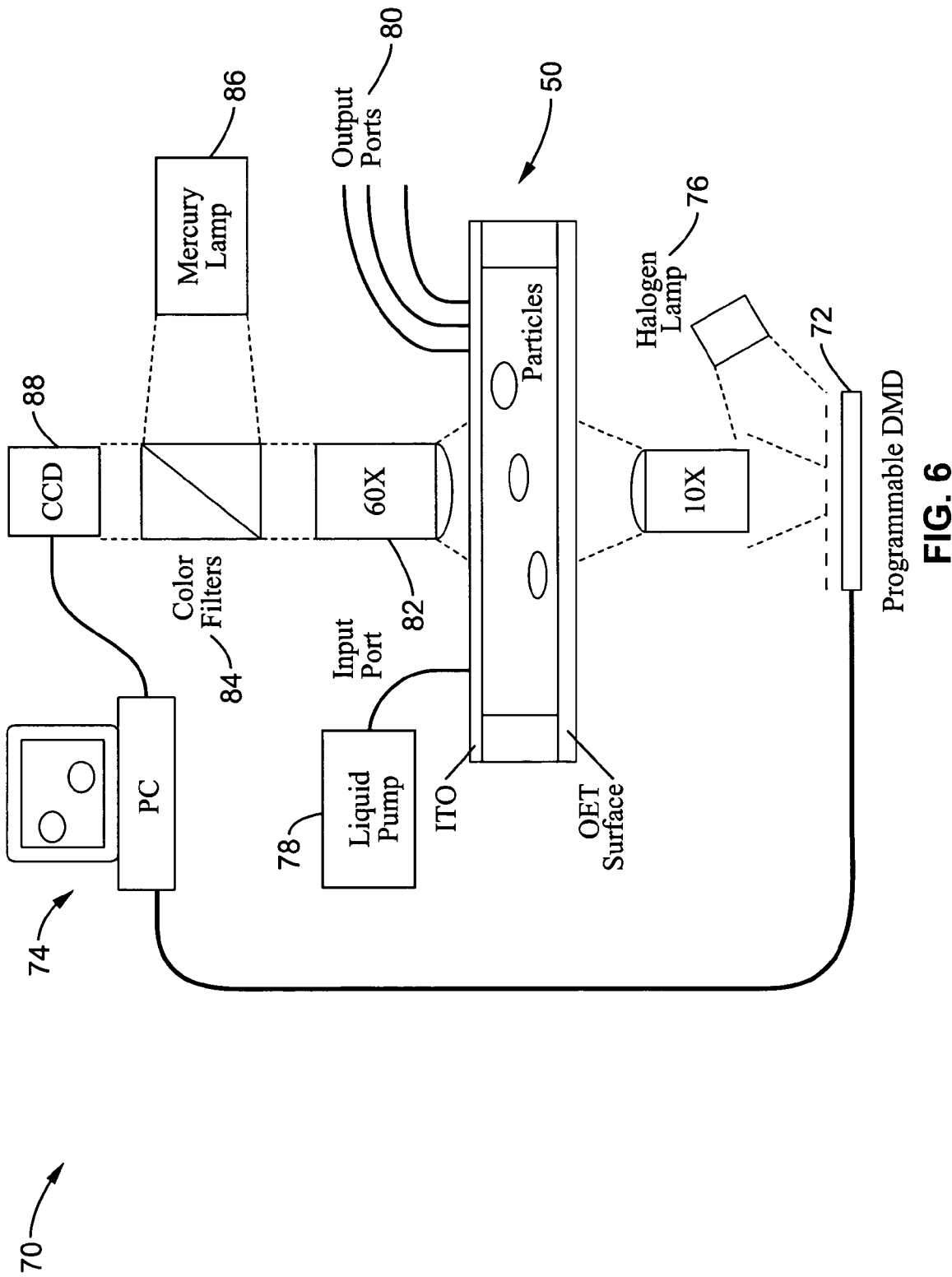
FIG. 6 is a block diagram of an OET-based cell manipulation system according to an aspect of the present invention, showing the use of a programmable spatial light modulator for generating the desired optical image.

FIG. 6 illustrates the OET of FIG. 5 within a cell manipulation system 70. A programmable spatial light modulator 72, such as a programmable DMD, is used to generate the required optical image controlled by a processing means 74, such as a PC. The optical image is projected onto the OET device, for example by reflecting light generated by a light source, such as halogen lamp 76, to create virtual electrodes within the structure for cell manipulation.

The OET devices can be operated with or without pumps or channels depending on the desired applications. Optional liquid pump 78 and output ports 80 can be utilized for moving a liquid along with particles or cells through the OET, or to change the conditions of the OET.

The motion of the cells is captured by an imaging means 88, such as a camera (i.e., charge coupled device (CCD)) with microscopic focus, which provides a feedback signal for further processing. In one mode of the invention a magnification lens system 82 is coupled through a combination of color filters and beamsplitter 84 and a light source 86 (i.e., mercury lamp) to allow images to be captured by computer 74.

When an optical image is projected onto the photosensitive surface, it creates a light patterned virtual electrode as shown in FIG. 5. This virtual electrode generates an electric field around it for manipulating the cells and particles through electrostatic force. The electric field patterns generated by the optical patterned electrode can have any kind of shape depending on the image projected. It can form an electric field cage to capture a single cell, or cell groups, or form an electric field channel to guide cells. Since those virtual electrodes are all optically patterned, they are fully programmable and reconfigurable. Optical manipulation functions such as cell transport, cell collecting and cell sorting can be achieved simultaneously on a single chip.

The exemplary OET device is particularly well-suited for applications in cell manipulation at both multi-cell and single cell levels. Liquid containing cells (or particles) are first sandwiched between the two surfaces of the OET. The optical images to be used are generated in the computer and then loaded for the spatial light modulator, which is illuminated with either a coherent or incoherent light source as shown in FIG. 6. The image is then preferably projected onto the OET device through an objective lens to create the optical patterned virtual electrodes. The response of the cells or the particles can be captured by an imaging means (i.e., camera) as a feedback signal for the computer to generate a new optical pattern required for the optical manipulation.

The microscopic imaging means coupled to the OET is preferably configured with recognition algorithms which provide information that allows image patterns to be created based upon the number, characteristics, and position of the particles, and/or cells, retained within the OET. For example this recognition algorithm can be utilized for determining particles and/or cells of specific size ranges, of specific colors and textures, or other directly detectable characteristics such as colors, shape, texture, conductivity, permeability, capacitance, motility, and so forth. The imaging system is also preferably configured for detecting indirect characteristics such as can be inferred from registering the response of particles, and/or cells, to environmental changes (e.g., aqueous solution changes, irradiation, temperature, pH, and so forth), or to interaction between the particle, and/or cell, and other particles, cells, and/or structures within the OET.

It will be appreciated that characteristics of particles, or more typically cells, can be determined by microscopically detecting response to changes in the environment, such as a shift in color, shape, texture, and so forth of a particle or cell in response to a temperature change, irradiation change, chemical characteristics change of the surrounding liquid, interaction with other particles and/or cells, and so forth. The microscopic imaging means can be configured to store information for each particle, or cell, in its field of view and to classify characteristics in response to correlating detected changes in response to changes in the environment. The microscopic imaging means can retain the information about each particle, or cell, despite its movement within the OET. In this way the present invention can be implemented to perform a wide range of particle and cell sorting, separation, classification, concentration, assembly, and other desired objects of manipulation.

The OET device can also be integrated with pumps and channel structures to provide for continuous optical manipulation. Furthermore, the OET device can be combined with continuous optical electrowetting (COEW) or conventional fixed electrode DEP techniques to address specific applications suited to a hybrid approach.

It should be appreciated that the present invention provides major improvements to the art with respect to the OET structure and in the utilization of photoconductive material. The OET device of the invention can be comprised of substantially featureless layers which do not require photolithography masking for fabrication, wherein fabrication cost factors are substantially reduced. In addition, it should be appreciated that low cost amorphous silicon is preferably utilized as the photoconductive layer, while also providing the benefits of low dark conductivity, high photosensitivity and short electron diffusion lengths. It should be appreciated that aside from amorphous silicon, other materials with similar electrical and optical properties can also be utilized. In addition, alternate embodiments can be providing by using other mechanisms and forms of photoresponsivity, such as using a phototransistor in place of the photoconductor structure.

The properties of the OET invention provide for optical manipulation at very low optical power levels (i.e., on the order of 1 mW) and sub-micron resolution of virtual electrode and also permits optical manipulation with the OET using an incoherent light source. It will be appreciated that conventional OET devices rely on the use of coherent light sources, as dictated by their structures.

The OET device of the present invention has been described and can be used for a variety of applications, such as particle trapping, collecting, multi-addressing, sorting on both microscopic particles and live cells. The OET device of the invention allows for parallel optical manipulation of cells on both single and multi-cell levels using reconfigurable optical patterns from a direct image projection system. No pumps, no microchannels and no valves are required to handle cells in microfluidic environment. It is contemplated that the use of the inventive OET device and methods described herein will provide a significant step forward in the field of particle manipulation, and in particular the manipulation of cellular particles.

3. Dynamic DMD-Driven Optoelectronics Tweezers for Particle Manipulation.

The ability to move and sort single cells is highly sought after in the biomedical and biological community. Optical tweezers, and dynamic holographic optical tweezers (HOT) arrays have provided a means of performing individual cell manipulation, but require high optical power levels (approximately 1 $\mu W$-100 $\mu W$) and have a small trap area (<1 $\mu m$). Optoelectronics tweezers (OET) provides a method of cell manipulation which overcomes the shortcomings of optical tweezers. It requires very low optical power (i.e., on the order of microwatts), which opens up the possibility of using incoherent light source and direct optical imaging to pattern the traps.

Previously, we had demonstrated OET manipulation of microscopic latex spheres and live *E. coli* cells using a single laser beam. A spatial light modulator can be used to generate multiple OET traps and novel patterns such as line and ring cages. In this paper, we report on novel particle cages capable of trapping and moving micro-particles by using a digital micromirror device (DMD) to project dynamic images onto our OET device, via a standard multimedia projector. It will be appreciated that this aspect of the invention demonstrates microscopic particle manipulation using a non-coherent light source, which should provide numerous benefits within a number of applications.

Figure 7A:
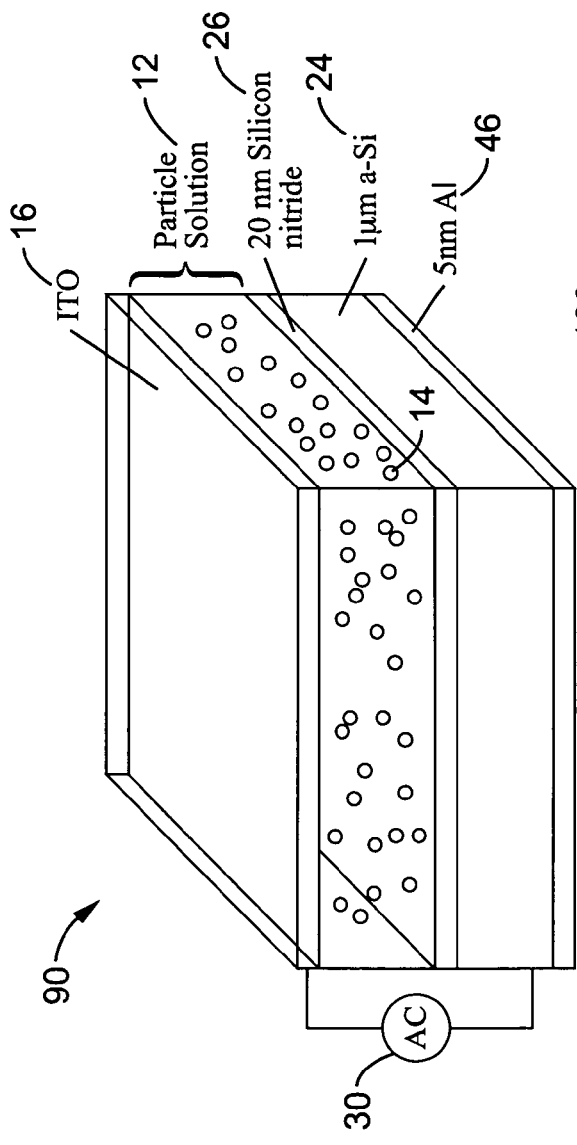
FIG. 7A is a perspective view of OET device structure according to an aspect of the present invention, showing particles retained in solution between a first layer and an optically responsive second layer.
Figure 7B:
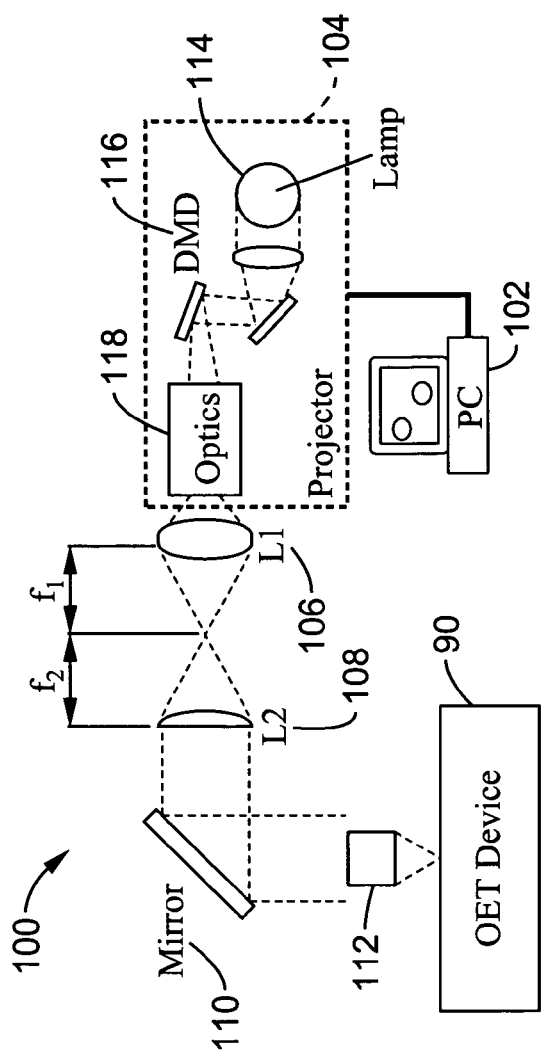
FIG. 7B is a schematic of an experimental OET setup according to an aspect of the present invention, showing the OET device of FIG. 7A receiving a modulated and directed light source.

FIG. 7A illustrates an example embodiment 90 of an optoelectronic tweezers according to the invention which is based on the principle of optically-induced dielectrophoresis. A buffer solution 12, sandwiched between the nitride layer and the indium-tin-oxide (ITO) top layer, contains the particles 14 of interest. In operation a light source is focused onto photoresponsive layer 24, such as comprising an AC-biased amorphous silicon (a-Si) photoconductive substrate layer of the OET device. In the dark, the a-Si is highly resistive, however, as the photoconductive layer is illuminated, the conductivity of the a-Si is greatly increased, due to photogenerated charge carriers, to create a localized virtual electrode, and generate a non-uniform electric field in the buffer solution. Dielectrophoretic (DEP) forces result from the nonuniformity of the electric field. These forces are either positive (particles attracted to electric field maxima) or negative (particles attracted to electric field minima), depending upon the dielectric properties of the particle and the media and the bias frequency. FIG. 7B illustrates an experimental setup for the OET material shown in FIG. 7A.

Figure 8:
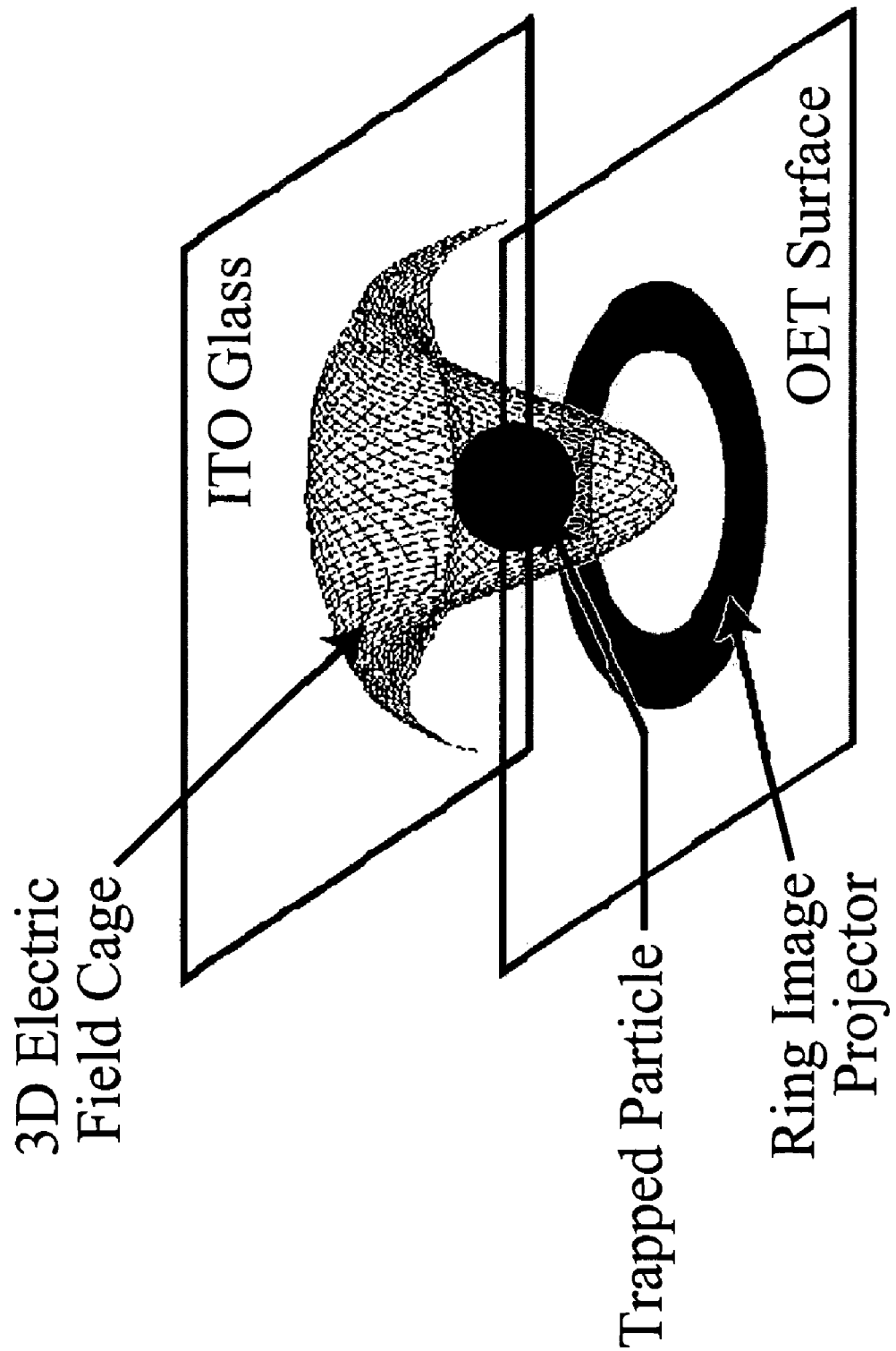
FIG. 8 is a 3-D graph of electric-field distribution for a single particle ring trap according to an aspect of the present invention.

FIG. 8 depicts the spatial electric field distribution resulting from a ring pattern projected onto the OET surface which can be configured to form a single-particle trap. Negative DEP forces hold a particle in the center of the light ring, as this corresponds to a local electric field minima. Particles outside the ring are repelled by the same forces.

Considering in detail the experimental setup 100 shown in FIG. 7B, shown by way of example, a computer 102 (i.e., a personal computer (PC)) outputs image signals to an InFocus® LP335 DMD-based projector 104 used as both the light source 114 (i.e., having a 120-W 1000-ANSI lumen high-pressure mercury lamp) and as the DMD driver circuit interface 116. The DMD, such as comprising an array of MEMS mirrors, forms an image corresponding to the output of the external monitor port of the PC. Light at the output of the projection lens was collected, collimated, and directed by way example with optics 118, lenses 106, 108, mirror 110 into an objective lens 112 (i.e., 10×) onto OET device 90. The objective focused the beam into the buffer solution 12 with a conductivity of 0.1 mS/m, sandwiched between the ITO top layer and photoconductive bottom layer. The photoconductive layer was situated on the stage of a Nikon® TE2000E inverted microscope. Observations were made via a CCD camera coupled into the inverted microscope.

Figure 9A:
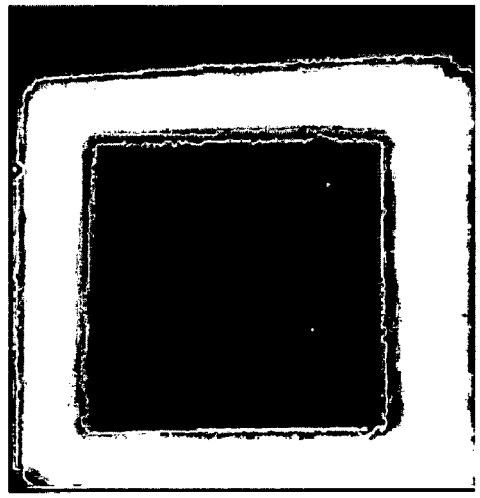
FIGS. 9A-9C are images of particle manipulation according to an aspect of the present invention, shown using a dynamic line cage with two angle sections (forming a square in FIG. 9A) which contain the particles in successively smaller regions.
Figure 9B:
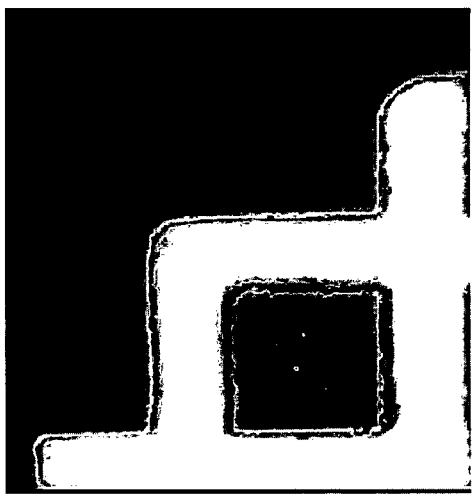
Figure 9C:
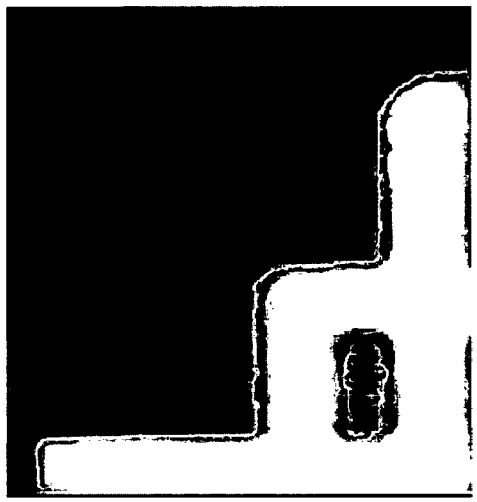
Figure 9D:
FIGS. 9D-9F are images of particle trapping according to an aspect of the present invention, showing trapping and moving a single particle while repelling particles outside of the selection area (ring).
Figure 9E:
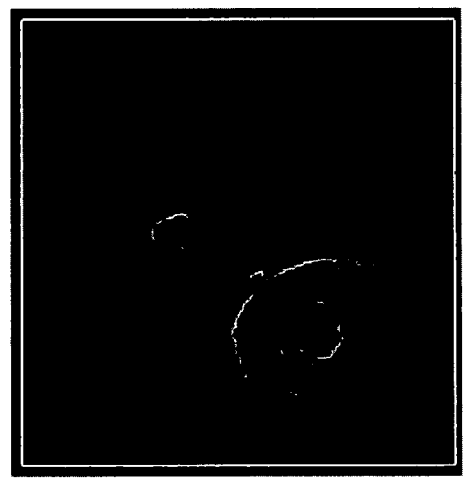
Figure 9F:
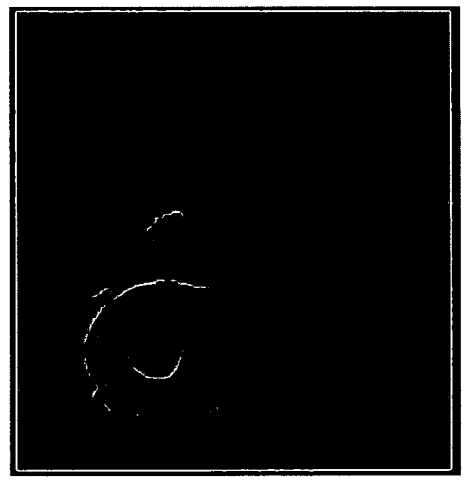

FIGS. 9A-9F depict images of particle caging and trapping according to aspects of the present invention. The images in these figures were formed on the focal plane of the objective using an optical projector, such as standard presentation software (Microsoft PowerPoint) on a PC connected to the DMD projector. Negative DEP forces were observed on the 25 µm latex spheres in solution, at an AC bias of 19.5V and a frequency of 100 kHz. A variety of patterns were used to manipulate the particles, including dynamic line cages (FIGS. 9A-9C) and ring traps (FIGS. 9D-9F). Particle movement was observed to be approximately 40 µm/sec.

It should be appreciated that this aspect of the invention demonstrates manipulation of micron-sized particles using optically-induced dielectrophoresis from a non-coherent light source. Various dynamic light patterns were successfully used as particle traps and manipulators, moving 25 µm latex spheres at approximately 40 µm/sec in a 0.1 mS/m buffer solution.

4. Dynamic Array Manipulation of Particles Via Optoelectronic Tweezers.

Cellular-scale manipulation is an important tool in biological research, and technologies that have demonstrated the capability for such microscopic manipulation include optical tweezers and dielectrophoresis. Although optical tweezers afford very fine control of microparticles, the technique suffers from high optical power requirements. Dielectrophoresis has been demonstrated to trap particles as small as 14 nm. However, dielectrophoresis requires a static pattern of electrodes, and is not easily reconfigurable.

Accordingly, the present invention demonstrates another method of manipulating micrometer-scale objects using a technique of optically-induced dielectrophoresis, or optoelectronic tweezers. Using a laser to induce dielectrophoretic forces, the controlled movement of 25 µm latex particles, and *E. coli* bacteria has been demonstrated. This technique can be utilized at very low optical power levels, enabling the manipulation of particles and cells with an incoherent light source. The use of a spatial light modulator in the described optical system also allows for dynamic reconfiguration of particle traps, providing increased versatility in particle manipulation over conventional dielectrophoresis. The present invention describes novel manipulation aspects in which dynamic array manipulation of microparticles is performed using optoelectronic tweezers. The self-organization of particles into an array, and the formation of single particle arrays, are demonstrated and provide the capability to individually address each particle.

Dielectrophoresis (DEP) refers to the forces induced upon a particle in the presence of non-uniform electric fields, which are typically generated by a variety of electrode configurations. A particle within an electric field forms an induced dipole, which will experience a force due to the field gradient. The direction of the induced dielectrophoretic force is dependent upon the frequency of the electric field and the permittivity and conductivity of the particle and the surrounding medium. Positive DEP results in particle attraction to electric field maxima. In contrast, negative DEP causes particles to be repelled from field maxima. Applying an AC electric field thus allows the tuning of the type of DEP force induced on a particle, as well as negating any electrophoretic effects, or particle movement due to its surface charge.

The optoelectronic tweezers (OET) device according to this aspect of the invention enables optically induced dielectrophoresis. Unlike conventional DEP, no electrode pattern is required to introduce non-uniformities into an applied electric field; instead, a photoconductive layer is used to form virtual electrodes. Focusing incident light onto the photoconductor substantially increases its conductivity as compared to the dark areas, effectively creating an electrode in the illuminated area, analogous to the patterned electrodes in conventional DEP. In addition, the virtual electrodes used by OET are movable and reconfigurable, unlike the static electrodes of conventional DEP.

Figure 10A:
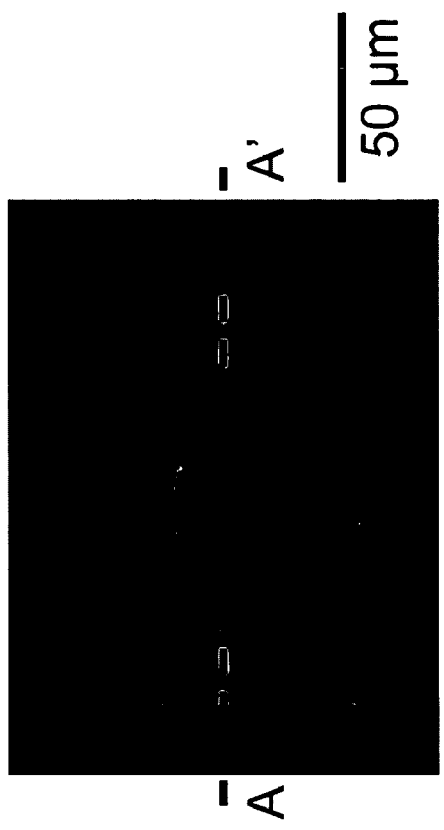
FIG. 10A is an image of a single-particle OET trap according to an aspect of the present invention, shown retaining a 45 μm polystyrene sphere.
Figure 10B:
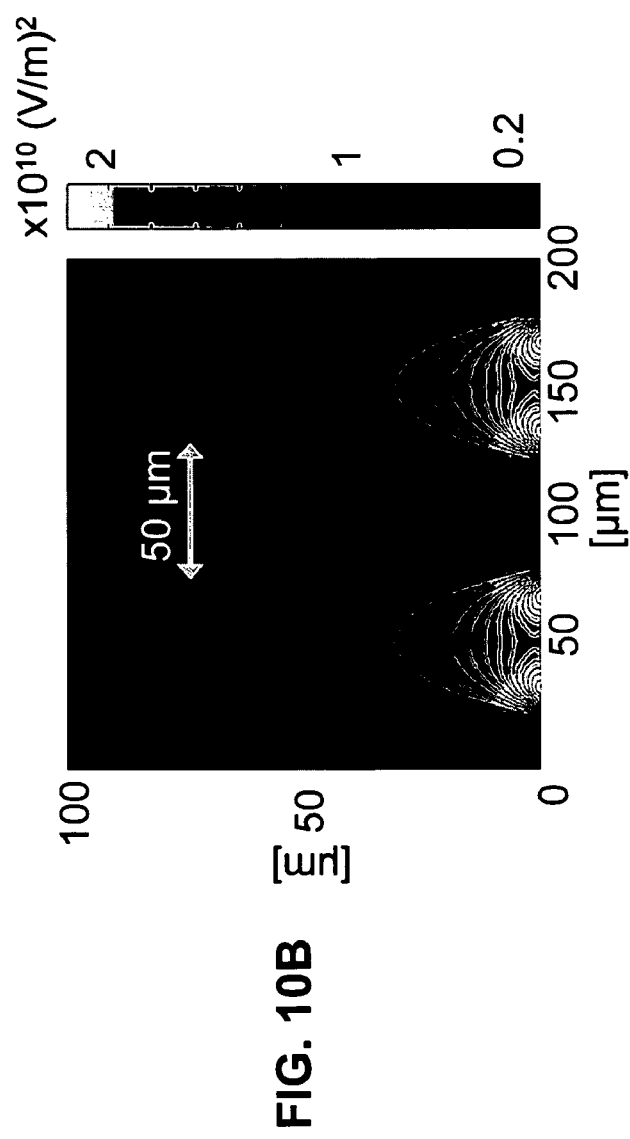
FIG. 10B is a graph of electric field distribution for the OET of FIG. 10A.

FIGS. 10A-10B illustrate aspects of an OET trap according to the present invention. In FIG. 10A, a single particle OET trap is shown with a 45 µm polystyrene sphere contained by optically-induced negative DEP. In FIG. 10B distribution of the square of the electric field is shown for the single particle trap in along the cross-section A-A' as shown in FIG. 10A. DEP force is proportional to the gradient of this distribution.

Shown by way of example, and not limitation, the single-particle rectangular trap of FIG. 10A has inner dimensions of approximately 70 µm by 50 µm. A sphere with a diameter of 45 µm is shown "captured" by the surrounding light "walls" which are approximately 25 µm wide. The corresponding cross-sectional distribution of the square of the electric field shows that width of the trap as experienced by the particle is approximately 50 µm, as DEP force depends on the gradient of this distribution as shown in FIG. 10B. If negative DEP forces are induced by the trap pattern, all particles outside the trap area will be repelled by the electric field maxima forming the trap perimeter. Any particle within the enclosed trap area will feel similar repulsive forces, however, these forces balance and trap the particle. Once a particle is contained within the rectangular pattern, the trap can be moved, transporting the particle to a desired location. Furthermore, multiple traps can be used as building blocks to form arrays of trapped particles, which can be arbitrarily arranged, and dynamically reconfigured.

The optical power required to induce DEP forces in the OET is much lower than that required when implementing optical tweezers, as the light energy provided for OET does not directly trap the particles. Early experiments using OET showed movement of 25 µm particles at 4.5 µm/sec with an optical power of 1 µW, corresponding to an incident power density of 440 mW/cm$^2$. In comparison, a 1 µm diameter optical tweezers trap, at a minimum trapping power of 1 mW, has an optical power density of 32 kW/cm$^2$.

The low optical power requirements of OET provide a number of system design advantages. Inexpensive incoherent light sources can be employed instead of lasers to provide the illumination necessary for OET. In addition, light patterns can be produced by imaging techniques (i.e., raster or vector based) rather than scanning techniques. Furthermore, with no need to focus all optical energy, a simple spatial light modulator can be utilized to pattern images, rather than utilizing the holographic techniques employed by optical tweezers arrays.

FIG. 11 illustrates an embodiment 90 of the optoelectronic tweezers device with a liquid buffer containing the particles of interest between the upper ITO glass layer and the lower photoconductive layer. To separate the top and bottom layers, 100 µm thick spacers (not shown) are utilized.

In demonstrating the OET device and methods herein the digital micromirror device (DMD) in a light projector was used to image the virtual electrodes. An embodiment of the optoelectronic tweezers device was formed by evaporating a 10 nm thick aluminum film onto a glass substrate to provide electrical contact. A 1 µm thick undoped amorphous silicon (a-Si) photoconductive layer was then deposited, for example by utilizing plasma-enhanced chemical vapor deposition. It should be appreciated that detailed fine-pitched features need not be created on the first and second retention layers, wherein detailed lithographic steps are not necessary. To protect the photoconductive film, a 20 nm thick silicon nitride layer is preferably deposited over the a-Si in this embodiment. It should be appreciated, however, that for some applications the device can be formed without a dielectric. The liquid buffer layer containing the particles of interest is sandwiched between this photoconductive device and the opposing surface, such as comprising indium-tin oxide (ITO) glass. An applied AC bias across the ITO and a-Si produces the electric field.

Amorphous silicon has a dark conductivity of about 0.01 µS/m to 1 µS/m. Thus, in the dark, the a-Si has a much lower conductivity than the liquid buffer (which has a conductivity of 10 mS/m), causing the majority of the voltage to drop across the silicon layer. Incident light focused onto the photoconductive layer substantially increases conductivity and creates a non-uniform electric field surrounding the illuminated area, as the majority of the voltage now drops across the liquid buffer layer. In this manner, the light incident on the OET device can pattern virtual electrodes for dielectrophoresis.

FIG. 12 illustrates by way of example an experimental setup 100 for OET 90. In this example embodiment, the image from a projector 104, such as an InFocus LP335, having mercury lamp 114, DMD 116, and focusing optics 118 is focused via optical elements 106, 108 and 110 into a 10× objective lens 112, and projected down onto OET device 90. Particle movement is observed on a microscopic imaging means 120, for example a Nikon TE2000U inverted microscope, coupled to computer 102.

A DMD-based projector (InFocus LP335) is shown used to display images drawn on a PC, via Microsoft PowerPoint software. The projector provides both the optical source (a 120 W, 1000-ANSI lumen high-pressure mercury lamp) and the DMD-to-PC interface. The output of the projector is collected, collimated, and directed into an objective lens (i.e., Olympus MSPlan10 10X with NA=0.30), projecting an image onto the OET device. The power at the projector output was measured to be approximately 600 mW.

Approximately 7% of this power is collected by the objective lens and focused onto the OET device. Therefore, the power of the light incident on the OET is 42 mW, corresponding to an intensity of 12 W/cm$^2$. The buffer solution comprises deionized water and KCL salt, mixed to obtain a conductivity of 10 mS/m. Polystyrene microspheres (45 µm and 20 µm) are mixed into the buffer solution, and sandwiched into the OET device.

FIG. 12 illustrates, by way of example, a optical setup embodiment 100 for this OET demonstration. Observation of the particles under test is performed preferably utilizing a microscopic imaging system 120, for example a Nikon TE2000U inverted microscope. A CCD camera attached to the observation port of the microscope recorded images and video of these demonstrations and tests. To produce the electric field necessary for DEP, an AC voltage of approximately 10V$_{PP}$ at 100 kHz (i.e., Agilent® 33120A) was applied across the top ITO surface and the bottom photoconductive surface of the OET device.

Figure 13B:
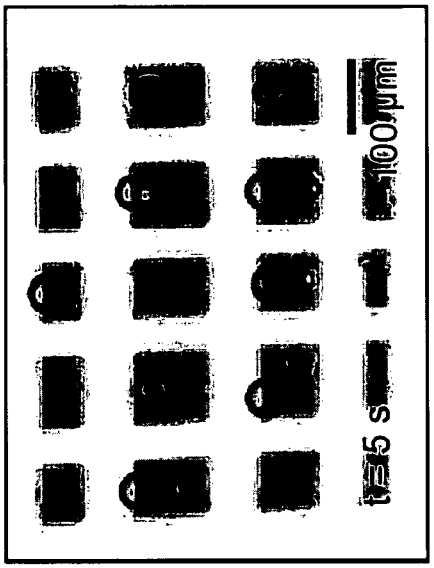
FIGS. 13A-13B are images of self-organization of microparticles into an array configuration according to an aspect of the present invention.
Figure 13A:
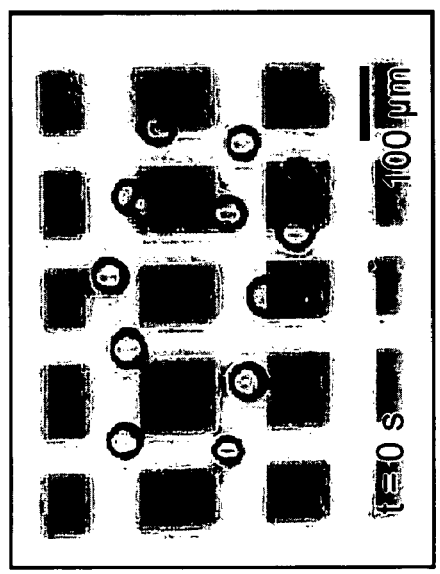

FIGS. 13A-13B illustrate self-organization of 45 µm polystyrene spheres into an array configuration. After the initial grid illumination shown in FIG. 13A, the randomly arranged particles move towards the dark areas via negative DEP. After five seconds, all particles are contained within the array cells as shown in FIG. 13B.

The self-organization of randomly distributed 45 kHz polystyrene spheres into an array (FIGS. 13A-13B) is demonstrated by directing a simple grid pattern of orthogonal horizontal and vertical lines, such as drawn in PowerPoint, which are projected onto the OET device. The pattern activates the optically-induced DEP, repelling particles from the illuminated areas due to negative DEP forces. This mechanism causes the self-organization of the particles once the grid pattern is illuminated; wherein particles are pushed into the non-illuminated cells. After a settling period, the particles are trapped within the array of cells.

Due to a large trap relative to the particle size, the initial self-organization may result in more than one particle per array cell as shown in FIG. 13B. In this array, the largest cells are 80 μm by 100 μm. It may be possible to form self-organizing arrays with a single particle per array cell by optimizing the dimensions of a single array cell trap, such that only one particle may fit into the potential well of the trap at any time.

Figure 14B:
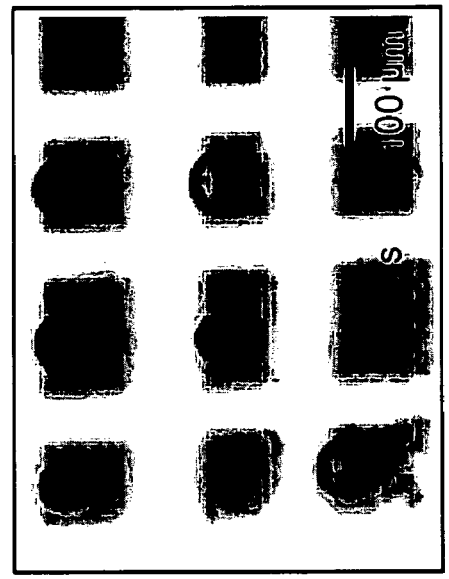
FIGS. 14A-14B are images of single-particle manipulation within an OET array according to an aspect of the present invention.
Figure 14A:
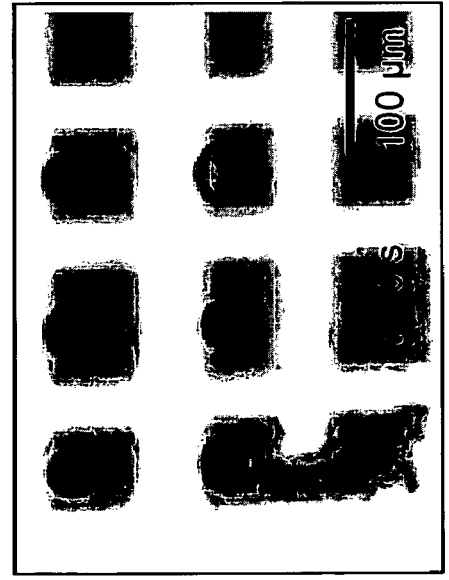

FIGS. 14A-14B illustrate examples of single-particle manipulation within the array. A particle in the lower-left side of the array is made to change its array by combining cells in FIG. 14A, the re-splitting the cell, moving the particle to the adjacent array position shown in FIG. 14B.

In addition, it was found that certain particles within the self organized array are able to escape when the array is moved around the image plane. This phenomenon occurs for the array cells that contain multiple particles. This occurrence, along with subsequent manipulation of the self-organized array in FIG. 13B, allowed us to obtain an array with a single particle per cell as shown in FIG. 14A. It should be noted that we were able to move the resulting array of single particles around the image plane at approximately 25 μm/sec.

Particles can be moved individually between adjacent cells, as illustrated in FIGS. 14A-14B. The adjacent cells are merged by first removing the dividing wall, and then re-separating the cells. All movement of the trap walls are controlled in real-time by the operator. To improve on the speed of this technique, a moving light wall can be used to facilitate the transportation of the particle between cells. This enables a single particle to be transferred to any cell of the array, using repeated transfers between adjacent cells.

Figure 15B:
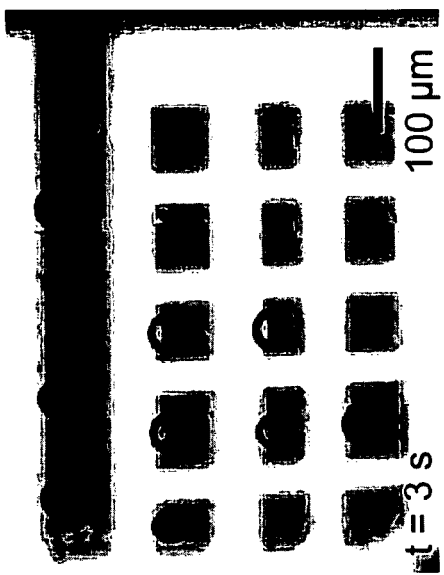
FIGS. 15A-15D are images of particle array flushing within an OET array according to an aspect of the present invention.
Figure 15D:
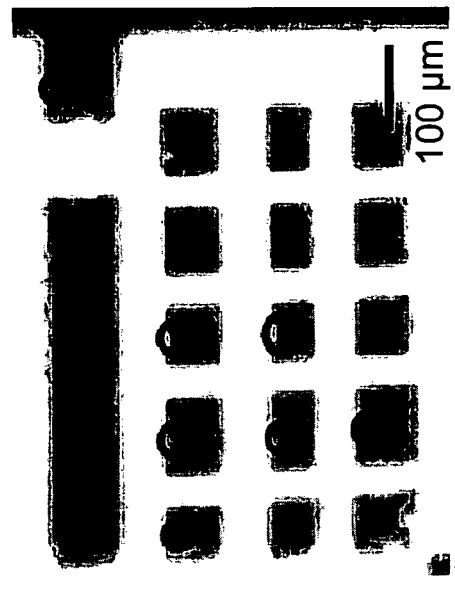
Figure 15A:
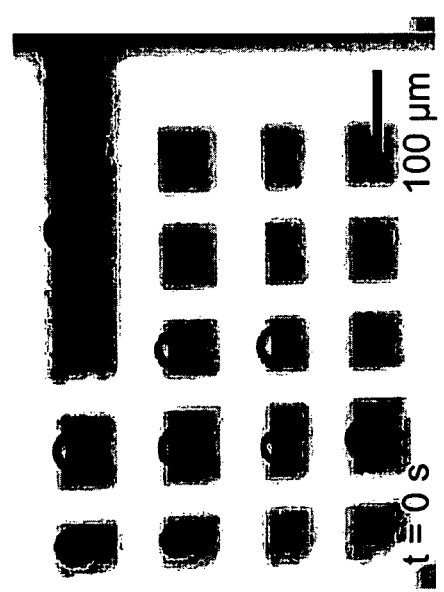
Figure 15C:
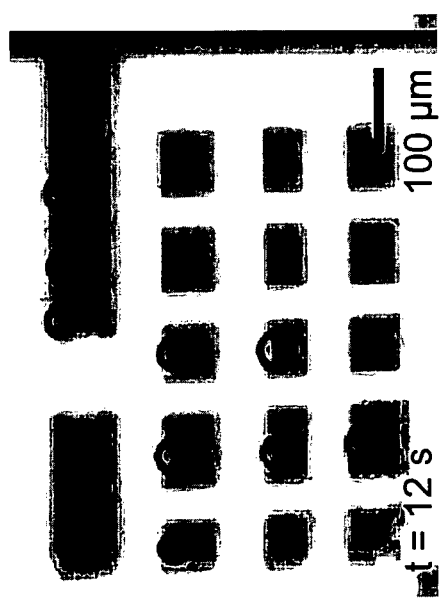

FIGS. 15A-15D illustrate examples of flushing an array row to remove undesired particles from the array. First, the walls of the cells in the row to be flushed are removed as shown in the top row of FIG. 15A. The particles are no longer bounded in the lateral direction as shown in FIG. 15B. An operator-controlled light bar is then used to push the particles out of the array as shown in FIG. 15C and FIG. 15D.

Since the patterns for manipulating the particles in the array are created dynamically by optical illumination, a wide variety of operations can be performed by simple software programming. For example, to flush the particles in a single row of the array, we remove the dividing walls of that row and use a moving wall to sweep out the particles (FIGS. 15A-15D).

In addition to self-organizing behavior, arrays can be formed from multiple single-particle traps. Each randomly positioned particle is first contained within a square trap. This is performed by drawing a rectangle around each particle in PowerPoint. The multiple traps can then be positioned to form an array of individually addressable cells.

Figure 16:
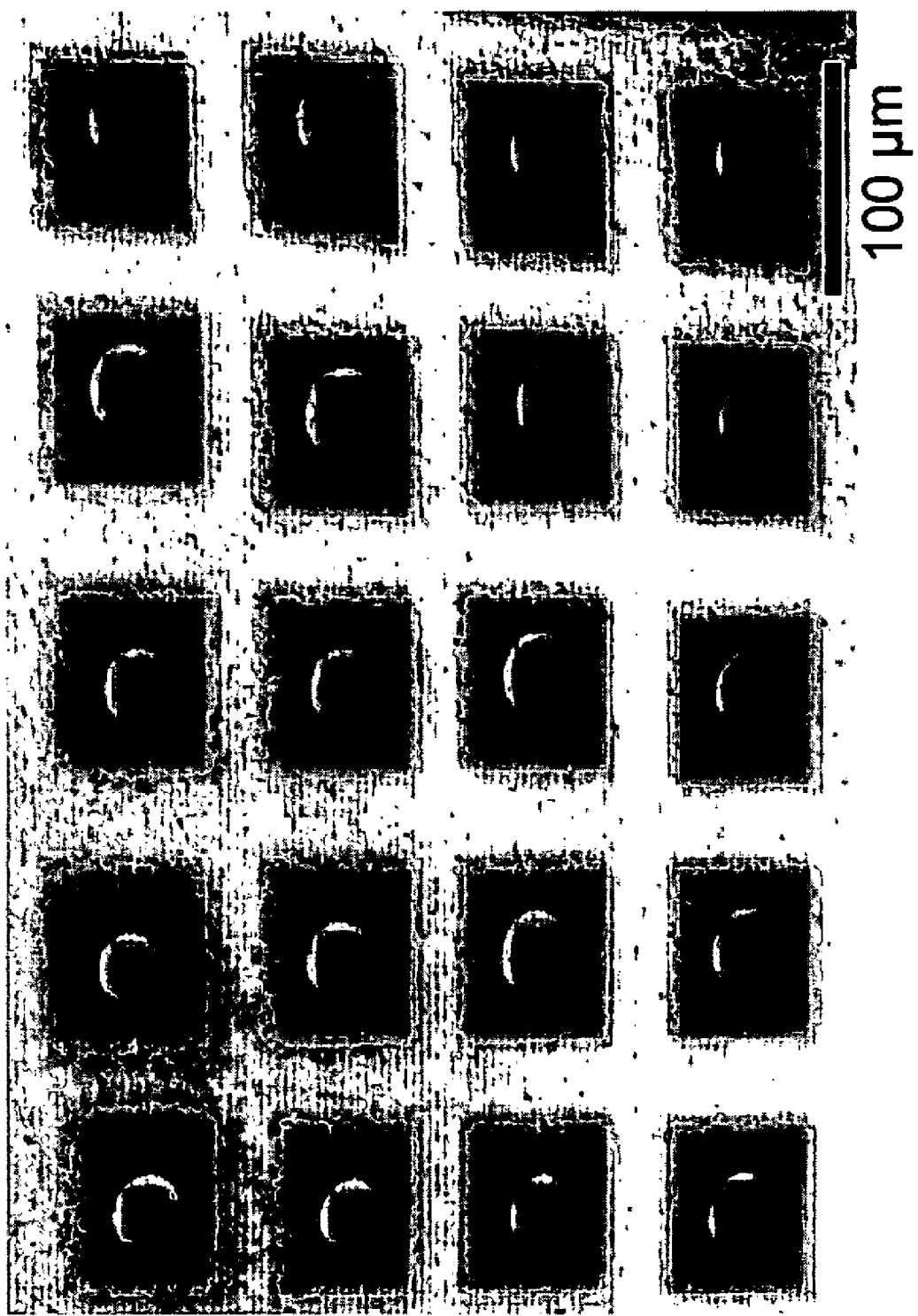
FIG. 16 is an image of an array of single particles trapped in an OET array according to an aspect of the present invention.
Figure 17A:
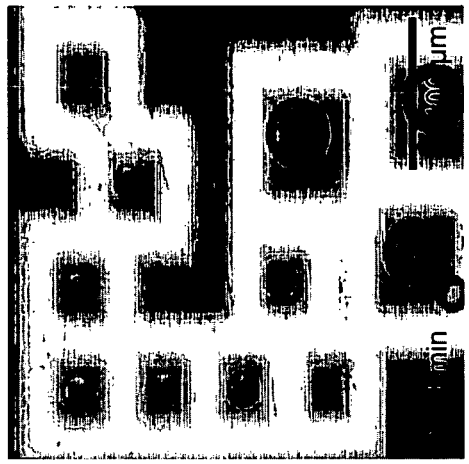
FIGS. 17A-17D are images of dynamic rearrangement of differently sized particles according to an aspect of the present invention.
Figure 17B:
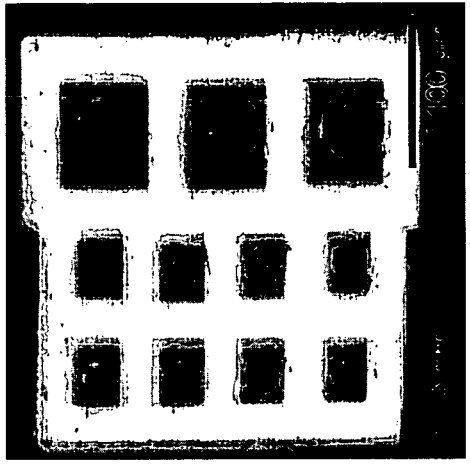
Figure 17C:
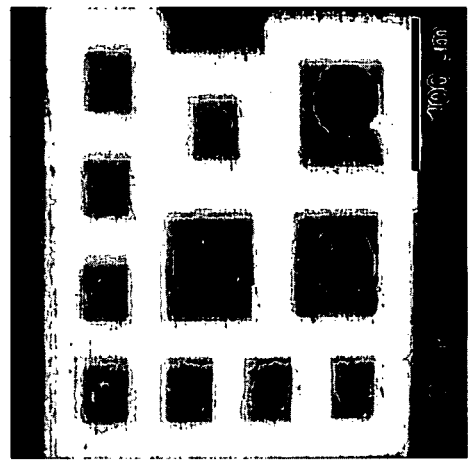
Figure 17D:
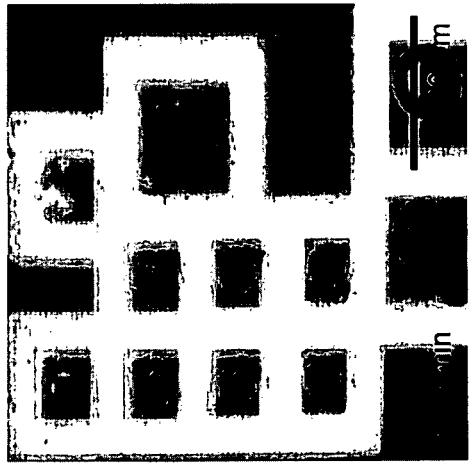
Figure 19B:
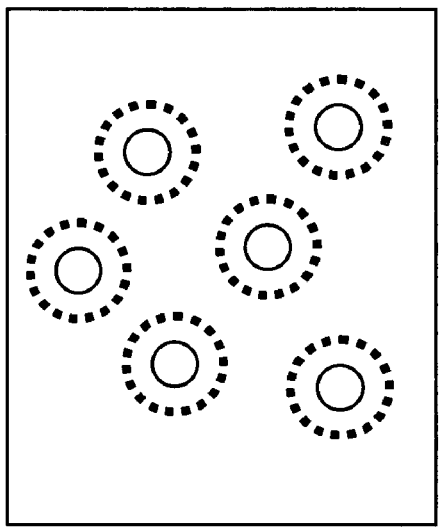
FIGS. 19A-19D is an illustration of steps according to an aspect of the present invention for arranging particles into any desired pattern.
Figure 19D:
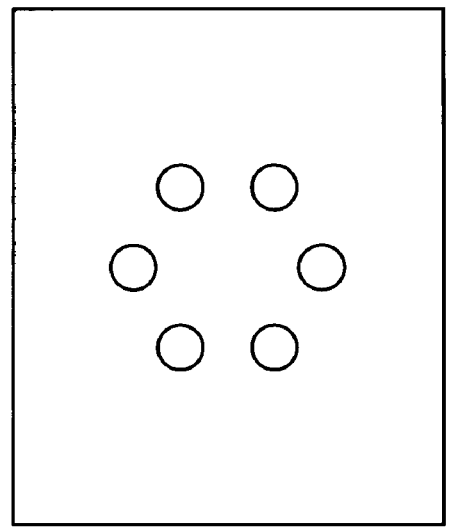
Figure 19A:
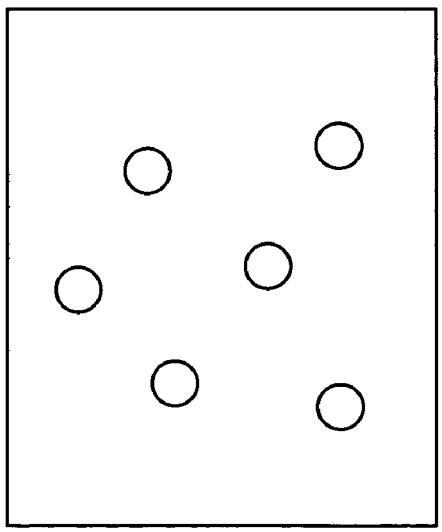
Figure 19C:
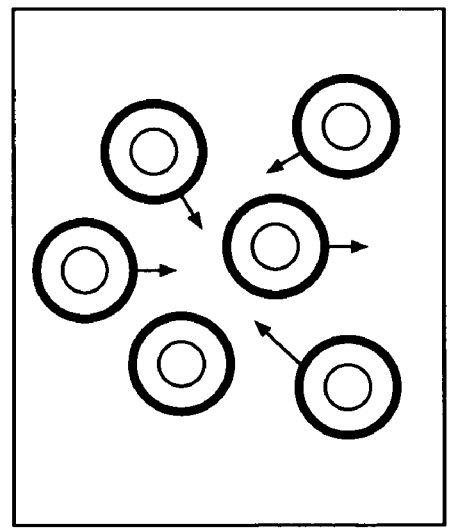

FIG. 16 illustrates an example of an array of single particles, formed from multiple single particle square traps. Each particle is individually addressable. The time required to form this array of 20 particles was 3 minutes. Using this technique, we are able to form a 4×5 array of single particle traps as shown in FIG. 16. Though the operation was performed manually, it can potentially be automated by combining OET with a vision system. Biological applications of such an array include studies on single-cell behavior and interaction. Since each cell of the array is an independent single particle trap, the array has the capability of being dynamically rearranged.

FIGS. 17A-17D illustrate an example of dynamic rearrangement of an array containing both 45 μm and 20 μm particles. An array is rearranged by moving individual cells into a desired configuration. Total rearrangement time for the embodiments was three minutes. The spheres are reorganized under operator control in the images shown in FIGS. 17A-17D, which demonstrates the addressability of each particle trap, as well as the dynamic nature of the OET patterns.

Movement of a single 45 μm sphere in response to negative DEP provides a maximum velocity of approximately 35 μm/sec. This corresponds to an estimated force of 15 pN, based upon Stoke's Law. The maximum velocity of a 20-particle array is limited to approximately 25 μm/sec. Thus, the minimum holding force of each individual array cell is 10 pN. This force is less than that experienced by a single 45 μm particle, probably due to slight nonuniformities in image sharpness over the entire array area. The more defocused areas will have less of an electric field gradient, and a correspondingly lower DEP force. Thus, this 10 pN force reflects the minimum trapping force of all of the array cells.

The forces attained in these experiments, using an optical power density of 12 W/cm$^2$, are in rough agreement with our earlier results using a 632 nm laser light source. Our earlier data suggests that the optical power density necessary to achieve a force of 15 pN is 6.6 W/cm$^2$. The difference between this predicted power density requirement and our experimental findings can be attributed to losses through the additional optics needed for our current experiment.

These results compare favorably to other microparticle manipulation techniques. Conventional dielectrophoresis uses static electrode patterns, and is thus not reconfigurable. In addition, our device is less expensive to produce, as no photolithographic steps are needed. Addressable DEP arrays have also been demonstrated using CMOS technology, but these devices are expensive to produce, and the minimum electrode size is limited by the required CMOS circuits. Both conventional DEP and optical tweezers are capable of manipulating particles a few nanometers in diameter. The minimum size of the virtual electrode in OET is limited by the 115 nm ambipolar diffusion length of the a-Si. The OET can operate over a large area (i.e., approximately 1×1 mm), which is much greater than the 20 μm×20 μm area for optical tweezers.

Though holographic tweezers can generate multiple traps, direct imaging using a DMD is more versatile. It can generate any arbitrary pattern with high contrast ratio. No computation is required to generate the desired pattern. Furthermore, OET can induce repulsive forces on transparent dielectric particles such as biological cells, and form cell cages, which is not possible with optical tweezers. On the other hand, optical tweezers traps are three-dimensional, whereas our trap patterns are limited to two dimensions. Utilization of the present invention generally requires being more selective in the choice of buffer solutions, because the conductivity of the solution plays an important role in the DEP phenomenon.

The self-organizing of 45 μm polystyrene particles into an array, and the creation of an array from multiple single particle traps utilizing optoelectronics tweezers have been demonstrated with the present invention. Single particle movement within the array has been demonstrated, showing the ability to address individual array cells. Movement of single 45 μm polystyrene spheres was measured to be 35 μm/sec (a force of 15 pN). Movement of a 20-particle array was performed at 25 μm/sec (a force of 10 pN). Such particle manipulation techniques have many applications to experiments with biological cells and microparticles.

5. Microvision-Activated Automatic Optical Manipulator for Microscopic Particles.

An embodiment of the present invention includes an automatic optical manipulator that integrates microvision-based pattern recognition and optoelectronic tweezers (OET) for processing microscopic particles. This system automatically recognizes the positions and sizes of randomly distributed particles and creates direct image patterns to trap and transport the selected particles to form a predetermined pattern. By integrating the OET with a programmable digital micromirror device display (DMD), we are able to generate 0.8 million pixels of virtual electrodes over an effective area of 1.3 mm×1 mm. Each virtual electrode is individually controllable for parallel manipulation of a large number of microscopic particles. Combining the automatic microvision analysis technology with the powerful optical manipulator, this system significantly increases functionality and reduces processing time for microparticle manipulation.

Tools for manipulating microscopic particles are important in the fields of cell biology and colloidal science. Optical tweezers and dielectrophoresis are two of the most widely used mechanisms for manipulating microparticles. Optical tweezers use direct optical forces to deflect the motion of microscopic particles. Optical tweezers are noninvasive and have high positioning accuracy. The use of holographic optical tweezers further extend the benefits to allow manipulating multiple particles. However, these techniques require very high optical power levels, and provides limited working area (<100 μm×100 μm) due to the need of tight focusing with high numerical aperture (N.A.) lenses. These factors limit the use of these forms of optical tweezers in large-scale parallel manipulation applications.

In contrast, dielectrophoresis (DEP) controls particle motion by subjecting particles to non-uniform electric fields. The technique provides high throughput and large working area, but requires a fixed electrode pattern for a given function. Programmable DEP cage array consisting of two-dimensional electrodes with integrated driving circuits has been demonstrated on a CMOS (complementary metal-oxide-semiconductor) chip. However, the resolution is limited by the pitch of the electrode and the driving circuits of the unit cell, and the cost may prohibit its use as disposable devices.

FIGS. 18A-18B illustrate aspects of an example embodiment of an optical manipulation system. In FIG. 18A a schematic diagram is shown of an example embodiment 130 of a microvision-based automatic optical manipulation system. In FIG. 18B the structure of the OET device is shown.

According to the present invention a novel optoelectronic tweezers (OET) has been developed to address DEP forces on a photoconductive surface using optical beams. OET enables virtual electrode patterns to be created optically. The electrode size can be varied continuously by the optical spot size down to the diffraction limit of the objective lens. Because of the optoelectronic gain in the photoconductor, the required optical power density is five orders of magnitude lower than that of optical tweezers. This enables our method to use a digital optical project with incoherent light source to manipulate microparticles. The present invention describes the use of "light walls" to confine microparticles in virtual microfluidic channels and switch them by light pistons. Interactive manipulation of virtual DEP cage arrays has also been demonstrated by manually changing the optical patterns.

In this aspect of the invention automatic optical manipulator use is described by integrating the OET with a microvision-based analysis system. The microvision system automatically recognizes the particle positions and sizes, generates the desired trapping patterns, and calculates the moving paths of the particles. It enables close-loop control of trapping, transporting, and assembling a large number of particles in parallel.

The microvision based optical manipulation system 130 of FIG. 18A is constructed with OET device incorporating a microscopic imaging means and a mechanism for registering particle/cell characteristics and position.

Particle or cell movement is controlled by projecting light generated from source 114 reflected from DMD 116 through objective 112 onto OET 90. The light patterns are generated in response to the positioning and characteristics of the particles or cells as registered by a microscopic imaging means in combination with image analysis and pattern recognition algorithms. In this example the images are collected through lens 132 onto a CCD imager 134, and the data is processed to control the patterns of light being generated. The microscopic images, or image stream, is analyzed within an image analysis circuit and/or routine 136. The image data is then processed using pattern recognition circuits and/or routines 138. The recognition of actual patterns is performed in relation to the desired goal of the application, wherefrom subsequent patterns are generated by pattern generator circuit and/or routine 140, which is then converted by DMD circuit and/or routine 142 to control the operation of the programmable DMD device 116. It should be appreciated that this may be implemented in a number of alternative ways without departing from the teachings of the present invention, such as using various imaging sources, microscopic imaging, and different techniques for detecting, analyzing, and generating subsequent optical images onto the OET.

By way of example, this embodiment incorporates a Nikon inverted microscope 132, 134. A 150 W halogen lamp 114 illuminates on a programmable digital micromirror device (DMD) microdisplay 116. The DMD pattern is imaged onto the OET device through a 10× objective lens 112. The structure of OET device 150 is shown in FIG. 18B.

FIG. 18B illustrates another example OET embodiment comprising a top and bottom surface 16, 28, comprising such as indium-tin-oxide (ITO) glass and photosensitive layer 24, such as amorphous silicon, on the surface of the top and/or bottom layers. The liquid medium 12 containing the particles 14 are sandwiched between these two surfaces. The OET is biased by a single AC voltage source 30. Without light illumination, most of the voltage drops across the amorphous silicon layer 24 because its impedance is substantially higher than liquid layer 12. Under optical illumination, the conductivity of the amorphous Si 24 increases in the areas upon which the illumination is impinging by several orders of magnitude, shifting the voltage drop to the liquid layer. This light-induced virtual electrode thereby creates a non-uniform electric field 152, and the resulting DEP forces drive the particles of interest. The light-induced DEP force can be positive or negative, controlled by the frequency of the applied AC signal. Negative DEP force repels particles away from the high field region, and is preferable for single particle cage, which can be easily formed by a light wall around the particle. Positive DEP tends to attracts multiple particles. We have employed negative DEP force in our automatic optical manipulator experiments. The image on the OET device is captured by a CCD camera through the inverted microscope and sent to a computer for image processing.

Software according to the present invention analyzes the real time video frames and generates the corresponding optical patterns for trapping and moving the particles. These patterns are then transferred to the DMD, and our test setup allows direct control of individual pixels. The resolution of the projected optical image on the OET device is 1.3 μm, defined by the pixel size of the mirror (13 µm). The effective optical manipulation area on the OET is 1.3 mm×1 mm. By combining the DMD mirrors with the OET device, the silicon-coated glass is turned into a million-pixel optical manipulator.

FIGS. 19A-19D illustrate the process of automatically recognizing and arranging randomly distributed particles into a predetermined pattern. First, the images of the particles are captured and analyzed by the microvision system as in FIG. 19A, which identifies the positions and the sizes of all particles as in FIG. 19B. The software then generates a ring trap around each particle as in FIG. 19C. It also calculates the trajectories of the particles to reach their final positions as in FIG. 19D.

Figure 20A:
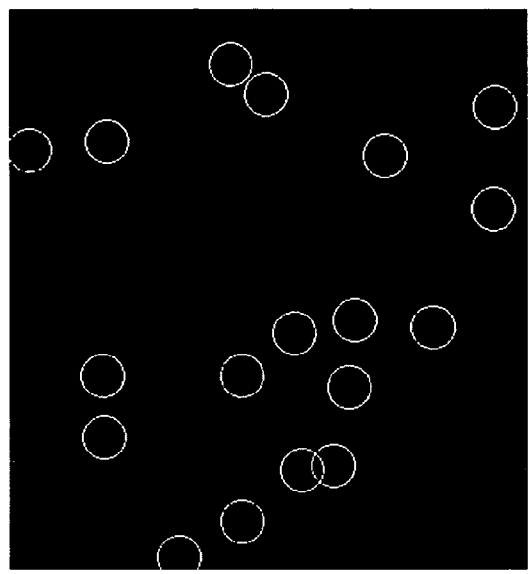
FIGS. 20A-20D are images from a particle recognition system and a graph of recognition percentage according to an aspect of the present invention.
Figure 20B:
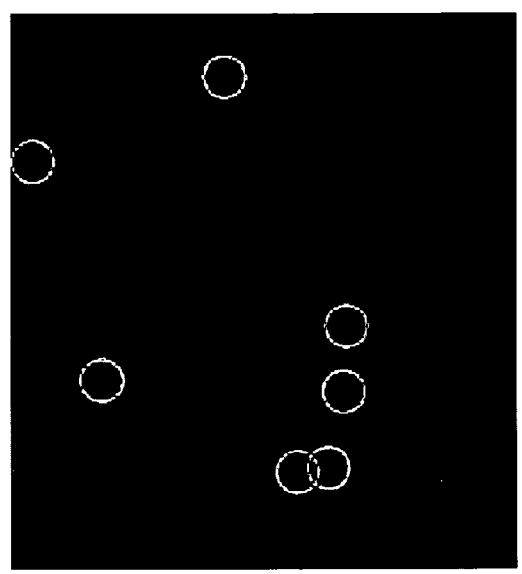
Figure 20C:
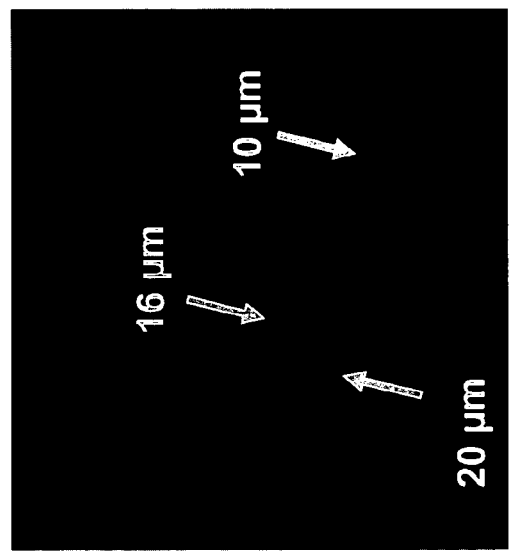
Figure 20D:
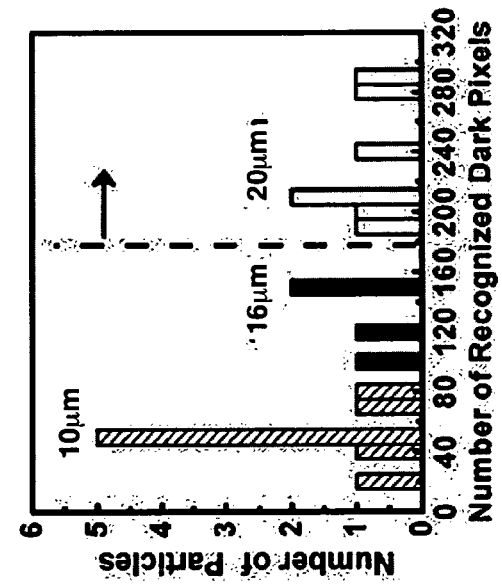

FIGS. 20A-20D illustrate by way of example test images for a particle recognition system. Polystyrene particles with three different sizes, 10 µm, 16 µm, and 20 µm, are mixed and randomly distributed in the liquid medium. In FIG. 20B, the microvision system recognizes the position of each particle and projects a ring mark on each particle. In FIG. 20C, the histogram showing the number of particles versus the number of recognized dark pixels in this test image. In FIG. 20D the largest particles are selectively picked up by setting a threshold for the dark pixels.

Particle recognition is achieved by using a dark-pixel recognition algorithm to scan through each pixel of the captured image. The brightness value and the position of each pixel are then recorded and calculated to determine the size of each particle and its center position. The brightness value of the pixels at the particle edge is smaller than that of the background and the color is darker too. By setting a threshold brightness value between the background and the particle edge, we can recognize the edge pixels of each particle. Averaging the x and y position data of the edge pixels of each particle, we can determine its position.

FIG. 20B shows the recognized particles marked by a white ring pattern generated by the microvision analysis system. The same algorithm also determines the size of each particle by counting the number of the recognized dark pixels.

FIG. 20C is a histogram of data showing the number of particles and the number of the dark pixels recognized for each particle on this image. As larger particles have more dark pixels than smaller ones, a threshold number can be set for the recognized pixels, as indicated by the dash line in the histogram figure, wherein the system can selectively register particles with certain sizes.

FIG. 20D depicts the seven largest beads (20 µm), by way of example, that are selected by setting a threshold number equal to 180. This recognition algorithm is used specifically for determining spherical particles with different sizes. Other algorithms can be developed to recognize particles with different colors, shapes, or textures.

Figure 21B:
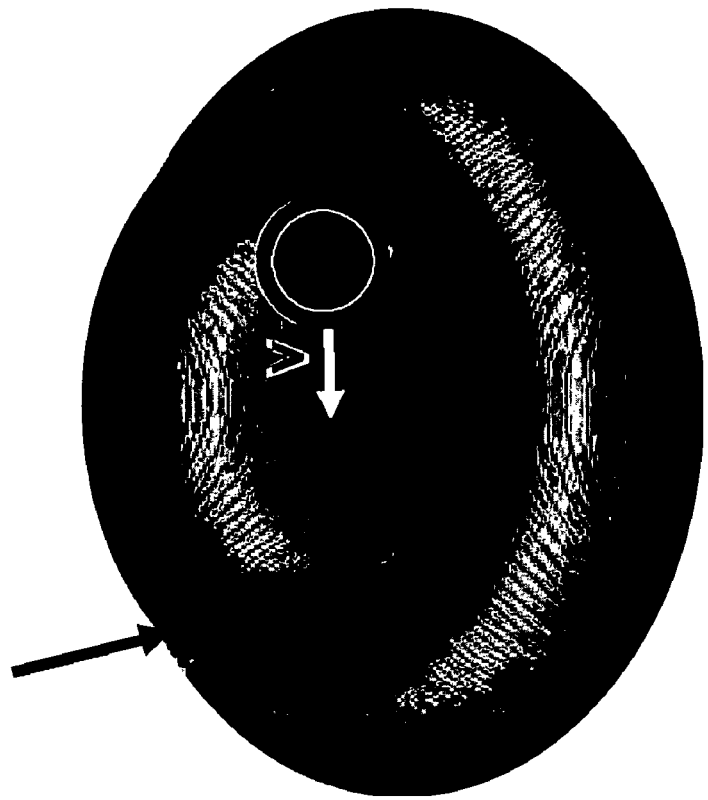
FIGS. 21A-21B are graphs of electric field distribution induced by a single optical ring pattern according to an aspect of the present invention.
Figure 21A:
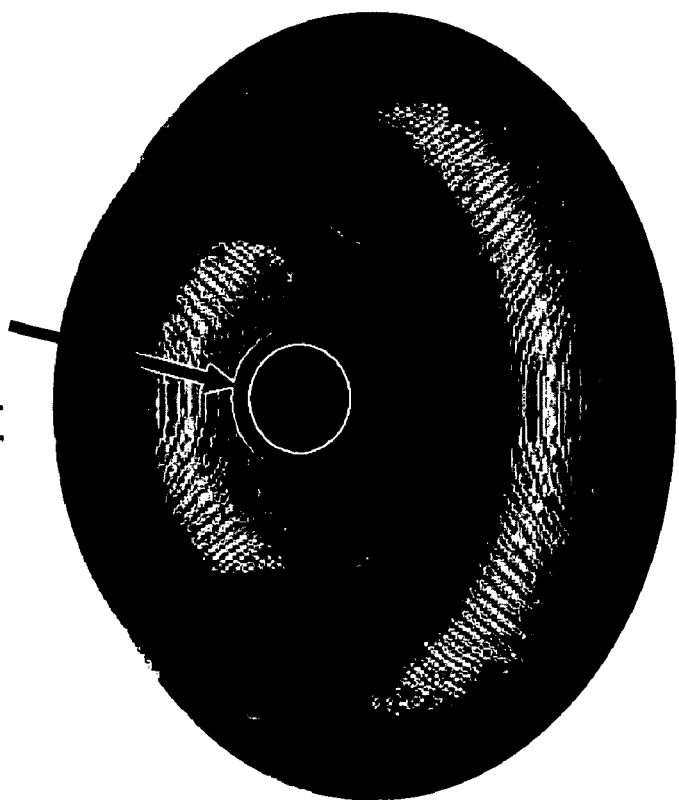

FIGS. 21A-21B illustrate, by way of example, the electric field distribution induced by a single optical ring pattern. In static state shown in FIG. 21A the particle is trapped in the electric field minimum in the center. During moving as shown in FIG. 21B the particle is displaced from the center as a result of the balance between the DEP and the viscous forces.

Particle trapped by an optical ring pattern trapping of a single particle is achieved by operating OET in the negative DEP regime. We create an optical ring pattern to form a virtual DEP cage that allows only one single particle to be trapped inside the ring, as shown in FIG. 21A.

In static state, the trapped particle will be focused at the center or the ring pattern where the minimum electric field strength occurs. When the optical ring moves, the trapped particle also move in the same direction but with a position deviated from the ring center so that the DEP force pushes the particle in the direction toward the center. This deviation distance depends on how fast the particle moves. When the optical ring moves too fast, the particle will escape the optical ring because the DEP force is not strong enough to hold it. The escaping speed of a 20 µm particle is 40 µm/sec in our current system. To trap a particle with a smaller size, a smaller optical ring would be required to ensure a single particle in the ring.

Figure 22A:
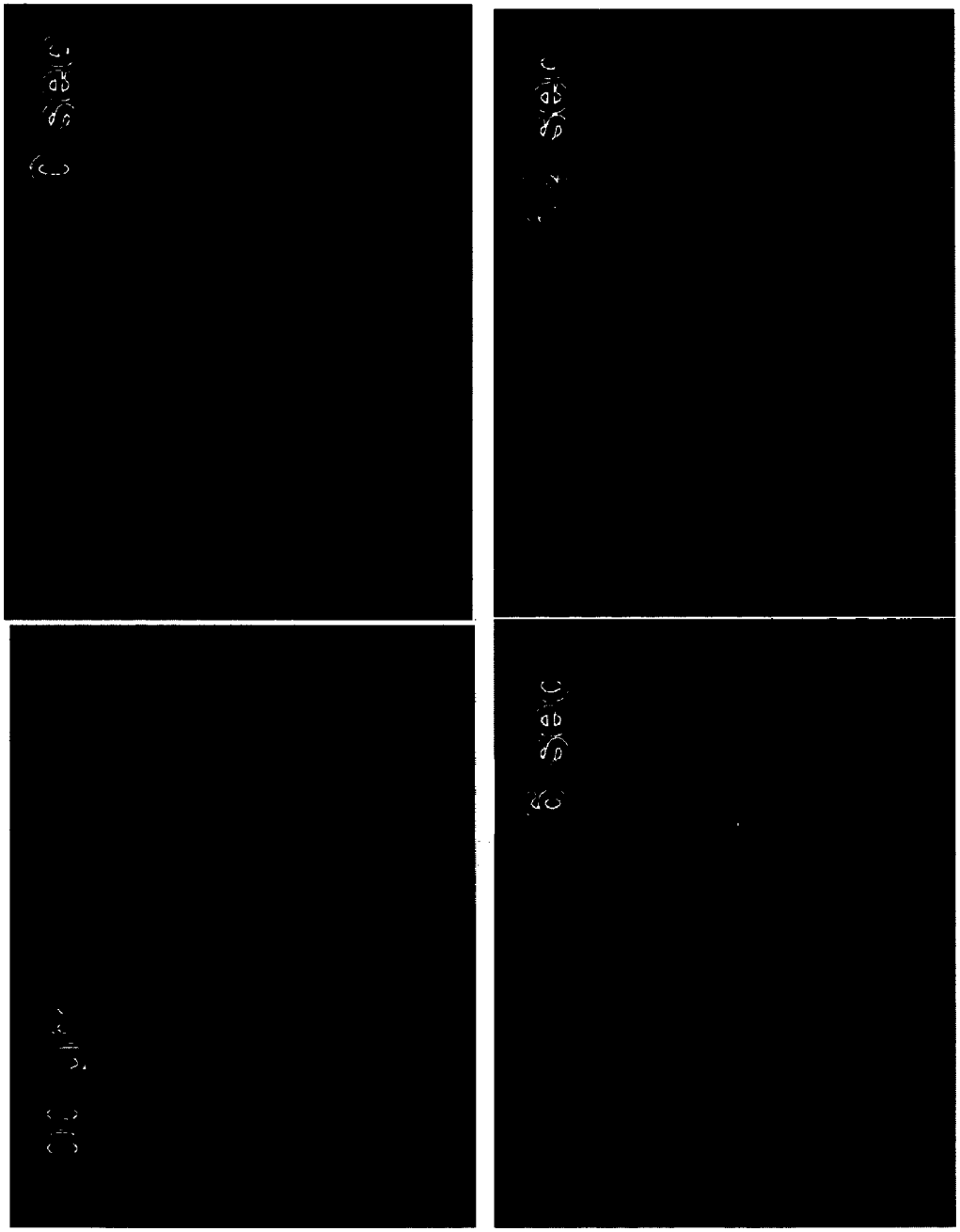
FIGS. 22A-22C are images of microvision-based automatic optical manipulation of microscopic particles according to an aspect of the present invention.
Figure 22B:
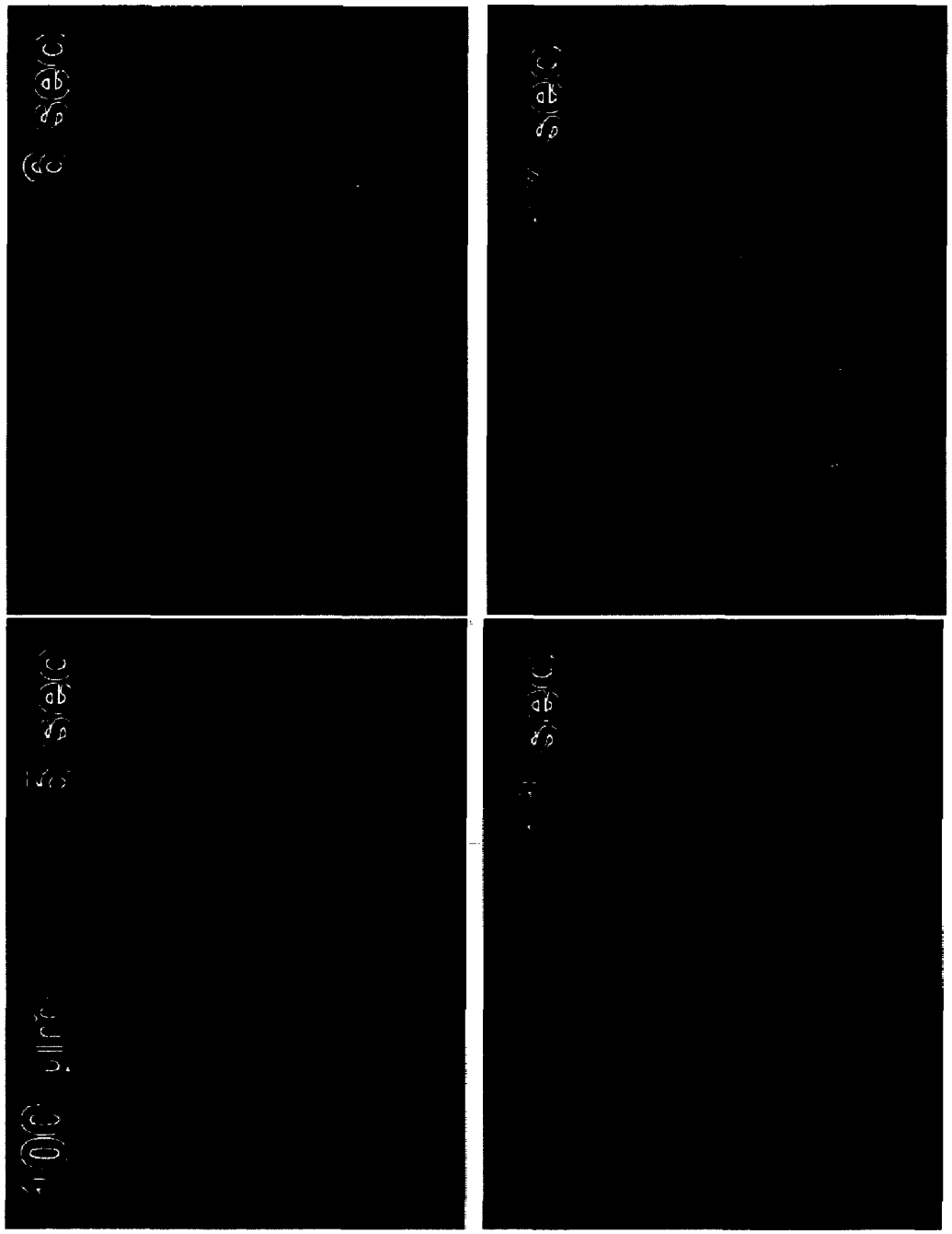
Figure 22C:
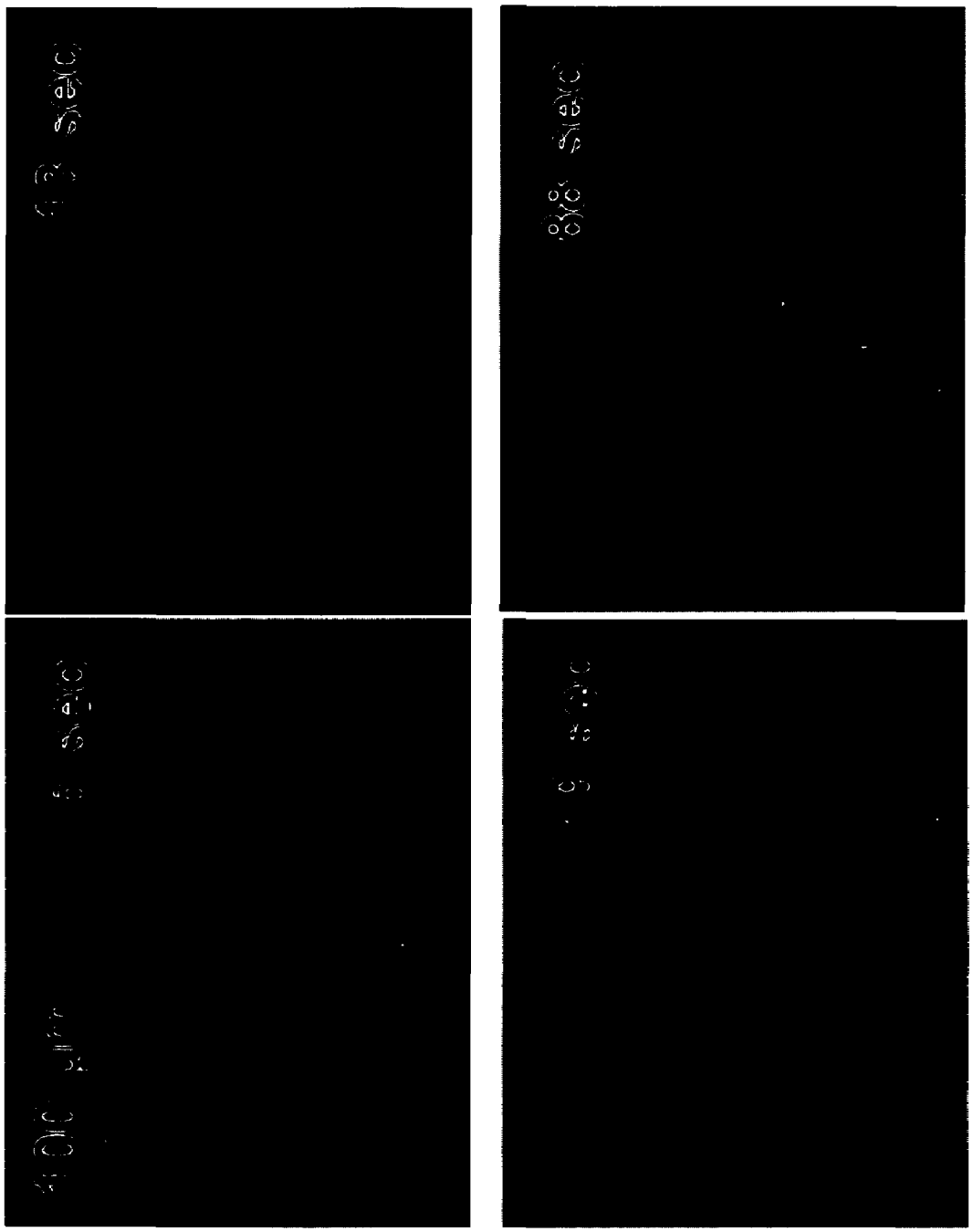

FIGS. 22A-22C each illustrate multi-frame example sequences of microvision-based automatic optical manipulation of microscopic particles. In FIG. 22A randomly distributed particles are shown being arranged into a hexagonal shape. In FIG. 22B the hexagonal pattern of FIG. 22A is shown being transformed into a line. In FIG. 22C the line pattern of FIG. 22B is then transformed into a triangle shape. In each case the unwanted particles are swept away by a scanning line.

Once the particle positions are recognized, the software is configured to generate the corresponding ring-shaped traps and calculates the transport trace for each particle. These optical patterns are stored as image files and are batch loaded to the DMD control software to create dynamic optical patterns to trap and transport particles. These processes are shown in FIG. 22A. The image of the randomly distributed particles was scanned vertically from left to right. The first six particles were identified and trapped by the OET by the 0 second frame. The trapped particles were transported by moving the ring traps, and reached the hexagonal configuration in 12 seconds.

FIGS. 22B and 22C show the video sequences of rearranging the particles into linear and triangular shapes and the unwanted particles were swept away by a scanning line pattern.

An automatic optical manipulator has been demonstrated that provides a feedback control through a microvision analysis system. This system can automatically recognize particles with specific size from a mixture of particles with different sizes and generate optical manipulating patterns to trap and move these selected particles to form a predetermined pattern. The large optical manipulation area (>1 mm×1 mm) of our OET device permits parallel manipulation of a large number of microscopic particles. The automatic parallel optical manipulation system greatly reduces the time for sorting and patterning microscopic particles. With further optimization, the system will be able to sort particles with different colors, shapes, or textures. More sophisticated optical manipulation functions can also be performed. The automatic optical manipulator has many potential applications in biological cell analysis and colloid science fields.

6. Manipulation of Live Red and White Blood Cells.

Optoelectronic tweezers (OET) provides a new tool for single-cell manipulation for biological research applications. Current cell-manipulation technologies, such as optical tweezers and dielectrophoresis, have limitations that can be overcome by OET.

Optical tweezers are a widely used tool for the manipulation of cells and microparticles in the micro-scale and nano-scale regimes. By integrating holographic imaging techniques with optical tweezers, multiple particle traps can be created from a single laser source. However, optical tweezers requires expensive, high-power lasers, and is limited in its effective manipulation area.

Dielectrophoresis (DEP) describes induced particle motion along an electric field gradient due to the interaction of the induced dipole in the particles and the applied electric field. This technique has been used to perform many biological experiments, including cell and DNA trapping and cell sorting. A limitation of conventional DEP devices is the difficulty of reconfiguring the devices for different experiments, as they rely on patterned metal electrodes to create the required non-uniform electric fields. By using CMOS technology to create DEP traps, real-time reconfigurable DEP devices can be achieved. However, these CMOS-based devices have a limited resolution, due to the area of the circuitry.

Optoelectronic tweezers offer low-power optically-controlled actuation of cells and microparticles via light-patterned virtual electrodes on a photoconductive surface. Since OET is directly controlled by optical images, it is easy to reconfigure in real time. In addition, high-resolution cell manipulation is achieved over a large area. As one of the major potential applications of OET is biological analysis, a number of experiments were performed using live cells. The first demonstration of OET on living cells was performed by Chiou et al., on $E.$ $coli$ bacteria, proving the low optical power of OET is capable of manipulation of live single cells without causing photodamage. In this aspect of the invention we present a description and demonstration of OET manipulation of live mammalian cells.

Optical tweezers work by directly converting photon momentum to a mechanical force on a microparticle or nanoparticle. This requires a highly-focused, intense laser beam. In contrast, optoelectronic tweezers creates an optically-patterned electric field, which in turn produces a dielectrophoretic force on particles. Due to the photoconductive gain, the required optical power is on the order of 100,000 times less than that required of a typical optical tweezers. As a result, an incoherent light source, such as an LED or halogen lamp, is sufficient for OET actuation. Furthermore, the optical pattern does not need to be highly focused, allowing OET to be effective over a larger area (currently 1.3 mm×1.0 mm) than optical tweezers traps.

Figure 23:
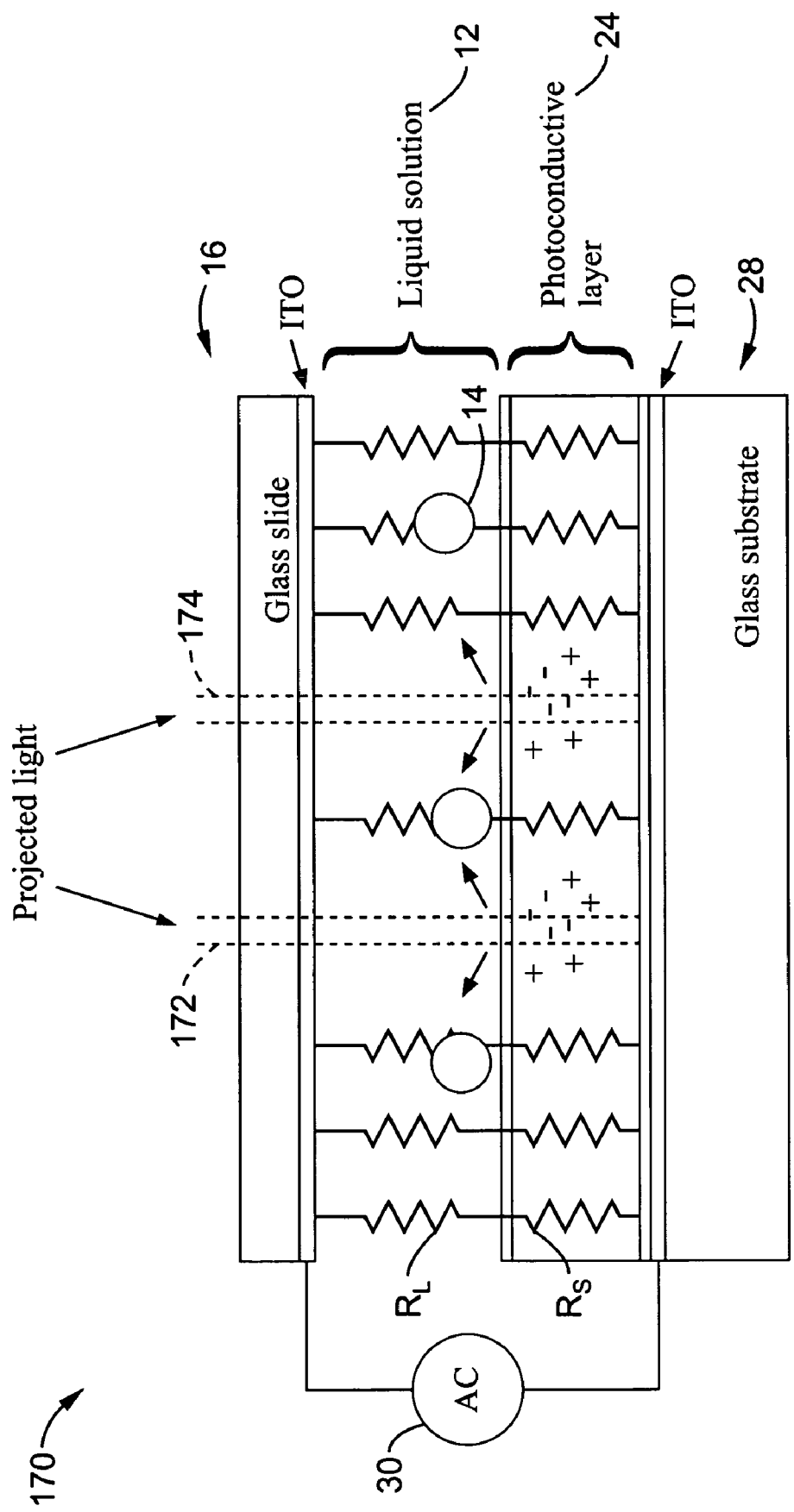
FIG. 23 is a schematic of an OET device according to an aspect of the present invention, showing modification of the electric-field patterns within the particle-laden liquid.

FIG. 23 illustrates an example embodiment 170 of the structure of an OET device according to the invention. The OET consists of an upper planar electrode 16 of ITO-glass and a lower photoconductive layer 24, between which are sandwiched a layer of liquid solution 12 containing the cells or microparticles 14 of interest. The upper planar electrode in this embodiment consists of a conductor such as indium-tin-oxide (ITO) which itself is transparent over a transparent glass slide, while the lower photoconductive layer is preferably formed with hydrogenated amorphous silicon (a-Si:H) deposited onto a ITO-coated glass slide via plasma-enhanced chemical vapor deposition (PECVD). Projecting light patterns 172, 174 modifies the electric field profile, creating a dielectrophoretic force. An AC bias 30 is placed across the upper electrode and the lower photoconductive layer.

In the dark regions, the applied AC voltage is dropped primarily across the highly-resistive ($R_S$) a-Si:H layer, which has a much higher impedance than ($R_L$) of the liquid 12, resulting in a low electric field in the liquid solution. However, in the illuminated regions, the projected light creates virtual electrodes, by locally increasing the conductivity of the a-Si:H. The photoconductor is now less resistive than the liquid, creating a high electric field region in the liquid above the virtual electrode. This creates non-uniform electric fields, which in turn creates a dielectrophoretic force to drive the cells.

Dielectrophoretic force is AC frequency-dependent. Thus, by varying the frequency of the applied AC bias, the force can be adjusted from an attractive force to a repulsive force, or vice-versa. Since OET uses optically-induced DEP, the OET force is also tunable in the same manner. As a result, there are two operating modes for OET: positive OET, in which cells and microparticles are attracted to the illuminated areas, and negative OET, in which cells and microparticles are repelled by the illuminated areas.

Figure 24:
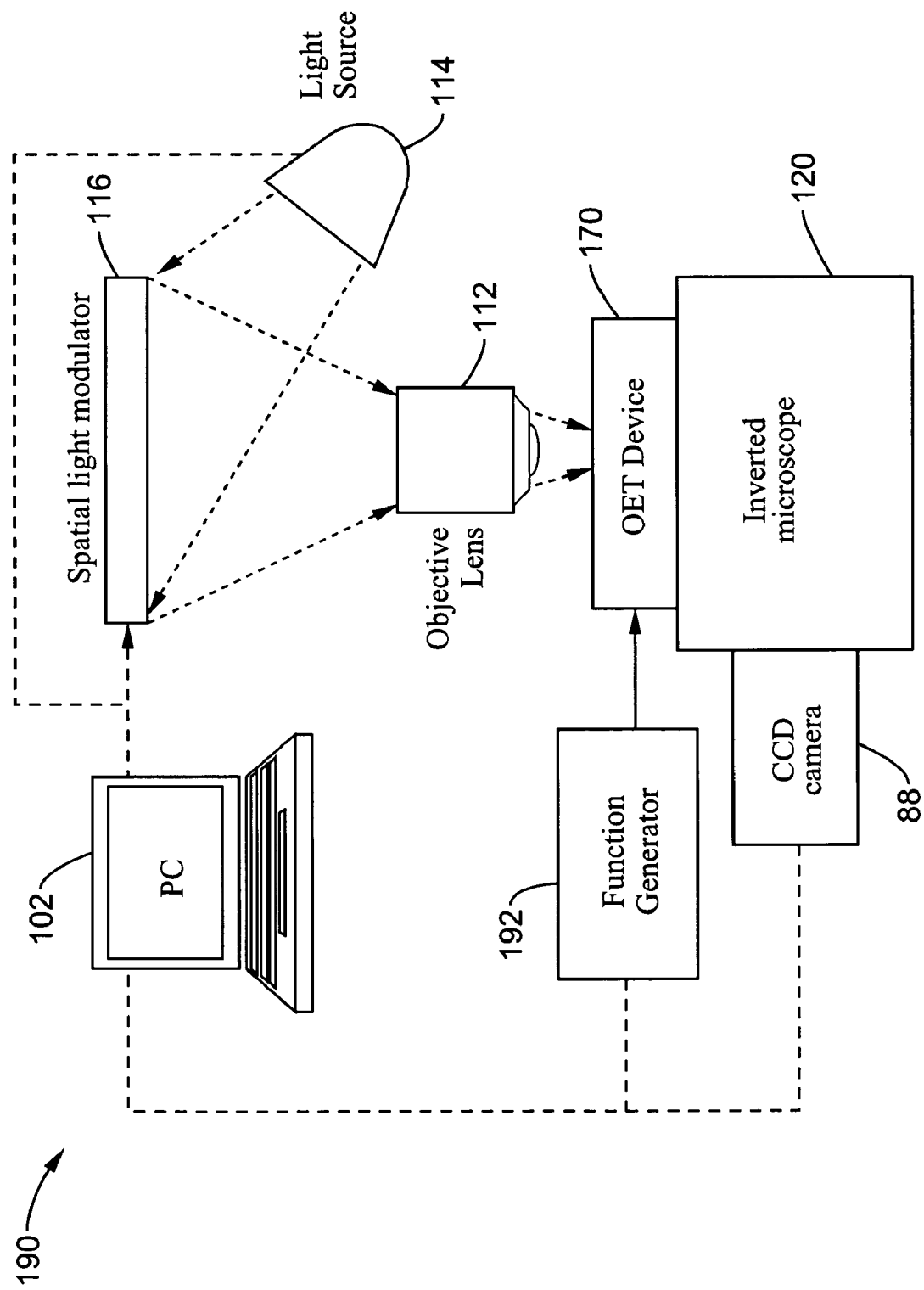
FIG. 24 is a schematic of an experimental OET device setup according to an aspect of the present invention, shown using a modulated laser light source to direct optical particle manipulation patterns.

FIG. 24 illustrates an example embodiment 190 configured for manipulation of bovine red blood cells utilizing optoelectronic tweezers according to the present invention. For this demonstration, the optical source 114 consisted of a 0.8 mW He—Ne laser ($\lambda$=633 nm). A spatial light modulator 116 is not necessary if a laser is used as the light source, as the laser can be directed into the objective either directly or through a mirror. A 10× objective lens 112 was used to reduce the laser beam size to about 20 µm in diameter. A personal computer (PC) 102 is shown coupled to control the light imaging via laser output control or a spatial modulator as well as to control the signals generated at OET device 170, such as bias voltage, from function generator 192 and for collecting data from a microscopic imager 88. The prepared cell solutions consisted of red blood cells (RBCs) from bovine serum, suspended in an isotonic solution (8.5% sucrose, 0.3% dextrose) at concentrations ranging from approximately 1 to 10% by volume. Approximately 5 µL of this solution was introduced into the OET device.

Figure 25A:
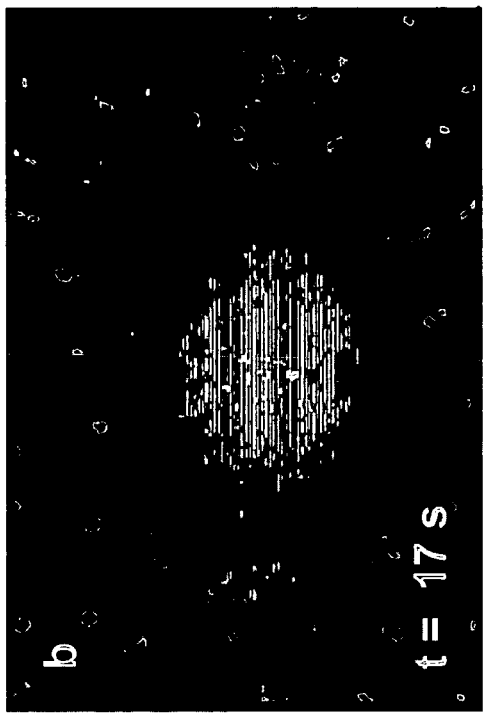
FIGS. 25A-25D are images of OET particle manipulation using a combination of optical input and AC biasing according to an aspect of the present invention.
Figure 25B:
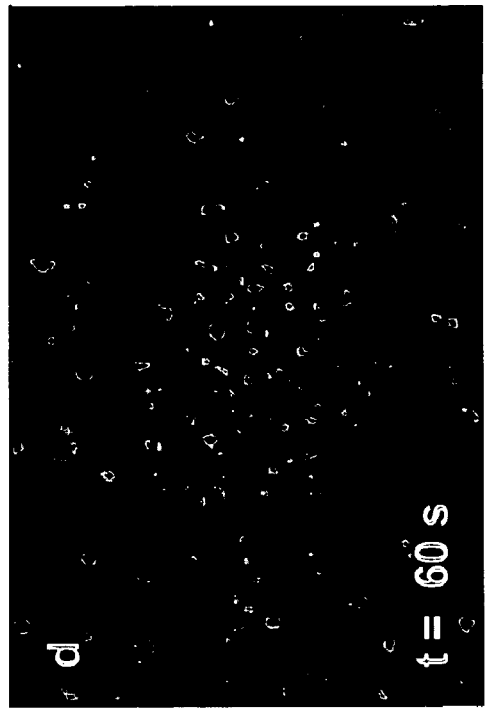
Figure 25C:
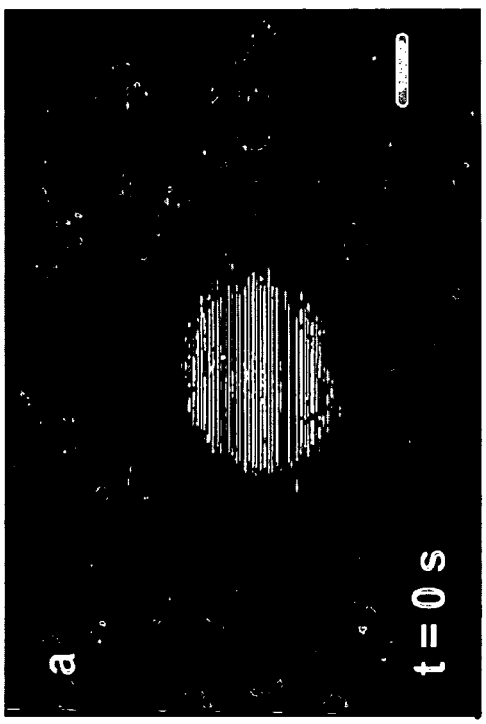
Figure 25D:
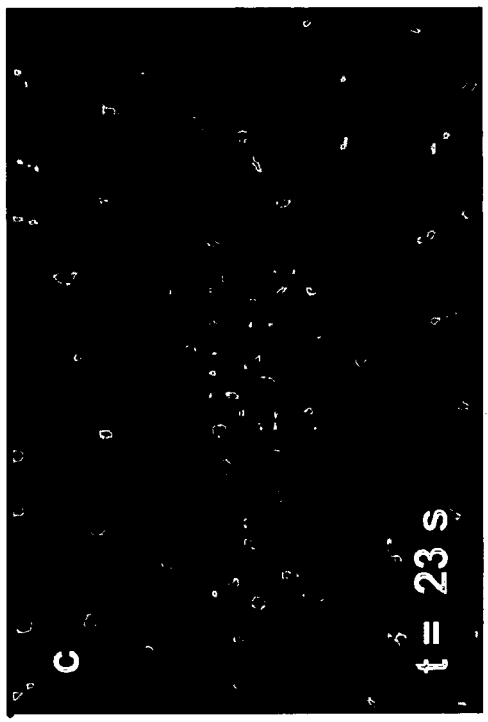

FIGS. 25A-25D depict resultant concentrations of blood cells using the OET of FIG. 24. A strong positive OET response was observed at an applied AC bias of 3 $V_{PP}$ at 200 kHz, attracting the red blood cells towards the laser spot shown in FIG. 25A. Initially, the laser is on in FIG. 25A, but no electric field is applied. An AC bias is then applied to the OET device, producing OET force, which attracts the blood cells to the illuminated area as shown in FIG. 25B. It was also observed that the cells align vertically along the electric field lines as in FIG. 25B. When the laser is turned off, the concentrated cells remain in the area that the laser spot was focused as shown in FIG. 25C. As the applied voltage is switched off, the concentrated red blood cells began to slowly pulsate, migrating away from the central area as shown in FIG. 25D, implying that they remain alive and viable.

The use of an incoherent light source and direct image patterning techniques increases the flexibility and functionalities of OET. A spatial light modulator can pattern any arbitrary image to be projected onto the photoconductive surface, creating the corresponding virtual electrodes on the OET device. Complex, reconfigurable manipulation patterns can thus be created by simple software programming. This powerful technique is demonstrated in the arrangement of human B-lymphocytes into a complex pattern.

A 100 W halogen lamp was used as the incoherent optical source. The spatial light modulator consisted of the Texas Instruments digital micromirror device (DMD). The DMD is a 1024×768 array of individually-addressable micromirrors, each of which is 13.68 µm×13.68 µm. The images displayed on the DMD are controlled via a computer. A 10× objective lens was used to increase the resolution of each DMD mirror to approximately 1.4 µm. The prepared cell solutions consisted of human white blood cells (B-lymphocytes), suspended in an isotonic solution. Approximately 5 µL of this solution was introduced into the OET device.

Figure 26B:
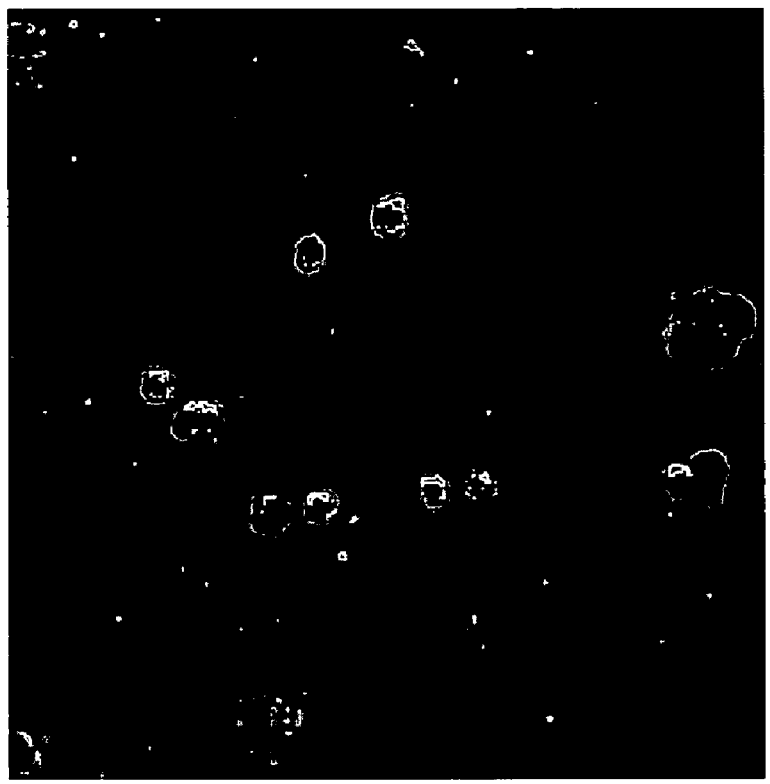
FIG. 26 is an image of OET particle manipulation according to an aspect of the present invention, shown in the process of forming the letters "UC" with human white blood cells.
Figure 26A:
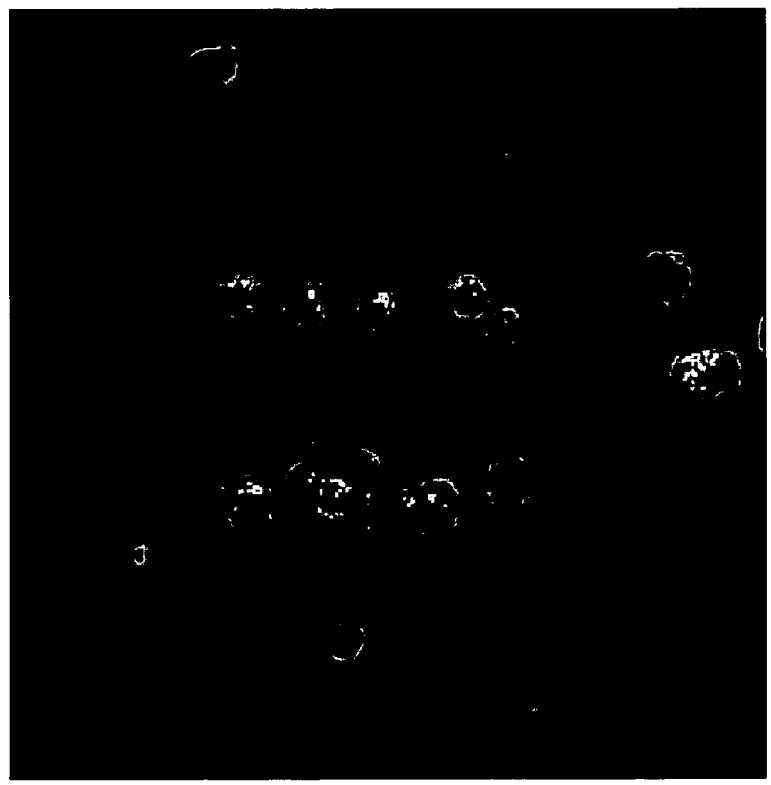

FIGS. 26A and 26B illustrate how B-lymphocytes can be manipulated into an arbitrary pattern. In this example we chose to assemble the cells into the shape of a "U" (FIG. 26A) and a "C" (FIG. 26B) character (for Univ. of California). At an applied bias of 14$V_{PP}$ at a frequency of 100 kHz, the white blood cells exhibit positive OET behavior. A shrinking concentric ring pattern is used to concentrate the cells towards the character image. Cells are attracted to each concentric ring.

As the rings shrink, the cells are transported towards the center of the concentric rings, where the character image is projected. The cells then become trapped by the static character pattern.

Optoelectronic tweezers provides a powerful tool for single-cell manipulation. The use of direct imaging and incoherent light sources provides OET with more flexibility than conventional DEP. The OET technique also uses considerably less optical power than optical tweezers, while still providing a larger effective manipulation area. Concentration and manipulation of cells, specifically red blood cells, has been demonstrated by using the OET and methods of the present inventive aspect. It should be appreciated that these manipulation functions can be easily tailored to a specific biological experiment.

7. Novel Optoelectronic Tweezers Using Light Induced Dielectrophoresis.

Optical tweezers have become an important tool in biological research areas since they were first demonstrated. However, the potential photodamage caused by the intense optical energy has restricted its use. For example, a 100 mW optical tweezers has a light intensity on the order of $10^{10}$ mW/cm$^2$ when focused to diffraction limit. Such an intense light energy may cause damages due to local heating or two-photon absorption. To reduce the photodamage, lasers with wavelengths in the near infrared region are often chosen to avoid the absorption in water or biological objects. However, the recent research shows the cell metabolism may still be affected even using infrared lasers.

Recently, a light induced electrophoresis mechanism has been proposed to optically address polymer beads by using DC electric bias. The electrically charged particles are attracted to the electrode with opposite polarity. In this paper, we present a light induced dielectrophoresis mechanism that would allow the optical addressing of electrically neutral micro-particles with µW optical energy, which is much lower than the approximately 1 mW to 100 mW of optical energy used by optical tweezers. Dielectrophoresis (DEP) refers the motion of an electrically neutral particle resulting from the interaction between the applied electric field and the induced dipole. It has been used widely in the manipulation of micro-particles or sub-micro-particles and biological cells. An analytical expression of DEP force is given by the following expression.

$$F_{dep} = 2\pi a^3 \in_m Re[K^*(\omega)]\nabla(E^2)$$

$$K^*(\omega) = \frac{\varepsilon_p^* - \varepsilon_m^*}{\varepsilon_p^* - 2\varepsilon_m^*}, \varepsilon_p^* = \varepsilon_p - j\frac{\sigma_p}{\omega}, \varepsilon_m^* = \varepsilon_m - j\frac{\sigma_m}{\omega}$$

According to the above equation E is field strength, a is particle radius, $\in_m$ and $\in_p$ are the permittivities of the surrounding medium and the particle, respectively, $\sigma_m$ and $\sigma_p$ are the conductivity of the medium and the particle, respectively, with $\omega$ the angular frequency of the applied electric field.

Figure 27B:
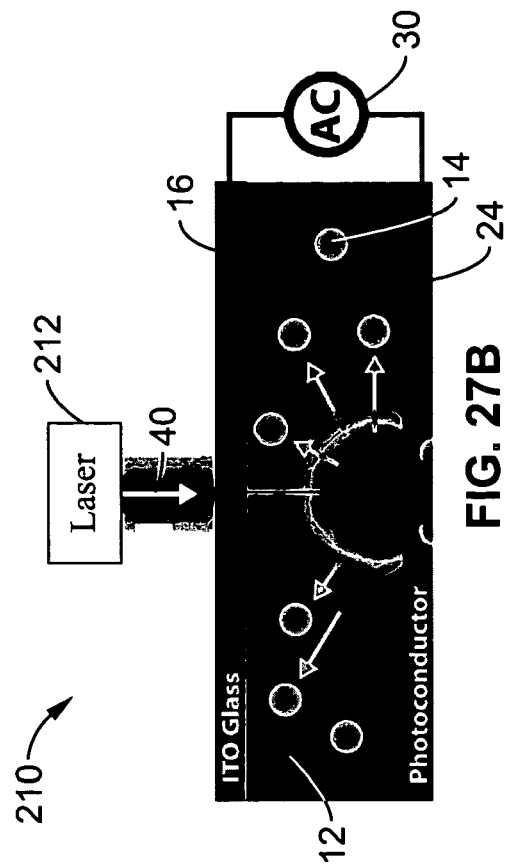
FIG. 27B is a schematic of the operation of the OET of FIG. 27A in response to one mode of induced dielectrophoresis.
Figure 27A:
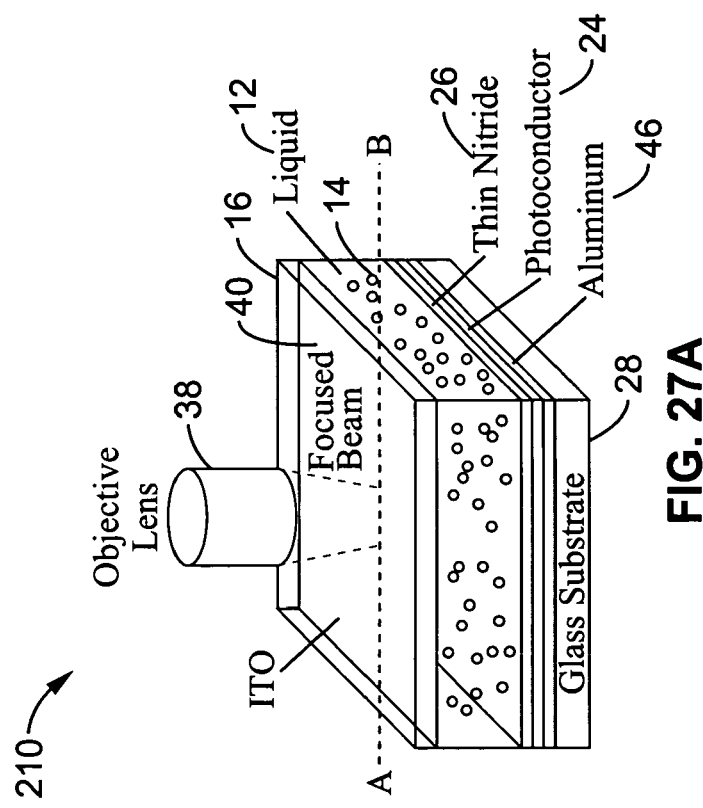
FIG. 27A is a perspective view of an OET device according to an aspect of the present invention, showing a focused beam directed through a liquid to a photoresponsive material.

FIGS. 27A-27B illustrate an OET embodiment 210 in FIG. 27A with an Illustration of the light induced dielectrophoresis mechanism in FIG. 27B.

The term $Re[K^*(\omega)]$ can have any value between 1 to $-\frac{1}{2}$, depending on the applied AC frequency and the polarizability of the particle and the medium. If $Re[K^*(\omega)]<0$, it is called negative DEP with the direction of the DEP force towards lower electric field. Since the DEP force is proportional to the gradient of the square of the applied electric field, a highly non-uniform electric field is desired to achieve a higher trapping force. In the following experiment a light induced negative DEP force is demonstrated.

In FIG. 27A, the structure of the optoelectronic tweezers are shown with a liquid solution 12 containing the particles sandwiched between two surfaces separated by a gap spacing of 100 µm. The top surface 16 is a commercial ITO glass. The bottom surface is a glass substrate 28 coated with three pattern-less layers: a 2000 Å-thick aluminum layer 46, a 2 µm-thick photoconductive (amorphous silicon) layer 24, and a 200-Å-thick silicon nitride layer 26. An AC bias 30 is applied between the top (ITO) and the bottom (aluminum) electrodes. In the dark state, the majority of the voltage drops across the photoconductor due to its high electrical impedance, which results in a very weak electric field in the liquid layer. When the laser beam 40 is focused through objective 38 on photoconductive layer 24, the local photoconductivity at the site under light illumination is greatly increased due to the photogenerated electron-hole pairs.

FIG. 27B depicts a light defined micro electrode turned-on locally and creating a highly non-uniform field in liquid layer 12. The laser spot creates a light defined electrode and a highly non-uniform electric field in the liquid layer. The particles inside the liquid are polarized by the non-uniform field and pushed away from the illuminated site by the negative DEP force.

Since light is used to switch the AC voltage drop between the photoconductive layer and the liquid layer, rather than to directly trap the particles, the required optical power is orders of magnitude lower than that of conventional optical tweezers.

Figure 28:
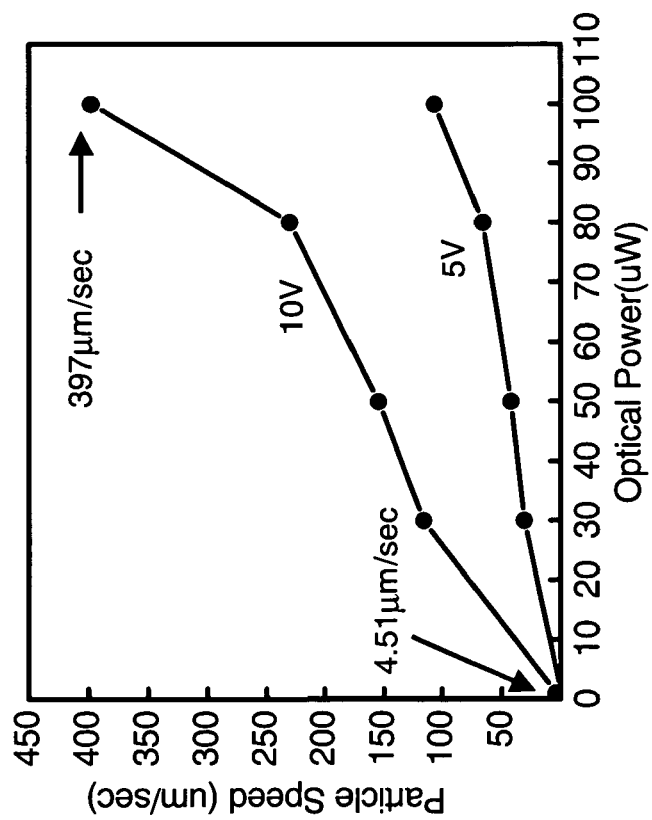
FIG. 28 is a graph of the relationship between particle speed and optical power for an OET according to an aspect of the present invention.

FIG. 28 depicts experimental results for the OET of FIG. 27A with the relationship between particle speed and optical power. In the experiment, a 800 µW laser with a beam width 0.24 mm and a wavelength of 632 nm is used as the light source. The laser beam is preferably steered by a pair of orthogonally scanning galvanometer mirrors and then sent through a combination of a convex lens and a 40× objective lens. The optical spot size on the photoconductive layer is around 17 µm. Neutral density filters are used to control the incident optical energy. A 100 kHz AC bias is applied between the top and the bottom electrodes to drive 25 µm latex particles. To measure the particle speed, the scanning mirror is programmed to scan at a constant speed to push the particle. The particle is pushed by the optical beam, until at sufficiently high scan rate, the particle can no longer keep up with the optical beam. The maximum speed at which the particle responds to scanning optical beam is measured for various optical powers and AC bias voltages. An optical beam with power as low as 1 µW light is sufficient to transport the particle at a speed of 4.5 µm/sec at 10 V AC bias. The maximum speed observed here is 397 µm/sec, which corresponds to a force of 187 pN estimated by Stokes' law.

Figure 29B:
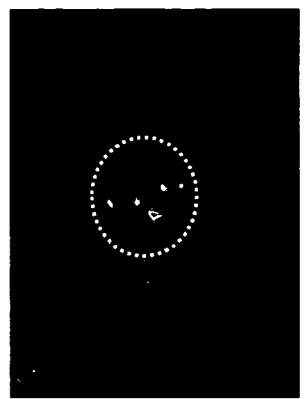
FIGS. 29A-29B are images of using an OET to focus/concentrate multiple particles according to an aspect of the present invention.
Figure 29A:
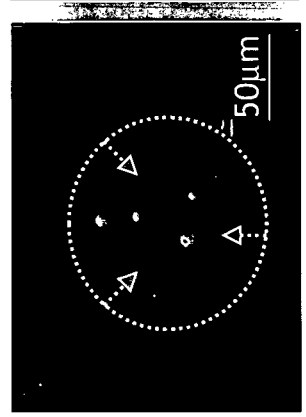

FIG. 29A and FIG. 29B illustrate an example of multi-particle focusing, in which the laser beam is programmed to scan in circular patterns. The four particles are focused, or squeezed, to the center of the shrinking circular pattern.

According to the present aspect of the invention a novel optoelectronic tweezers is demonstrated which is successfully applied to transport neutral micro particles. The required optical power on the order of from (i.e., approximately 1 µW-100 µW) is one to two orders of magnitudes lower than that of optical tweezers. Particle transport speed of 397 µm/sec and trapping force of 187 pN are measured for 25 µm latex particles with 100 µW optical power and 10 V AC bias.

8. Optical Sorting Mechanism in Dynamic Electric Field.

Optoelectronic tweezers (OET) have been proposed herein as a powerful tool for cell and microparticle manipulation, via direct optical images. The optically-patterned electrical field generated on the OET surface can be configured to trap and transport single or multiple cells in parallel. Such a dynamic reconfigurable electric field provides driving forces for sorting particles without the need for pumps to introduce fluid flow, as presented in most of the microfluidic sorters. It completely eliminated the need for the fabrication and integration of complex microfluidic components, adding lots of flexibility in the applications of cell or particle manipulation. In the present invention an OET based sorting mechanism is demonstrated using a dynamic moving light beam. Particles on the OET surface can be sorted simply by scanning a light beam across the OET surface. The sorted particles can be transported to other areas by other dynamic optical patterns that have been demonstrated in the industry. The following portion of the present invention focuses on the fundamental mechanism of OET-based optical sorting.

Figure 30A:
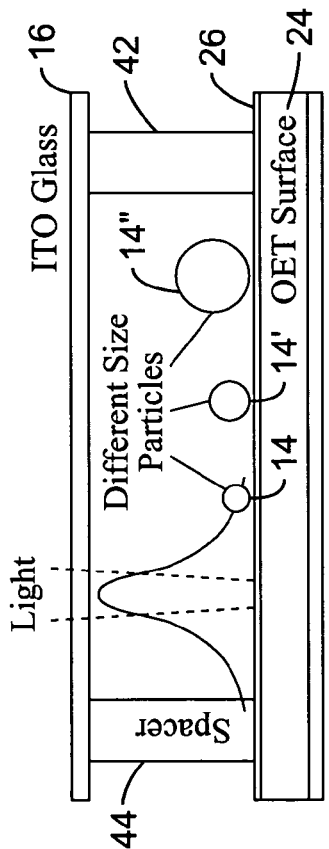
FIGS. 30A-30C are schematics of an OET device according to an aspect of the present invention, showing how different sized particles are organized in response to an optical wave induced electric field.
Figure 30B:
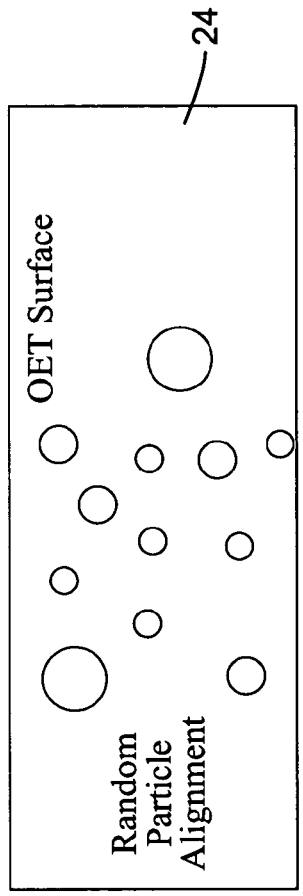
Figure 30C:
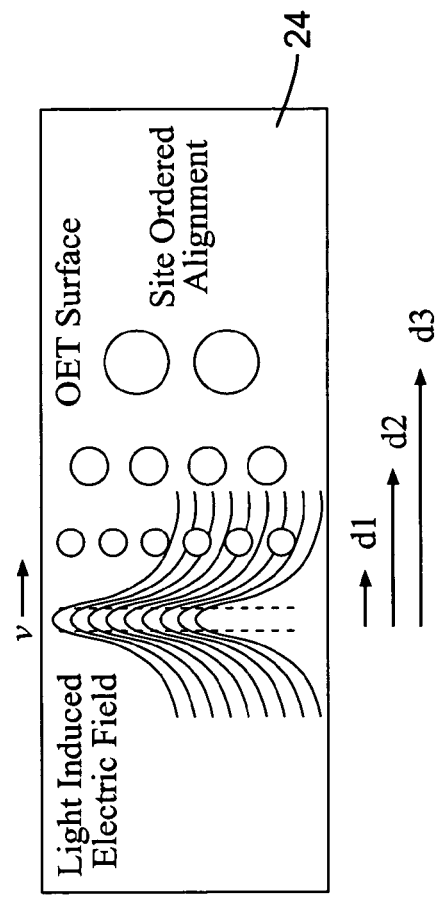

FIGS. 30A-30C illustrate dynamic electric fields induced by an OET according to the present invention. In FIG. 30A a schematic diagram is shown for the OET device, in which different sized particles 14, 14', 14" are sandwiched between a top ITO glass 16 and a bottom OET photoresponsive surface 24. In FIGS. 30B-30C randomly distributed particles are sorted out when the line-shape laser beam scans across the OET surface.

Optoelectronic tweezers are a novel mechanism that enables optical patterns to induce highly non-uniform electric fields on a photoconductive thin film material. The particles near the non-uniform electric field experience a net force, resulting from the interaction between the electric field and the induced electric dipole of the particles. This force is called dielectrophoretic (DEP) force, which can be expressed in the following relation.

$$F_{dep} = 2\pi r^3 \in_m Re[K^*(\omega)] \nabla(E^2)$$

According to the above equation E is field strength, r is particle radius, $\in_m$ and $\in_p$ are the permittivities of the surrounding medium and the particle, respectively, $\sigma_m$ and $\sigma_p$ are the conductivity of the medium and the particle, respectively, with $\omega$ the angular frequency of the applied electric field and $K^*(\omega)$ is the Clausius-Mossotti (CM) factor, which has a value between 1 and −0.5, representing the polarizability of the particle.

This force is very sensitive to the size of the particle $a^3$ and the non-uniformity of the field $(\nabla E^2)$. If a particle is less polarizable than the medium, its real part of the CM factor is negative, and the particle will be pushed away from the high electric field area. When a line-shaped laser beam scans across the OET surface, it produces an electric field pattern that moves at the same speed. This light-induced electric field will push particles in the OET device. The relative distance between the moving light beam and the particles is determined by the balance between the DEP force and the viscous force. Using Stoke's Law to estimate the viscous force for a moving particle, we obtain the following relationship between the particle size and nonuniformity of the field.

$$r^2 \nabla(E^2) = C = \frac{3\eta v}{\varepsilon_m Re[k^*(\omega)]}$$

In the above equation r is the particle radius and C is a constant determined by the light scanning speed v, real part of the CM factor, and also the viscosity $\eta$, and permittivity $\in_m$, of the surrounding medium. Since the term $\nabla E^2$ is a function of the relative distance between the particle and the electric field maximum, particles with different sizes will have different deterministic relative distances to the center of the scanning laser beam. Based on this principle, particles with different sizes will be sorted out when the laser beam scans across the OET surface.

Figure 31:
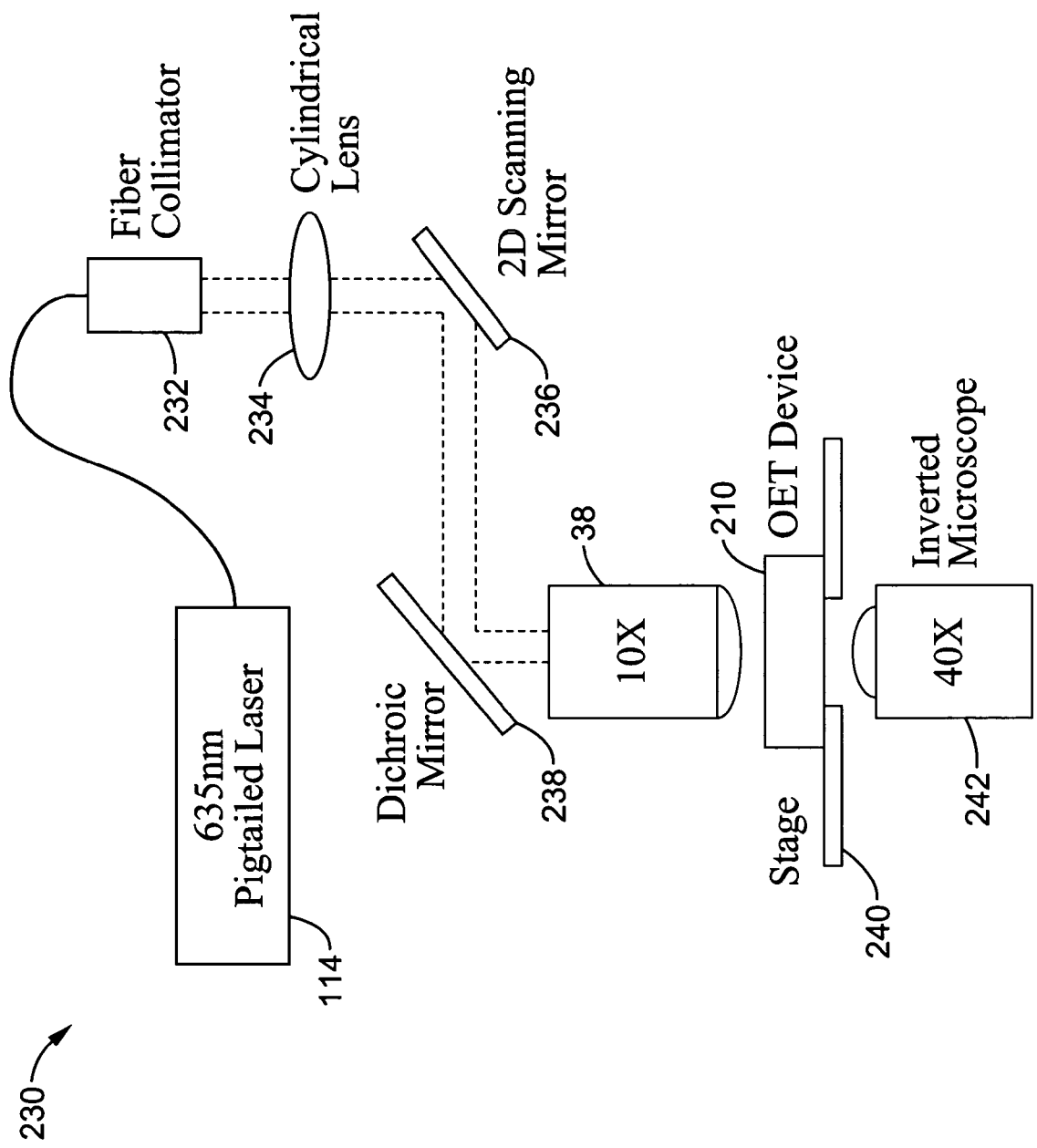
FIG. 31 is a block diagram of an OET optical setup according to an aspect of the present invention, showing a laser illumination source with underside microscopic imaging.

FIG. 31 illustrates an example embodiment 230 of an experimental setup for optical sorting of microscopic particles. A single-mode fiber pigtailed laser diode 114 with a wavelength of 635 nm is coupled through a fiber collimator 232, producing a beam spot size of 3 mm and an optical power of 120 µW. A cylindrical lens 234 directed through a 2D scanning mirror 236 and dichroic mirror 238 and a 10× objective 38 lens are used to shape the circular Gaussian beam into a line shaped pattern and focus it onto the OET surface. A scanning mirror is programmed to steer the laser beam. The OET device 210 is shown on a stage 240 and configured with a microscopic imaging means for registering particle (or cell) position and characteristics within the OET.

Figure 32A:
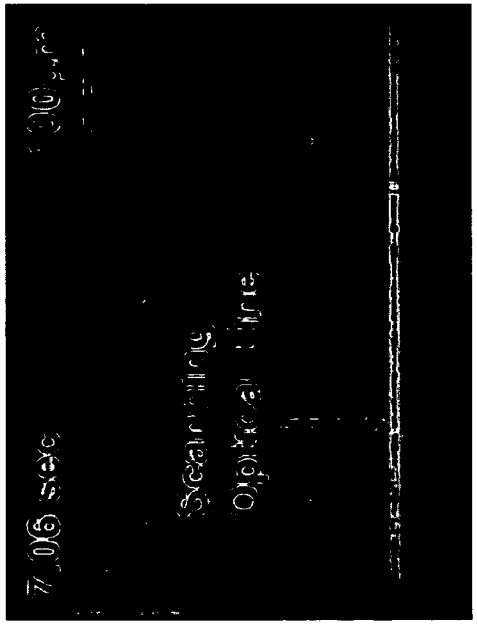
FIGS. 32A-32D are images of OET-based size sorting according to an aspect of the present invention, showing size sorting of particles of approximately 10 μm and 20 μm.
Figure 32B:
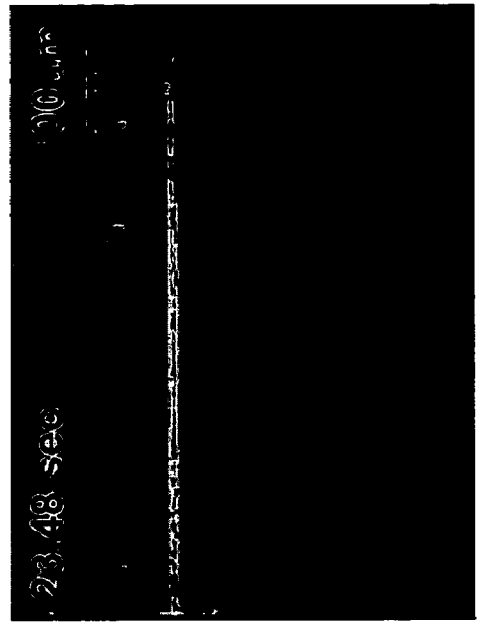
Figure 32C:
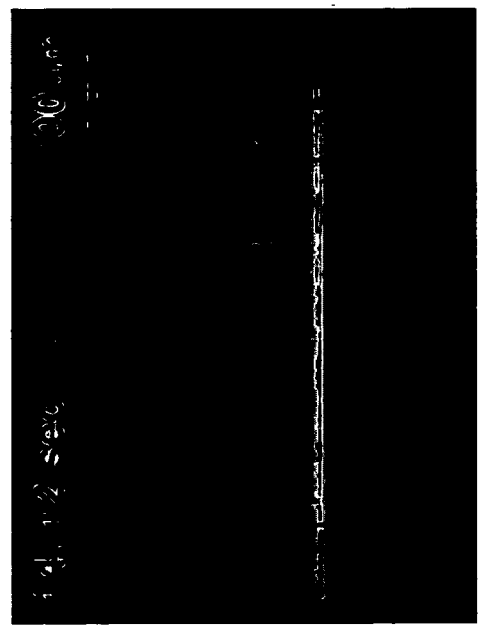
Figure 32D:
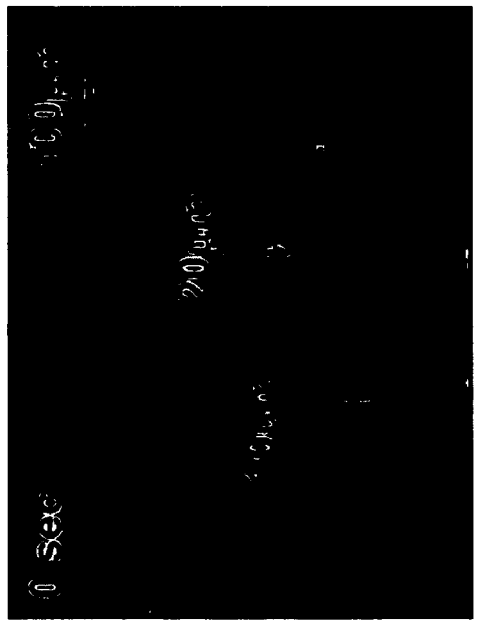

FIGS. 32A-32D depicts the result when the laser beam (120 µW red diode laser at wavelength=635 nm) scans across the OET surface of FIG. 31 where the 10 µm and 20 µm diameter polystyrene beads are randomly distributed. In FIG. 32A the particles are randomly distributed on the surface. In FIG. 32B the optical beam scans across the area of the 10 µm beads and aligns them into a line pattern. In FIG. 32C the 10 µm and 20 µm beads are aligned and moving with different relative distances to the center of the optical beam. In FIG. 32D the optical beam is programmed to "jump" into the spacing between these two groups of particles and further separate them.

After the line-shaped laser beam scans across the assortment of beads, the 10 µm and 20 µm beads become aligned at different distances relative to the center of the beam. The laser beam is programmed to "jump" between these two groups of particles and further separate them. This sorting process finished in 25 seconds.

Figure 33B:
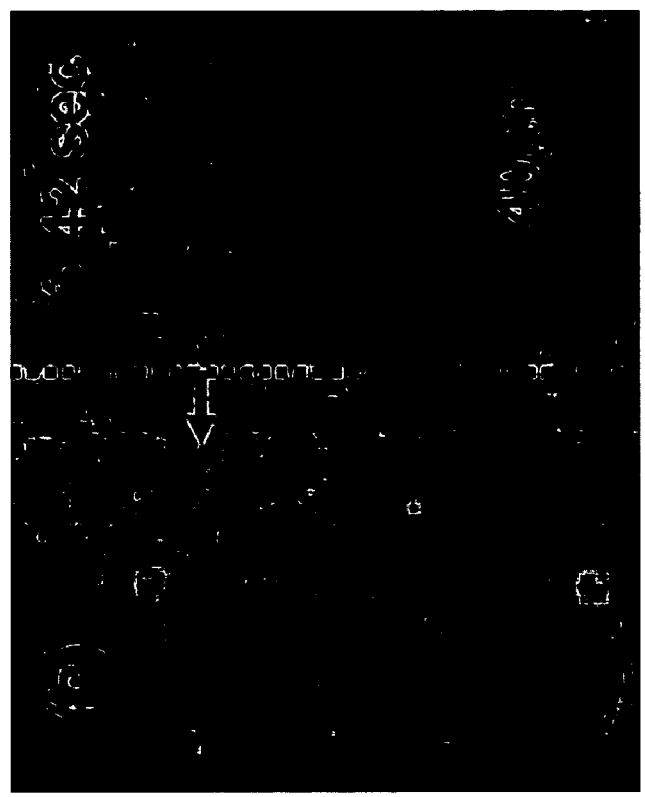
FIGS. 33A-33B are images of OET-based size sorting for particles in a range of sizes according to an aspect of the present invention.
Figure 33A:
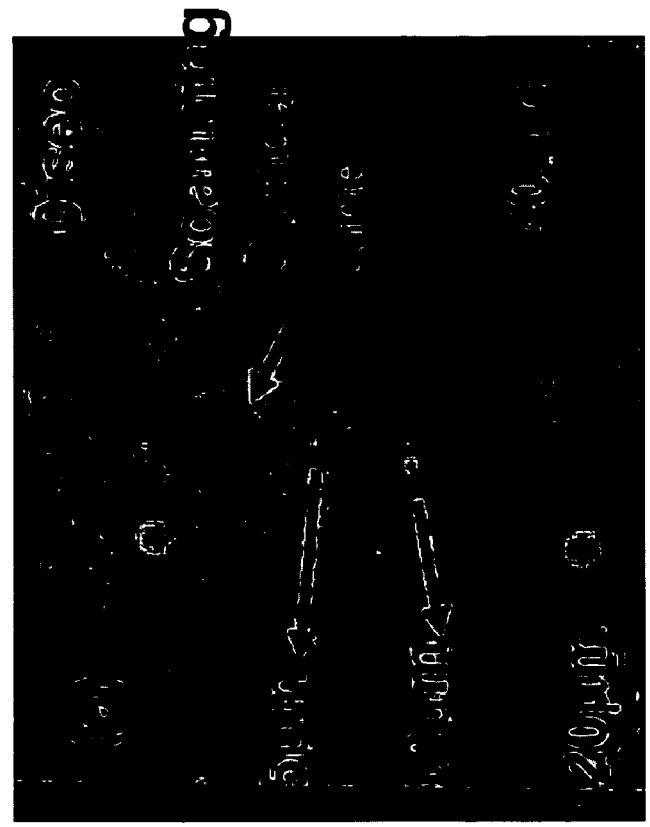

FIGS. 33A-33B shows the sorting of particles of different sizes; specifically 5 µm, 10 µm, and 20 µm particles with relative distances of 15 µm, 20 µm, and 40 µm, respectively, under the scan speed of 6 µm/sec. The optical beam scans at a constant rate from the left to the right. These three sizes of particles are moving at the same speed as the light beam. Their deterministic relative distances remain constant during the movement. The relative distance is scan speed dependent. At a high scan speed, the particle experiences a larger viscous force. In order to balance this force, the particle moves closer to the scanning beam, where a stronger electric field gradient exists.

Figure 34:
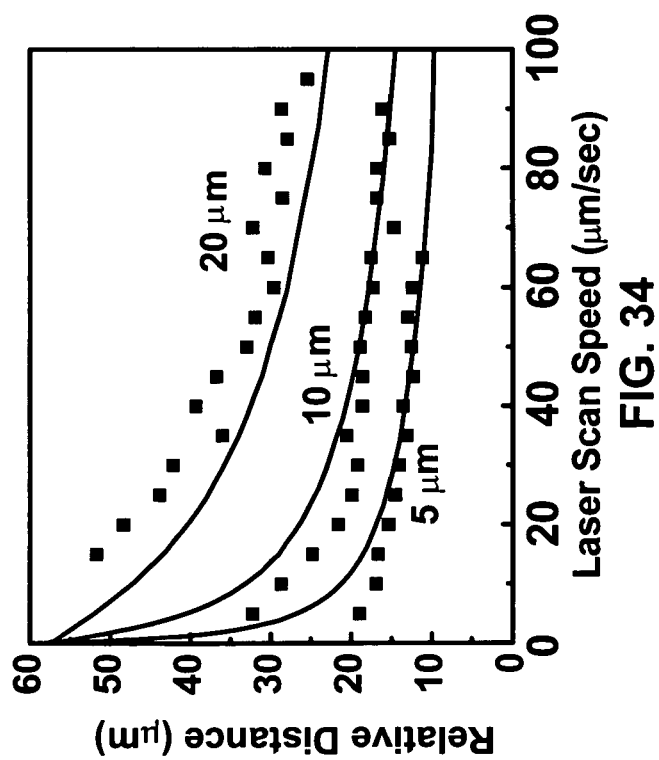
FIG. 34 is a graph of distance versus speed for the different particle sizes demonstrated according to an aspect of the present invention.

FIG. 34 depicts the relationship between the scan speed and the relative distances of microparticles from the scanning beam center as a function of scanning speed. Theoretical calculations are shown in solid lines and experimental data is shown by the dots.

For the 20 µm particle, the relative distance to the scanning beam center decreases from 50 µm to 25 µm when the scan speed increase from 20 µm/s to 100 µm/s. This trend is also reflected in the data for 5 µm and 10 µm particles. Thus, low scanning rates provide a larger spatial separation between different sizes of particles. At a scanning speed of 17 µm/sec, the spacing between 5 µm and 10 µm particles is 7 µm, and the spacing between 10 µm and 20 µm particles is 28 µm. The maximum scanning rate for a 5 µm particle is approximately 70 µm/sec. If the scanning rate is increased beyond this limit, the particle becomes levitated by the vertical non-uniformity of the electric field, causing the particle to escape the lateral "pushing force" of the scanning beam. The escape speed is higher for bigger particles; for a 10 μm bead, it is 90 μm/sec.

The present invention provides a novel optical sorting mechanism based on optoelectronic tweezers (OET). The light induced dynamic electric fields sort out particles with diameters of 5 μm, 10 μm, and 20 μm by simply scanning a light beam across the OET surface. This technique completely eliminates the requirement of extra pumps as a driving force for liquid flow, greatly simply the fabrication and integration process of microfluidic system. The deterministic relative distances from the beads to the beam center are size-dependent. Particle sorting performed on 5 μm and 10 μm-diameter beads resulted in a spacing of 7 μm between the separated groups. The spacing between sorted 10 μm and 20 μm diameter particles was 28 μm.

9. Moving Toward an all Optical Lab-on-a-Chip System.

Miniaturization and integration of microfluidic systems could reduce the cost as well as increase the speed of many analytical biological and chemical processes. Multiple microfluidic functions are integrated on a chip, referred to as "lab-on-a-chip", to perform the biological analysis. These functions include microfluid delivery mixing, cell trapping, concentrating, and sorting. Conventional lab-on-a-chip systems consist of micro pumps, valves, and fluidic channels.

The fluidic circuits, and therefore their functions, are usually fixed by the specific structure which has been fabricated. By contrast to the conventional "fixed" microfluidic system, the optical manipulation approach taught herein offers several advantages. The present invention is flexible and easily re-configurable. Optical tweezers have been widely used to trap cells and other bio-particles, and recently, holographic optical tweezers have been proposed to perform multiparticle trapping, optical sorting, particle spinning, three-dimensional manipulation, and optical pumping of microfluid. These microfluidic functions permit an all-optical-lab-on-a-microscope system that is programmable and reconfigurable in response to light input. However, the optical tweezers-based systems suffer from the following limitations. First, control of microfluids using optical force is not energy efficient. The optical energy is first transferred to the kinetic energy of colloidal particles or beads. The moving beads induce liquid flow through the viscous force. The maximum force from optical trap is around 100 pN, which is not large enough to drive liquids through microchannels effectively due to a large pressure drop. Second, the optical power required by optical tweezers is very high. It requires tightly focused laser beams to provide optical gradient force for trapping or deflecting the particle motion.

Typically, a single trap requires 1 mW of optical power, and multiple traps require even higher power. Here, instead of using optical force the present invention relies upon a light-induced electrowetting mechanism, called optoelectrowetting (OEW), for controlling microfluids and a light-induced dielectrophoresis mechanism, called optoelectronic tweezers (OET), for manipulating microscopic particles.

Figure 35:
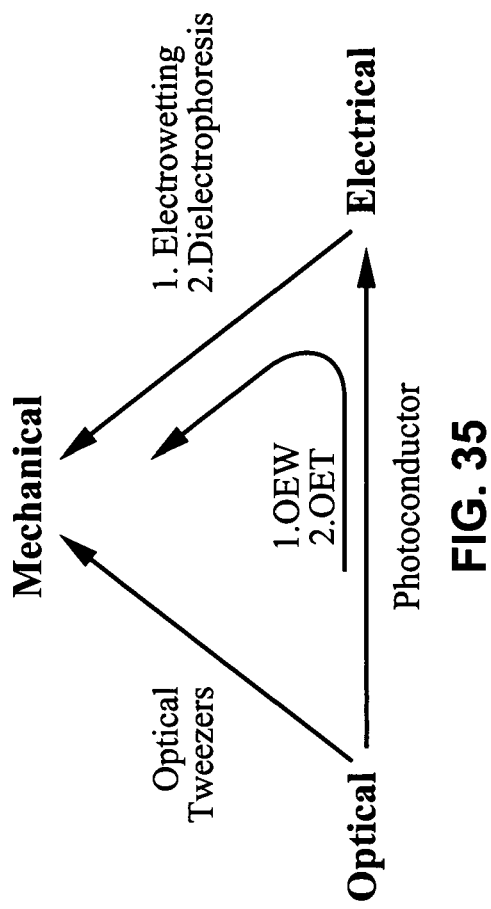
FIG. 35 is a flow diagram comparison of the energy transfer paths according to different optical manipulation methods.

FIG. 35 illustrates the concept by a comparison of energy transfer paths of different optical manipulation methods, wherein optical energy is first converted to electrical energy, which in turn drives the liquids or particles through electrowetting or DEP processes, respectively. As a consequence of the optoelectronic gain of the photoconductor, the required optical power is reduced by four to five orders of magnitude. Optical tweezers transfer energy from optical domain directly to mechanical domain, while optoelectrowetting (OEW) and optoelectronic tweezers (OET) transfer optical energy to electrical domain first and then trigger the electrical force for the manipulation.

Surface tension is the dominant force for controlling liquids in microscale. Several mechanisms have been proposed to control the surface tension. Electrowetting is attractive because of its fast response and low power consumption. It changes the contact angle of a droplet on a solid surface by modulating the surface energy at the liquid-solid interface with electrostatic energy. Optoelectrowetting uses optical beams to control the amount of electrostatic energy stored in that interface and thus the contact angle.

FIGS. 36A-36B illustrate an embodiment 250 of optoelectrowetting in which a water droplet 252 is placed on a glass substrate coated with a transparent conductive glass 20, a photoconductive layer 24, and a thin dielectric layer 16. FIG. 36A depicts the droplet without light illumination, with the contact angle 254 being the same as the initial angle without bias. In FIG. 36B illumination is generated by source 212 and the contact angle of droplet 252' decreases due to the electrowetting effect.

An AC electrical bias is applied between the bottom electrode and the droplet. The photoconductor is configured with a high electrical resistance in the dark, resulting in a RC charging time much longer than the AC signal cycle. A very small amount of the voltage drops across the capacitor between the droplet and the photoconductor. The contact angle in the dark is the same as the initial angle without bias, as shown in FIG. 36A. When light shines on the photoconductor layer, it creates electron-hole pairs and increases the photoconductivity by several orders of magnitude. The RC time becomes much smaller than the cycle of the AC signal, resulting in a fully charged capacitor, as shown in FIG. 36B. These extra electrical charges stored in the capacitor change the surface energy between the solid-liquid interface and thus the droplet contact angel. The relation between the contact angel and the voltage across the insulator can be expressed by the following.

$$\cos[\theta(V)] = \cos[\theta_0] + \frac{1}{2}\frac{\varepsilon}{d\gamma_{LV}}V^2$$

In the equation above the value $\theta_0$ is the initial contact angle, $\in$ is the permittivity of the insulator, d is the thickness of the insulator, $\gamma_{LV}$ is the surface tension of the liquid-vapor interface, V is the root-mean-square voltage of the applied signal.

Figure 37A:
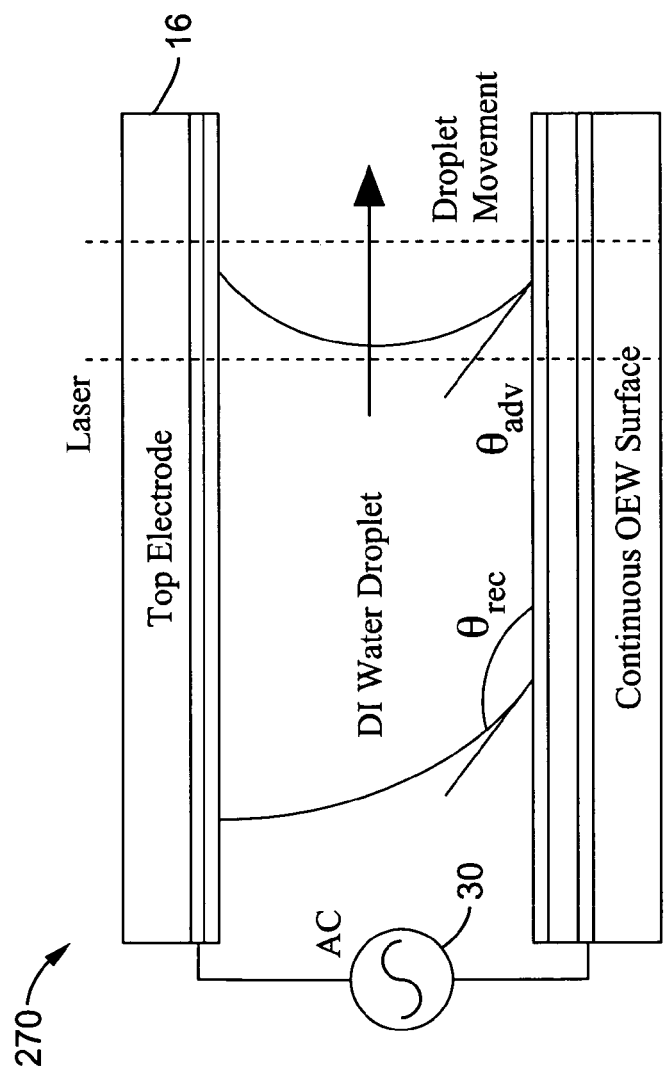
FIG. 37A is a schematic of droplet transport on a continuous OEW surface according to an aspect of the present invention.
Figure 37B:
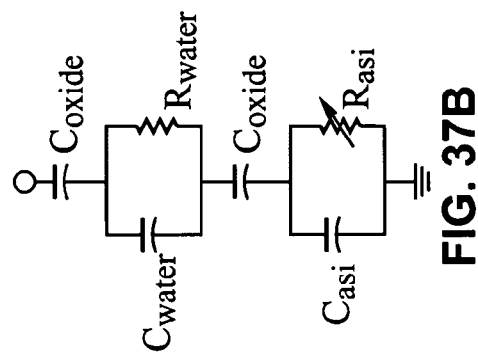
FIG. 37B is a schematic of an equivalent electrical circuit for the OEW of FIG. 37A.
Figure 37C:
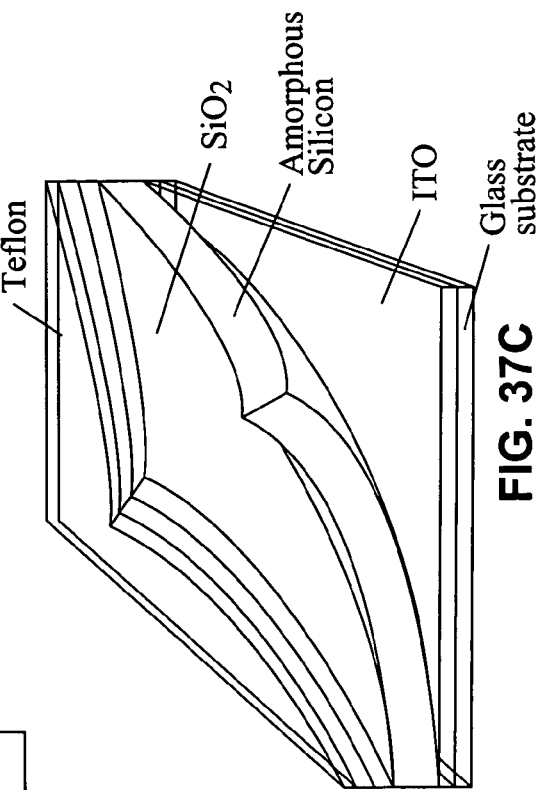
FIG. 37C is a perspective view of the layer structure of the COEW surface according to an aspect of the present invention.

FIGS. 37A-37C illustrate induced movement by electrowetting. In FIG. 37A, a schematic of an example embodiment is illustrated which induces movement of a liquid droplet by an optical beam on the COEW surface. In FIG. 37B an equivalent circuit of the COEW device of FIG. 37A is shown. In FIG. 37C the layered structure of the COEW surface is shown.

OEW allows optical tuning of the voltage across the insulator and thus the contact angle. Our previous results have demonstrated that using halogen lamp with an intensity of 65 mW/cm² is sufficient to reduce the contact angle of the droplet from 105° to 75°, turning hydrophobic surface to hydrophilic. Using OEW, we have demonstrated a droplet-based microfluidic device that allows an optical beam to extract a droplet from a liquid reservoir and transport it freely on a two-dimensional surface. Separation of the droplet is achieved with two optical beams moving in opposite directions. The droplet (100 nL volume) follows the scanning optical beam up to a speed of 70 mm/sec, demonstrating the effectiveness of OEW for optical manipulation of microfluid. The minimum droplet size is limited by the area of the OEW electrodes (>1 nL for an electrode area of 100 μm×100 μm).

For manipulating sub-nano-liter droplet the present invention includes a continuous OEW (COEW) device that allows optical beams to create virtual electrodes that can be continuously addressed on a two-dimensional surface.

FIG. 37A shows the structure of the COEW device. It consists of two surfaces, a top ITO glass and a bottom photosensitive COEW surface. The top ITO glass is coated with a 0.2 μm thick silicon dioxide layer and a 20 nm thick Teflon layer, making the surface hydrophobic; and the bottom COEW surface consists of multiple featureless layers, including a 200 nm thick ITO, 10 nm thick aluminum, 5 μm thick undoped amorphous silicon, 200 nm thick silicon dioxide, and a 20 nm thick Teflon layers, as shown in FIG. 37C. The liquid droplet is sandwiched between these two surfaces with a 10 μm gap defined by a photoresist spacer. Due to the hydrophobic Teflon coating, the initial contact angle of the liquid-solid interface is larger than 90°. When a light beam illuminates at one edge of the droplet, it creates a virtual electrode at the photoconductive layer right underneath this edge. The optoelectrowetting effect is turned on locally, reducing the droplet contact angle at the illumination site.

This process can be understood from the equivalent circuit model shown in FIG. 37B. The amorphous silicon layer has smaller capacitance (higher AC impedance) than the silicon oxide layers in the dark because it is ten times thicker. Very small amount of voltage drops across the silicon oxide layer. Under light illumination, the conductivity of amorphous silicon increases by several orders of magnitude, thereby reducing the electrical impedance to a much smaller value than that of the oxide layers. The contact angle is reduced locally, creating an unbalanced pressure on the droplet. The net capillary force pushes the droplet to move toward the laser beam. By scanning the light beam, the droplet is continuously addressed on the COEW surface. There are two factors that may limit the resolution of the light-patterned virtual electrodes: optical diffraction limit and ambipolar electron-hole diffusion length. In the case of amorphous silicon, the ambipolar diffusion length is less than 115 nm, resulting in a electrode resolution only limited by optical diffraction.

The movement of a 100 μL droplet moving on the COEW device is captured by a video camera through a microscope. The movement is directed by a 100 μW HeNe laser with a wavelength of 632 nm. The focused spot size is 20 μm using a 10× objective. The laser beam is steered by a pair of orthogonal galvanometer scanning mirrors (Cambridge Inc.). A 100V AC bias with frequency of 10 kHz is applied through the top ITO glass and the bottom COEW surface.

FIGS. 38A-38D show a sequence of video snapshots showing the droplet moving in a circular pattern with approximately a 100 μm radius. The speed of the droplet is 785 μm/sec. These images show microdroplet transport by COEW. The droplet has a volume of 100 μL and moves in a circular pattern directed by a scanning laser beam. The speed of the droplet is 785 μm/sec.

The virtual electrode created by light illumination can also be used to move microscopic particles in liquid through dielectrophoretic (DEP) force. The DEP force is generated by the interaction of the applied electric field and the induced electric dipoles in neutral particles. An aspect of the invention provides an optoelectronic tweezers (OET) device that exploits such light-induced DEP to move microscopic particles with very low power optical beams. The DEP force has been widely used to manipulate microscale or nanoscale particles. The analytic expression of the DEP force is given by the following equation.

$$F_{dep} = 2\pi a^3 \epsilon_m Re[K^*(\omega)] \nabla(E^2)$$

$$K^*(\omega) = \frac{\epsilon_p^* - \epsilon_m^*}{\epsilon_p^* - 2\epsilon_m^*}, \epsilon_p^* = \epsilon_p - j\frac{\sigma_p}{\omega}, \epsilon_m^* = \epsilon_m - j\frac{\sigma_m}{\omega}$$

In the above equation E is field strength, a is particle radius, $\epsilon_m$ and $\epsilon_p$ are the permittivities of the surrounding medium and the particle, respectively, $\sigma_m$ and $\sigma_p$ are the conductivity of the medium and the particle, respectively, with ω the angular frequency of the applied electric field. The value $K^*(\omega)$ is the Clausius-Mossotti factor and is a frequency dependent complex number. The real part of $K^*(\omega)$, or $Re[K^*(\omega)]$, has a value between 1 and −0.5, depending on the polarizabilities of the medium and the particle and on the frequency of the applied AC electric bias. If $Re[K^*(\omega)]>0$, the particle will move towards higher electric field region and this is called positive DEP. On the other hand, if $Re[K^*(\omega)]<0$, the particle will move away from the high field region and this is called negative DEP.

Figure 39:
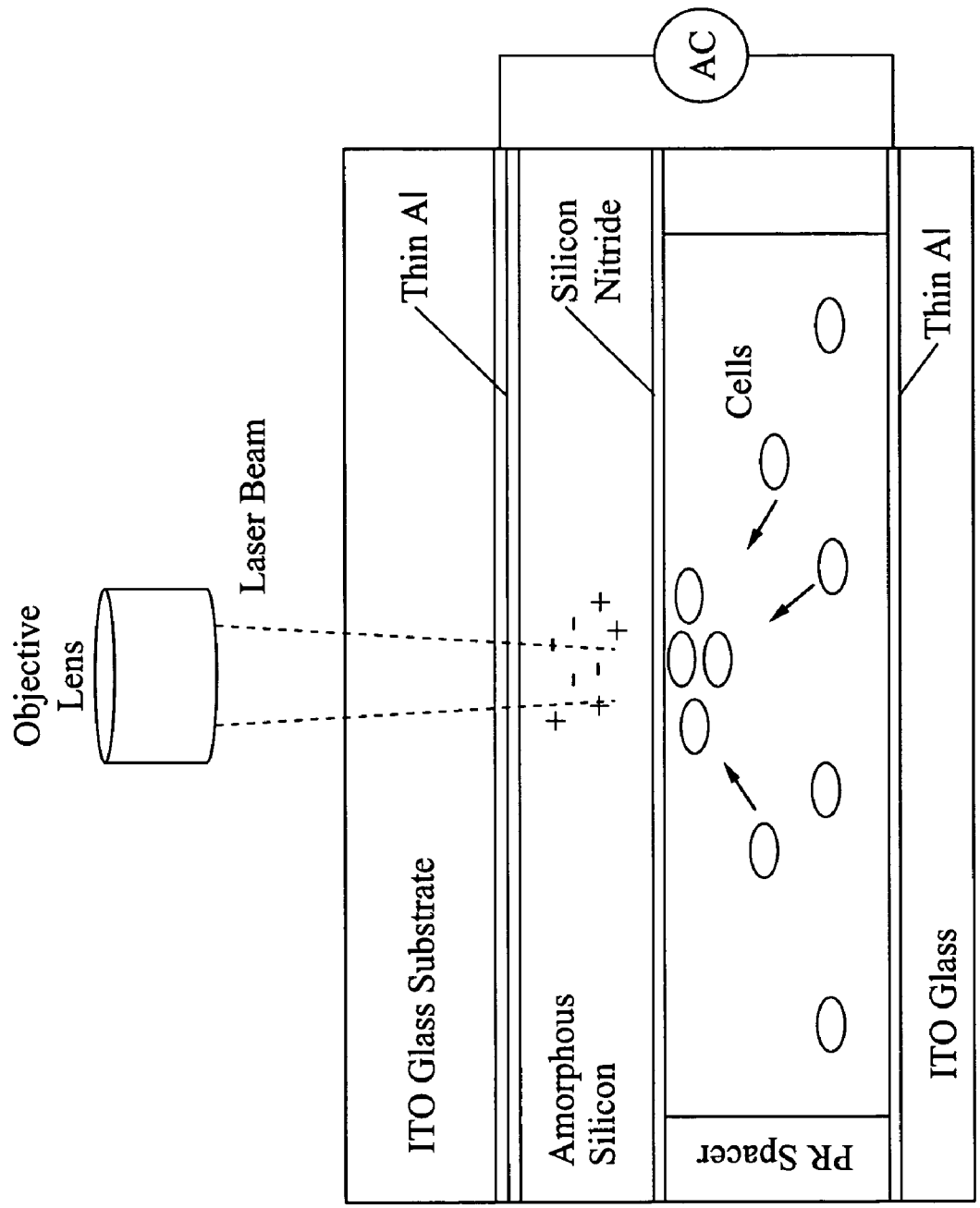
FIG. 39 is a schematic of an OET device according to an aspect of the present invention, showing particle containing liquid retained within a structure having a photoconductive surface for converting optical energy to an electric field.

FIG. 39 illustrates an example embodiment of an OET structure in which the liquid containing the cells or particles are sandwiched between an ITO glass and a photoconductive surface. To achieve light-induced DEP, we use a device structure that is very similar to the OEW device but without the Teflon and silicon dioxide layers on either the ITO or the photosensitive surfaces, as shown in the figure. The 1 μm thick amorphous silicon is coated with 20 nm silicon nitride layer to prevent electrolysis. As in the OEW device, the amorphous silicon layer has high resistance in the dark, resulting a small voltage drop across the liquid layer. Under light illumination, the virtual electrodes create a non-uniform electric field in the liquid layer, producing a DEP force on the particles nearby. The particles can be attracted or repelled by the optical beam, depending on the sign of the Clausius-Mossotti factor. The photoconductive gain of the amorphous silicon allows OET to operate with very low optical power.

Our previous results showed a 1 μW He—Ne laser with wavelength at 633 nm is sufficient to transport a 25 μm particle at 4.5 μm/sec. Though the structures are similar, the OET and the OEW are different in the following aspect: the OET switches the voltage between the photoconductive layer and the liquid layer, while the OEW switches the voltage between the insulating layer and the photoconductive layer.

In this section, we present the applications of OET for collecting and transporting biological cells. To accommodate the size of E. coli cells, the gap spacing in OET is reduced to 15 μm. FIG. 40A shows the simulated electric field distribution in the liquid layer for a 17 μm virtual electrode generated by a focused laser beam and a bias voltage of 10 V. The conductivity of the liquid is 1 mS/m. The conductivity of the amorphous silicon follows the intensity distribution of the laser beam, and is assumed to have a Gaussian shape with a peak conductivity of 10 mS/m at the center. The three-dimensional electrical field distribution is calculated using FEM-LAB.

Figure 40B:
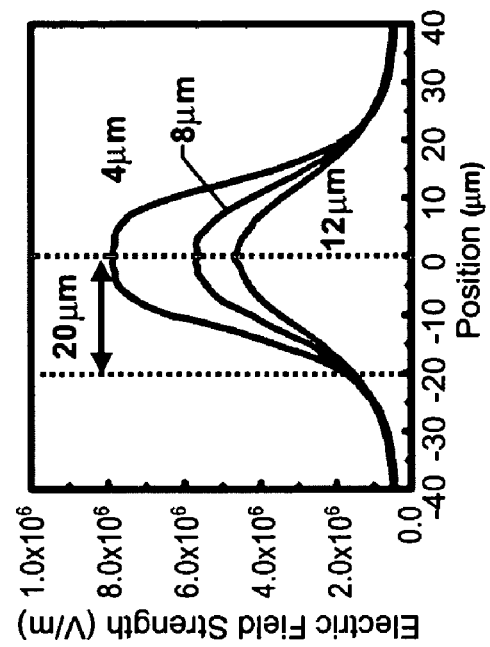
FIGS. 40A-40B are graphs of electric field distribution and strength within the liquid layer in response to photoconductor illumination.
Figure 40A:
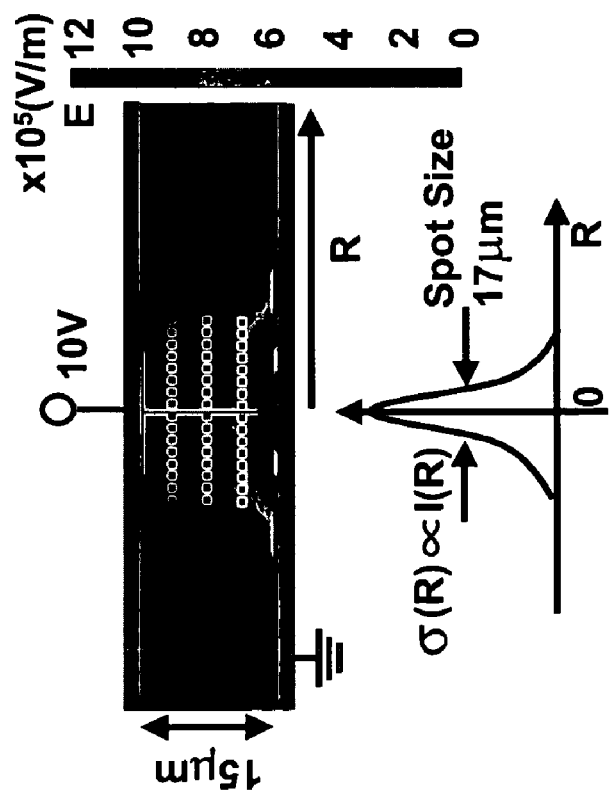

FIG. 40A and FIG. 40B illustrate electric field properties for a photoconductor layer. FIG. 40A illustrates electric field distribution in the liquid layer when the photoconductor is illuminated by a focused laser beam with 17 μm spot size. FIG. 40B The electric field strength at three different heights above the photoconductive layer. The electric field distribution at 4 μm, 8 μm, and 12 μm above the photoconductive surface are plotted in FIG. 40B. Since the DEP force is proportional to the gradient of E2, the electric field distribution shows that the OET can generate strong DEP force within a radius of approximately 20 μm in the lateral direction. The vertical gradient attracts the particles towards the photoconductive surface. Both the lateral and the vertical gradients are strongest near the edge of the laser spot, similar to those generated by a physical electrode.

Figure 41:
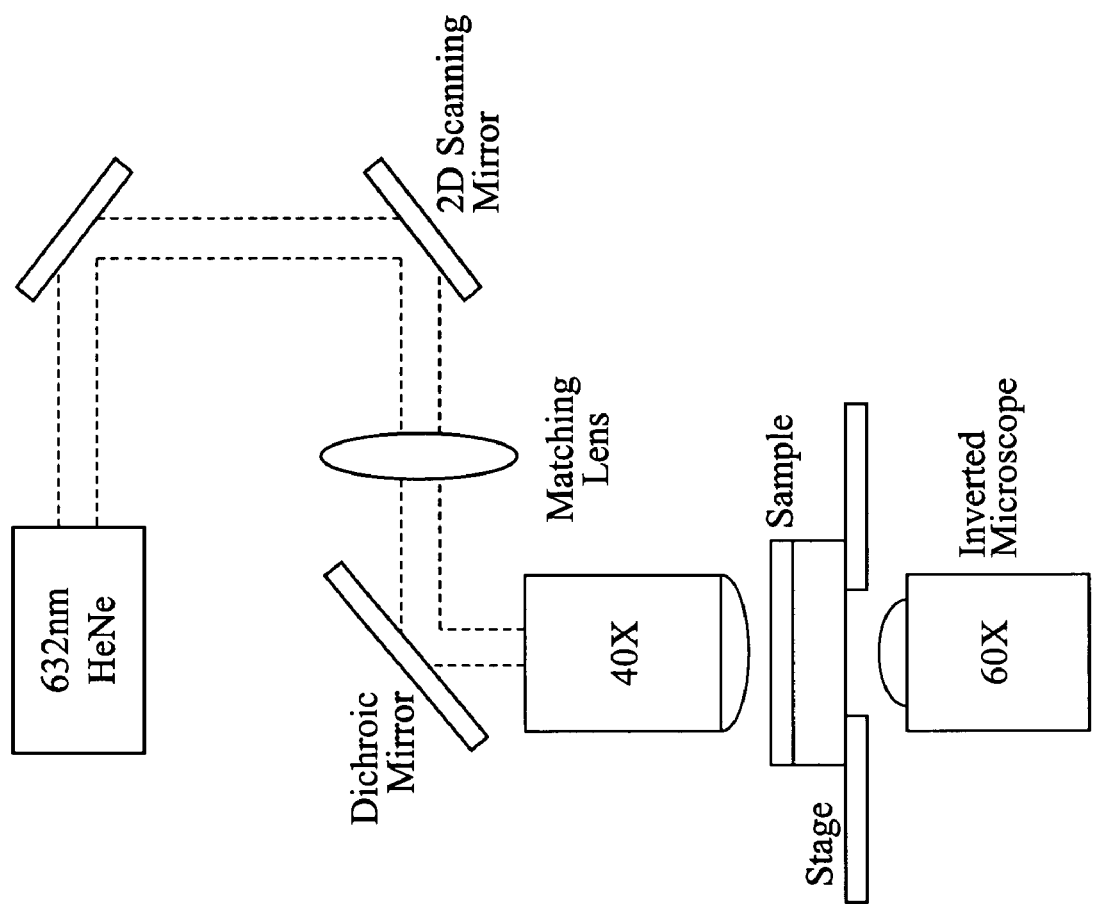
FIG. 41 is a schematic of an experimental setup for trapping *E. coli* cells with an OET device according to an aspect of the present invention.

FIG. 41 illustrates a demonstration setup for trapping biological cells. The OET device is coupled to an microscopic imaging means, such as placed on an inverted microscope (i.e., Nikon® TE2000E) with the photosensitive side up. A 0.8 mW He—Ne laser (wavelength=632 nm) is used to power the optoelectronic tweezers. The incident power is controlled by neutral density filters. The optical beam is delivered to the device through a 40× objective lens with a numerical aperture (N.A.) of 0.5, thereby producing a 17 μm focused spot size. The fluorescent image of the cells is captured by a CCD camera through the bottom objective lens.

Figure 42A:
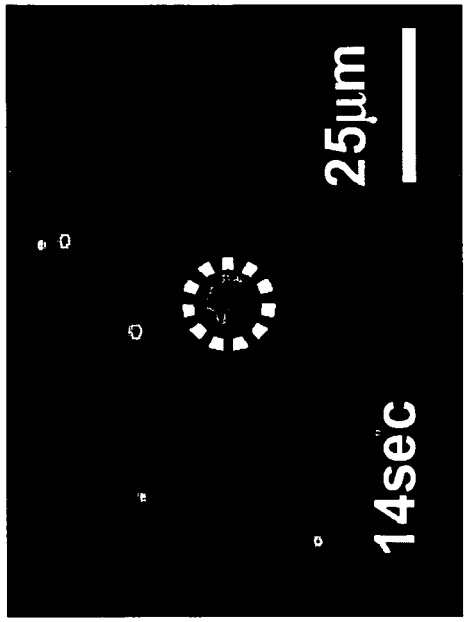
FIGS. 42A-42B are images of cells being collected, "focused", according to an aspect of the present invention.
Figure 42B:
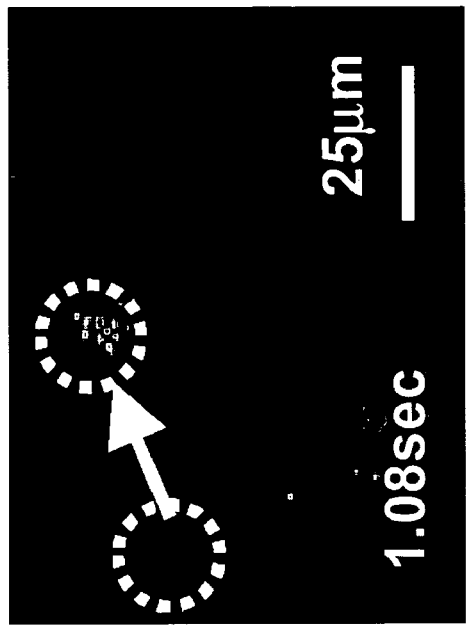

FIG. 42A is an image of fluorescent E. coli cells before OET is turn on. FIG. 42B is the same image as FIG. 42A after the OET is turned on for 14 seconds. It should be appreciated that the E. coli cells are "focused" by the OET to the laser spot.

When the laser beam is focused on a fixed spot, the OET attracts cells within the trapping area towards the center of the beam, as shown in FIG. 42A and FIG. 42B. It functions as a cell concentrator. In this experiment, we use the E. coli cells that can express green fluorescent protein (GFP) for the convenience of observation under fluorescent microscope. The liquid has a conductivity of 1 mS/m. We apply a 100 kHz, 10$V_{PP}$ (volts peak-to-peak) AC electric bias between the top and the bottom ITO electrodes. The E. coli cells experience positive DEP force under these conditions. The effective capturing distance is around 20 μm from the focal point. Due to the electric field gradient in the vertical direction, the cells are trapped right on top of the photosensitive surface. When the laser beam is turned off, these trapped E. coli cells swim away. No "opticution" is observed even for light in the visible wavelength range, thanks to the low optical intensity.

Figure 43A:
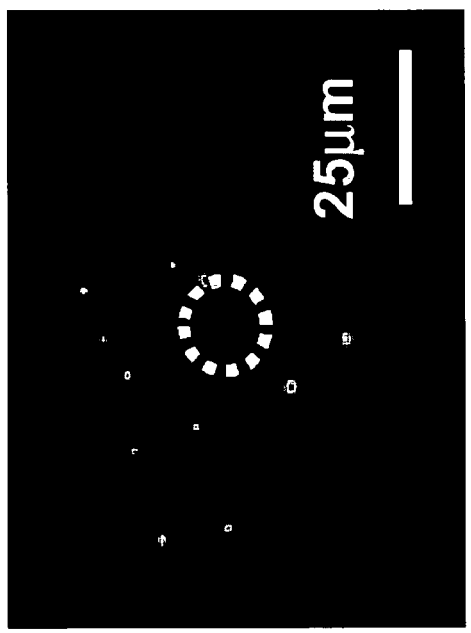
FIGS. 43A-43B are images of cells being transported according to an aspect of the present invention.
Figure 43B:
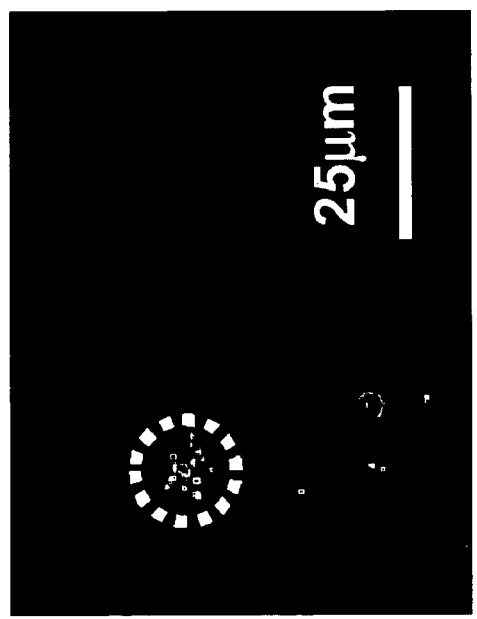

We have investigated the minimum optical power required to operate this OET. Cell concentrating is observed for optical power as low as 8 μW. This optical power density is almost five orders of magnitude lower than that of conventional optical tweezers with 1 mW laser focused to diffraction-limited spot size. The concentrated cells can be transported to any arbitrary location by scanning the laser beam. FIG. 43 shows the transport of multiple E. coli cells using a single scanning laser beam.

To study the effective trapping area and the velocity of the trapped cells, we recorded the trapping action and analyzed the video images frame by frame. The recording microscope is focused on the surface of the photoconductor to capture the trapped cells. We have measured the velocities of cells trapped by lasers with optical powers of μm 8 μW, 120 μW, 400 μW, and 800 μW. The OET traps work at all power levels.

Figure 44:
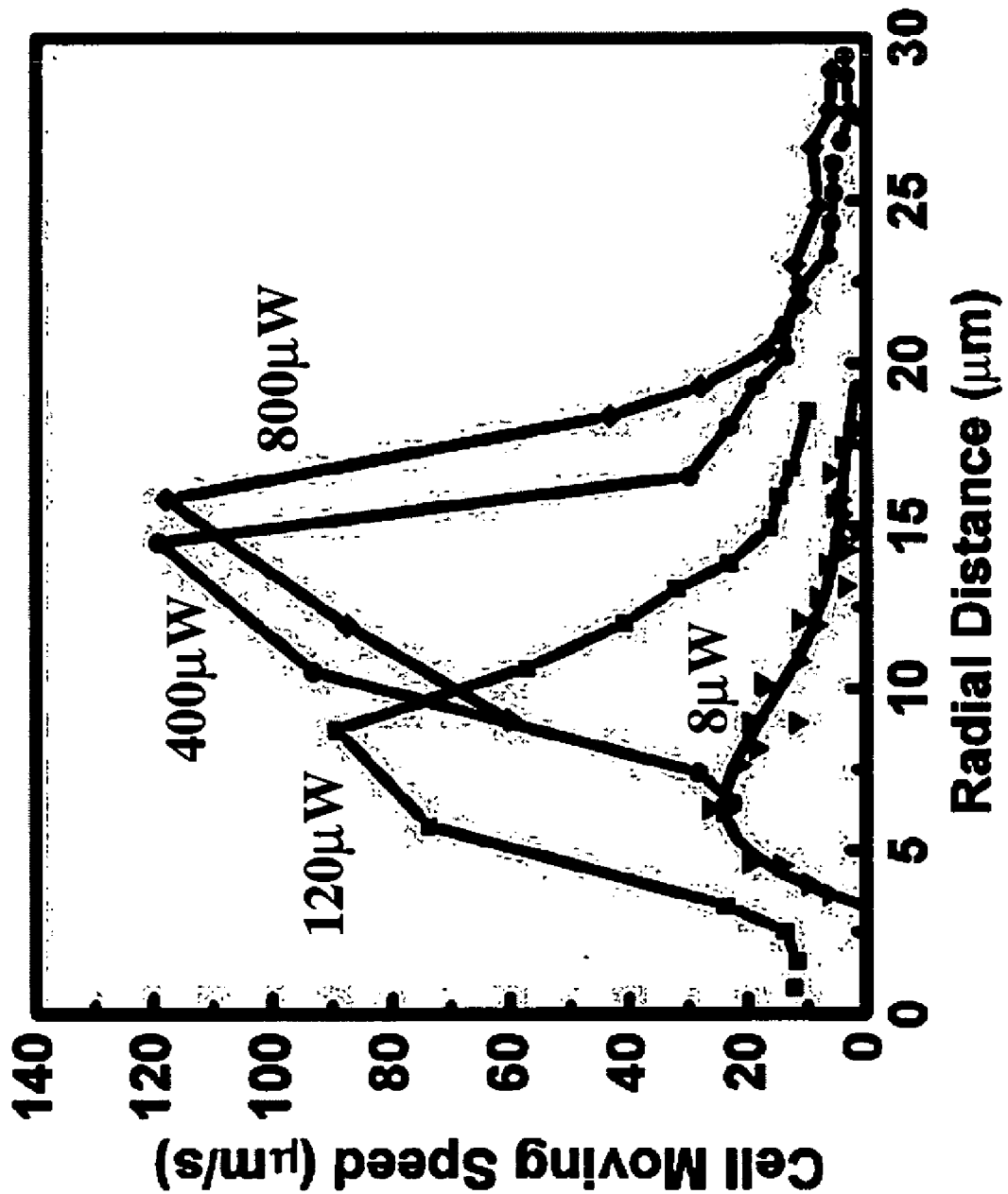
FIG. 44 is a graph of cell movement speed in response to distance and optical power according to an aspect of the present invention.

FIG. 44 shows the measured velocities of the E. Coli cells towards the center of the focused light spot cells versus the radial distance from the center of the trap. At 800 μW, cells as far as 30 μm away are attracted by the OET. Initially, they move at a relatively low speed of 5 μm/sec. The speed increases sharply when they are within 20 μm, eventually reaching a speed of 120 μm/sec at about 15 μm from the focal point. The transport speed becomes smaller after the peak value. The cells are stopped at 9 μm from the center by the trapped cells. This result matches very well with the simulated electric field distribution in FIGS. 40A-40B. The maximum slope of the top curve (4 μm above photoconductor) happens at about 15 μm from the center. The cell velocity is a function of the optical power. The peak velocity increases from 26 μm/sec at 8 μW to about 90 μm/sec at 120 μW. Above 120 μW, the peak velocity increases more slowly, and eventually saturates at about 200 μW. This can be explained by the following: when the optical power is lower than 120 μW, the photoconductor is not fully turned on, for example the conductivity is lower than, but not negligible, compared to the liquid. At about 200 μW, the conductivity of liquid becomes dominant in the electrical circuit, and most of the electric field drops across the liquid layer.

Further increases of optical power do not change the peak electric field. However, the electric field distribution becomes more "square" like because of this saturation effect. The capturing area increases slightly after the peak field saturates. It should be pointed out that the minimum optical power required for OET depends on the liquid conductivity.

The liquid conductivity used in our experiments is 1 mS/m. The current laser power can attract cells in liquid with conductivities up to 100 mS/m. The optical power can be further reduced by shrinking the optical spot size. The current power level can be reduced by 100 times by decreasing the spot size from 17 μm to 1.7 μm.

In this present aspect of the invention we have presented optoelectrowetting (OEW) and optoelectronic tweezers (OET), for manipulating microdroplets and microparticles by light. The OEW uses light-induced electrowetting to control the surface tension, the dominating force in microscale, and actuate microdroplets. Our result shows that a 100 pL water droplet is transported at a speed of 785 μm/sec with an optical power of 100 μW. The OET exploits light-induced dielectrophoretic force for manipulating microparticles. The optical power required by OET is as low as 8 μW and the optical power density is five orders of magnitude lower than that of optical tweezers. We have used OET to concentrate and transport live E. coli cells without photodamage. The low power requirement of OET opens up the possibility of trapping microscopic particles using incoherent light sources.

Embodiments have been described for practicing the apparatus and method of the invention by way of example. It should be appreciated that the specific demonstration/experimental setups were provided only by way of reference and that the invention can be implemented in a wide variety of ways using various equipment as will be recognized by one of ordinary skill in the art. It should be recognized that although the present invention provides an OET which can be implemented with unpatterned surfaces, the teachings herein can be combined with patterned techniques to provide a hybrid approach without departing from the teachings of the present invention. Additionally, specific values for particle transport, times, and other measured characteristics were provided to aid those in understanding the approximate results which can be gleaned from this technology; one of ordinary skill in the art will appreciate that in many cases the results can be significantly improved with more detailed implementations beyond these demonstrations. Furthermore, it should be appreciated that the aspects of the present invention can be practiced on the areas as described, or in other areas which will be recognized by those of ordinary skill in the art based on the teachings herein.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for".

What is claimed is:

1. An apparatus for manipulating cells or particles by light induced dielectrophoresis (DEP), the apparatus comprising:
    a first surface and a second surface configured for retaining a liquid comprising particles or cells to be manipulated;
    at least one photoconductive area on said first or said second surface configured for conversion of received light to a local electric field in the vicinity of the received light;
    a light source to provide the light received by the photoconductive area;
    wherein the local electric field selectively repels or attracts particles or cells;
    a microvision-based pattern recognition subsystem which is configured for controlling the output of said light source in response to registering the position of, and optionally the characteristics of, particles or cells as determined from microscopic imaging.

2. An apparatus as recited in claim 1, wherein said characteristics are selected from the group of particle and cell characteristics consisting essentially of size, color, shape, texture, viability, motility, conductivity, permeability, capacitance and response to changes in the environment of the particle or cell.

3. An apparatus for manipulating cells and particles using optical image-driven light induced dielectrophoresis (DEP) over a two-dimensional area, comprising:
    a first surface and second surface configured for retaining a liquid containing particles, or cells to be manipulated;
    at least one photoconductive area on said first or second surface which is configured for inducing a local electric field, virtual electrode, in the vicinity of received light;
    an optical projector or scanning laser configured for generating dynamic sequential two-dimensional light patterns onto said photosensitive surface thereby inducing dynamic localized electric fields for DEP manipulation of particles or cells; and
    a microscopic imaging subsystem which is configured for controlling the output of said optical projector in response to registering the position of, and optionally the characteristics of, particles or cells as determined from analyzing microscopic images.

4. An apparatus as recited in claim 3, wherein said characteristics are selected from the group of particle and cell characteristics consisting essentially of size, color, shape, texture, viability, motility, conductivity, permeability, capacitance and response to changes in the environment of the particle or cell.

* * * * *

UNITED STATES PATENT AND TRADEMARK OFFICE
CERTIFICATE OF CORRECTION

| | | |
|---|---|---|
| PATENT NO. | : 7,612,355 B2 | Page 1 of 1 |
| APPLICATION NO. | : 11/105304 | |
| DATED | : November 3, 2009 | |
| INVENTOR(S) | : Wu et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 663 days.

Signed and Sealed this

Nineteenth Day of October, 2010

David J. Kappos
*Director of the United States Patent and Trademark Office*